US007989462B2

(12) United States Patent
Cai et al.

(10) Patent No.: US 7,989,462 B2
(45) Date of Patent: Aug. 2, 2011

(54) 4-ARYLAMIN-OR-4-HETEROARYLAMINO-QUINAZOLINES AND ANALOGS AS ACTIVATORS OF CASPASES AND INDUCERS OF APOPTOSIS AND THE USE THEREOF

(75) Inventors: Sui Xiong Cai, San Diego, CA (US); Mark B. Anderson, Salt Lake City, UT (US); Adam Willardsen, Sandy, UT (US); Nilantha Sudath Sirisoma, San Diego, CA (US); Hong Zhang, San Diego, CA (US); Kazuyuki Suzuki, Murray, UT (US)

(73) Assignee: Myrexis, Inc., Salt Lake City, UT (US)

( * ) Notice: Subject to any disclaimer, the term of this patent is extended or adjusted under 35 U.S.C. 154(b) by 477 days.

(21) Appl. No.: 11/773,303

(22) Filed: Jul. 3, 2007

(65) Prior Publication Data

US 2008/0004297 A1     Jan. 3, 2008

Related U.S. Application Data

(63) Continuation-in-part of application No. 10/885,903, filed on Jul. 6, 2004, now Pat. No. 7,618,975, and a continuation-in-part of application No. PCT/US2006/000056, filed on Jan. 3, 2006.

(60) Provisional application No. 60/484,325, filed on Jul. 3, 2003, provisional application No. 60/493,006, filed on Aug. 7, 2003, provisional application No. 60/557,556, filed on Mar. 29, 2004, provisional application No. 60/571,288, filed on May 14, 2004, provisional application No. 60/641,260, filed on Jan. 3, 2005.

(51) Int. Cl.
| | |
|---|---|
| A01N 43/90 | (2006.01) |
| A61K 31/519 | (2006.01) |
| C07D 401/00 | (2006.01) |
| C07D 403/00 | (2006.01) |
| C07D 413/00 | (2006.01) |
| C07D 417/00 | (2006.01) |
| C07D 419/00 | (2006.01) |
| C07D 239/02 | (2006.01) |

(52) U.S. Cl. ............... 514/266.21; 514/266.4; 544/284; 544/291; 544/293

(58) Field of Classification Search .................. None
See application file for complete search history.

(56) References Cited

U.S. PATENT DOCUMENTS

| | | | |
|---|---|---|---|
| 2,883,382 A | 4/1959 | Elslager et al. |
| 3,031,450 A | 4/1962 | Fischer et al. |
| 3,213,090 A | 10/1965 | Roch |
| 3,502,681 A | 3/1970 | Allais et al. |
| 3,632,761 A | 1/1972 | Graham et al. |
| 3,769,410 A | 10/1973 | Bertrand |
| 3,971,783 A | 7/1976 | Barnish et al. |
| 4,025,629 A | 5/1977 | Coverdale |
| 4,322,420 A | 3/1982 | Kobayashi et al. |
| 4,421,920 A | 12/1983 | Baudouin et al. |
| 4,435,003 A | 3/1984 | Fletcher |
| 4,464,375 A | 8/1984 | Kobayashi et al. |
| 4,478,833 A | 10/1984 | Roch et al. |
| 4,480,096 A | 10/1984 | Fletcher |
| 4,510,307 A | 4/1985 | Hidaka et al. |
| 4,675,047 A | 6/1987 | Serban et al. |
| 4,714,698 A | 12/1987 | Roch et al. |
| 5,064,833 A | 11/1991 | Ife et al. |
| 5,114,939 A | 5/1992 | Dreikorn et al. |
| 5,145,843 A | 9/1992 | Arnold et al. |
| 5,187,168 A | 2/1993 | Primeau et al. |
| 5,223,505 A | 6/1993 | Hargreaves et al. |
| 5,236,925 A | 8/1993 | Primeau et al. |
| 5,240,940 A | 8/1993 | Arnold et al. |
| 5,256,781 A | 10/1993 | Primeau et al. |
| 5,270,466 A | 12/1993 | Haley |
| 5,276,148 A | 1/1994 | Siegel et al. |
| 5,294,622 A | 3/1994 | Dreikorn et al. |
| 5,330,989 A | 7/1994 | Soll et al. |
| 5,373,011 A | 12/1994 | Haley |
| 5,409,930 A | 4/1995 | Spada et al. |
| 5,436,233 A | 7/1995 | Lee et al. |
| 5,464,781 A | 11/1995 | Armitage et al. |
| 5,478,845 A | 12/1995 | Hansen et al. |
| 5,480,883 A | 1/1996 | Spada et al. |
| 5,565,472 A | 10/1996 | Hamanaka |
| 5,604,251 A | 2/1997 | Heitsch et al. |
| 5,618,814 A | 4/1997 | Heckel et al. |
| 5,618,829 A | 4/1997 | Takayanagi et al. |
| 5,646,153 A | 7/1997 | Spada et al. |
| 5,654,298 A | 8/1997 | Mills et al. |
| 5,654,307 A | 8/1997 | Bridges et al. |
| 5,656,643 A | 8/1997 | Spada et al. |
| 5,707,989 A | 1/1998 | Himmelsbach et al. |
| 5,710,158 A | 1/1998 | Myers et al. |
| 5,714,493 A | 2/1998 | Myers et al. |
| 5,721,237 A | 2/1998 | Myers et al. |
| 5,739,127 A | 4/1998 | Schohe-Loop et al. |
| 5,747,486 A | 5/1998 | Sohda et al. |
| 5,747,498 A | 5/1998 | Schnur et al. |
| 5,760,230 A | 6/1998 | Schohe-Loop et al. |
| 5,795,889 A | 8/1998 | Spada et al. |

(Continued)

FOREIGN PATENT DOCUMENTS

DE     1151806     7/1963

(Continued)

OTHER PUBLICATIONS

Curd, et. al., Journal of the Chemical Society (1947), 775-83.*

(Continued)

*Primary Examiner* — James O Wilson
*Assistant Examiner* — Jeffrey H Murray
(74) *Attorney, Agent, or Firm* — Kelly A. Echols; Herbert L. Ley, III; Myrexis, IP Group

(57) ABSTRACT

Disclosed are 4-arylamino-quinazolines and analogs thereof effective as activators of caspases and inducers of apoptosis. The compounds of this invention are useful in the treatment of a variety of clinical conditions in which uncontrolled growth and spread of abnormal cells occurs.

26 Claims, No Drawings

U.S. PATENT DOCUMENTS

| | | | |
|---|---|---|---|
| 5,874,438 A | 2/1999 | Schohe-Loop et al. |
| RE36,256 E | 7/1999 | Spada et al. |
| 5,948,819 A | 9/1999 | Ohtsuka et al. |
| 5,952,346 A | 9/1999 | Heitsch et al. |
| 5,965,740 A | 10/1999 | Kai et al. |
| 6,002,008 A | 12/1999 | Wissner et al. |
| 6,057,320 A | 5/2000 | Spada et al. |
| 6,080,747 A | 6/2000 | Uckun et al. |
| 6,080,748 A | 6/2000 | Uckun et al. |
| 6,084,095 A | 7/2000 | Bridges et al. |
| 6,124,330 A | 9/2000 | Venet et al. |
| 6,127,374 A | 10/2000 | Bridges |
| 6,136,837 A | 10/2000 | Kai et al. |
| 6,177,433 B1 | 1/2001 | Uckun et al. |
| 6,184,226 B1 | 2/2001 | Chakravarty et al. |
| 6,204,267 B1 | 3/2001 | Tang et al. |
| 6,232,312 B1 | 5/2001 | Pamukcu et al. |
| 6,242,196 B1 | 6/2001 | Spiegelman et al. |
| 6,251,912 B1 | 6/2001 | Wissner et al. |
| 6,265,410 B1 | 7/2001 | Bridges et al. |
| 6,265,425 B1 | 7/2001 | De Porre et al. |
| 6,277,989 B1 | 8/2001 | Chakravarty et al. |
| 6,284,764 B1 | 9/2001 | Kath et al. |
| 6,297,258 B1 | 10/2001 | Wissner et al. |
| 6,313,129 B1 | 11/2001 | Uckun et al. |
| 6,313,130 B1 | 11/2001 | Uckun et al. |
| 6,313,150 B1 | 11/2001 | Ohtsuka et al. |
| 6,316,454 B1 | 11/2001 | Uckun et al. |
| 6,326,373 B1 | 12/2001 | Uckun et al. |
| 6,329,371 B1 | 12/2001 | Kai et al. |
| 6,344,459 B1 | 2/2002 | Bridges et al. |
| RE37,650 E | 4/2002 | Spada et al. |
| 6,384,051 B1 | 5/2002 | Frost et al. |
| 6,391,874 B1 | 5/2002 | Cockerill et al. |
| 6,432,979 B1 | 8/2002 | Frost et al. |
| 6,452,005 B1 | 9/2002 | Uckun et al. |
| 6,455,534 B2 | 9/2002 | Bridges et al. |
| 6,469,013 B2 | 10/2002 | Uckun et al. |
| 6,476,031 B1 | 11/2002 | Chakravarty et al. |
| 6,476,040 B1 | 11/2002 | Lehner et al. |
| 6,486,187 B1 | 11/2002 | Venet et al. |
| 6,492,520 B1 | 12/2002 | Chen |
| 6,495,556 B2 | 12/2002 | Uckun et al. |
| 6,518,283 B1 | 2/2003 | Langham et al. |
| 6,521,620 B1 | 2/2003 | Bridges et al. |
| 6,541,481 B2 | 4/2003 | Kath et al. |
| 6,552,027 B2 | 4/2003 | Uckun et al. |
| 6,552,055 B1 | 4/2003 | Spiegelman et al. |
| 6,562,319 B2 | 5/2003 | Mishani et al. |
| 6,562,818 B1 | 5/2003 | Bridges |
| 6,602,863 B1 | 8/2003 | Bridges et al. |
| 6,617,329 B2 | 9/2003 | Himmelsbach et al. |
| 6,627,634 B2 | 9/2003 | Himmelsbach et al. |
| 6,635,651 B2 | 10/2003 | Uckun |
| 6,635,655 B1 | 10/2003 | Jayyosi et al. |
| 6,645,969 B1 | 11/2003 | Myers et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,664,247 B2 | 12/2003 | Bebbington et al. |
| 6,713,484 B2 | 3/2004 | Bridges et al. |
| 6,727,251 B2 | 4/2004 | Bebbington et al. |
| 6,740,651 B2 | 5/2004 | Himmelsbach et al. |
| 6,794,389 B2 | 9/2004 | Okana et al. |
| 6,828,320 B2 | 12/2004 | Cockerill et al. |
| 6,833,375 B2 | 12/2004 | Venet et al. |
| 6,864,255 B2 | 3/2005 | Geuns-Meyer et al. |
| 6,890,924 B2 | 5/2005 | Kath et al. |
| 7,087,613 B2 | 8/2006 | Norris et al. |
| 2001/0014679 A1 | 8/2001 | Tang et al. |
| 2002/0048271 A1 | 4/2002 | Coffey et al. |
| 2002/0082270 A1 | 6/2002 | Himmelsbach et al. |
| 2002/0147198 A1 | 10/2002 | Chen et al. |
| 2002/0161010 A1 | 10/2002 | Chakravarty et al. |
| 2002/0165243 A1 | 11/2002 | Uckun et al. |
| 2002/0169180 A1 | 11/2002 | Himmelsbach et al. |
| 2002/0177601 A1 | 11/2002 | Himmelsbach et al. |
| 2003/0055068 A1 | 3/2003 | Bebbington et al. |
| 2003/0069248 A1 | 4/2003 | Chakravarty et al. |
| 2003/0087908 A1 | 5/2003 | Geuns-Meyer et al. |
| 2003/0087931 A1 | 5/2003 | Mailliet et al. |
| 2003/0105090 A1 | 6/2003 | Bebbington et al. |
| 2003/0134836 A1 | 7/2003 | Elbaum et al. |
| 2003/0144178 A1 | 7/2003 | Uckun |
| 2003/0144330 A1 | 7/2003 | Spiegelman et al. |
| 2003/0144506 A1 | 7/2003 | Brown |
| 2003/0149045 A1 | 8/2003 | Fatih |
| 2003/0149062 A1 | 8/2003 | Jung et al. |
| 2003/0162799 A1 | 8/2003 | Langham et al. |
| 2003/0165873 A1 | 9/2003 | Come et al. |
| 2003/0186995 A1 | 10/2003 | Kath et al. |
| 2003/0195230 A1 | 10/2003 | Chen et al. |
| 2003/0203922 A1 | 10/2003 | Patel et al. |
| 2003/0220336 A1 | 11/2003 | Jung et al. |
| 2003/0225089 A1 | 12/2003 | Jung et al. |
| 2003/0229051 A1 | 12/2003 | Bridges et al. |
| 2004/0014774 A1 | 1/2004 | Myers et al. |
| 2004/0034044 A1 | 2/2004 | Okano et al. |
| 2004/0034045 A1 | 2/2004 | Uckun |
| 2004/0038856 A1 | 2/2004 | Chakravarty et al. |
| 2004/0043388 A1 | 3/2004 | Come et al. |
| 2005/0137213 A1 | 6/2005 | Cai et al. |
| 2005/0227992 A1 | 10/2005 | Hurley et al. |
| 2007/0244113 A1 | 10/2007 | Cai et al. |
| 2007/0249601 A1 | 10/2007 | Cai et al. |

FOREIGN PATENT DOCUMENTS

| | | | |
|---|---|---|---|
| DE | 4132763 A1 | 4/1993 |
| DE | 19801438 A1 | 7/1999 |
| DE | 10040527 | 2/2002 |
| DE | 20204129 U1 | 8/2002 |
| FR | 1543405 | 10/1968 |
| FR | 1543448 | 10/1968 |
| FR | 1557928 | 2/1969 |
| FR | 2047882 | 3/1973 |
| FR | 2229413 A1 | 12/1974 |
| GB | 807826 | 1/1959 |
| GB | 971166 | 9/1964 |
| GB | 1195491 | 6/1970 |
| GB | 2033894 | 5/1980 |
| GB | 2052481 | 1/1981 |
| GB | 2230527 | 9/1990 |
| GB | 2295387 A1 | 5/1996 |
| JP | 37007238 | 7/1962 |
| JP | 56020577 | 2/1981 |
| JP | 08003144 A2 | 1/1996 |
| JP | 09301933 | 11/1997 |
| JP | 2003012631 | 1/2003 |
| WO | WO8905297 * | 6/1989 |
| WO | WO 8905297 A1 | 6/1989 |
| WO | WO 9012790 A1 | 11/1990 |
| WO | WO 9205158 A1 | 4/1992 |
| WO | WO 9214714 A1 | 9/1992 |
| WO | WO9214716 * | 9/1992 |
| WO | WO 9214716 A1 | 9/1992 |
| WO | WO 9220642 A1 | 11/1992 |
| WO | WO 9304048 A1 | 3/1993 |
| WO | WO 9308170 A1 | 4/1993 |
| WO | WO 9313097 A1 | 7/1993 |
| WO | WO 9313776 A1 | 7/1993 |
| WO | WO 9315058 A1 | 8/1993 |
| WO | WO 9317682 A1 | 9/1993 |
| WO | WO 9408975 A1 | 4/1994 |
| WO | WO 9414763 A1 | 7/1994 |
| WO | WO 9427994 A1 | 12/1994 |
| WO | WO 9515758 A1 | 6/1995 |
| WO | WO 9519774 A1 | 7/1995 |
| WO | WO 9527693 A1 | 10/1995 |
| WO | WO 9607657 A1 | 3/1996 |
| WO | WO 9609294 A1 | 3/1996 |
| WO | WO 9614319 A1 | 5/1996 |
| WO | WO 9630347 A1 | 10/1996 |
| WO | WO 9639145 A1 | 12/1996 |
| WO | WO 9712863 A1 | 4/1997 |
| WO | WO 9720820 A1 | 6/1997 |
| WO | WO 9720821 A1 | 6/1997 |
| WO | WO 9720822 A1 | 6/1997 |

| | | | |
|---|---|---|---|
| WO | WO 9720823 A2 | 6/1997 | |
| WO | WO 9724328 A1 | 7/1997 | |
| WO | WO 9728133 A1 | 8/1997 | |
| WO | WO 9738983 A1 | 10/1997 | |
| WO | WO 9749704 A1 | 12/1997 | |
| WO | WO 9802434 A1 | 1/1998 | |
| WO | WO 9805661 A1 | 2/1998 | |
| WO | WO 9825598 A2 | 6/1998 | |
| WO | WO 9843960 A1 | 10/1998 | |
| WO | WO 9850370 A1 | 11/1998 | |
| WO | WO 9906378 A1 | 2/1999 | |
| WO | WO 9909016 A1 | 2/1999 | |
| WO | WO 9909986 A1 | 3/1999 | |
| WO | WO 9932098 A2 | 7/1999 | |
| WO | WO 9961428 A1 | 12/1999 | |
| WO | WO 0000202 A1 | 1/2000 | |
| WO | WO 0010981 A1 | 3/2000 | |
| WO | WO 0012497 A2 | 3/2000 | |
| WO | WO 0018740 A1 | 4/2000 | |
| WO | WO 0027819 A2 | 5/2000 | |
| WO | WO 0032175 A2 | 6/2000 | |
| WO | WO 0044728 A1 | 8/2000 | |
| WO | WO 0051587 A2 | 9/2000 | |
| WO | WO 0051991 A1 | 9/2000 | |
| WO | WO 0055141 A1 | 9/2000 | |
| WO | WO 0064888 A1 | 11/2000 | |
| WO | WO 0073260 A1 | 12/2000 | |
| WO | WO 0078735 A1 | 12/2000 | |
| WO | WO 0112227 A1 | 2/2001 | |
| WO | WO 0121594 A1 | 3/2001 | |
| WO | WO 0121595 A1 | 3/2001 | |
| WO | WO 0121596 A1 | 3/2001 | |
| WO | WO 0125218 A1 | 4/2001 | |
| WO | WO 0145641 A2 | 6/2001 | |
| WO | WO 0168186 A2 | 9/2001 | |
| WO | WO 0172710 A1 | 10/2001 | |
| WO | WO 0177104 A1 | 10/2001 | |
| WO | WO 0194341 A1 | 12/2001 | |
| WO | WO 0198277 A2 | 12/2001 | |
| WO | WO 0218370 A1 | 3/2002 | |
| WO | WO 0218372 A1 | 3/2002 | |
| WO | WO 0218376 A1 | 3/2002 | |
| WO | WO 0224666 A2 | 3/2002 | |
| WO | WO 0224667 A1 | 3/2002 | |
| WO | WO 0230927 A1 | 4/2002 | |
| WO | WO 0232872 A1 | 4/2002 | |
| WO | WO 0236577 A1 | 5/2002 | |
| WO | WO 0243735 A1 | 6/2002 | |
| WO | WO 0247690 | 6/2002 | |
| WO | WO 02055501 A2 | 7/2002 | |
| WO | WO 02059112 A2 | 8/2002 | |
| WO | WO 02066461 A1 | 8/2002 | |
| WO | WO 02068406 A2 | 9/2002 | |
| WO | WO 02068415 A1 | 9/2002 | |
| WO | WO 02073235 A2 | 9/2002 | |
| WO | WO 02074341 A1 | 9/2002 | |
| WO | WO 02076975 A1 | 10/2002 | |
| WO | WO 02083654 A1 | 10/2002 | |
| WO | WO 03005026 A2 | 1/2003 | |
| WO | WO 03028641 A2 | 4/2003 | |
| WO | WO 03040108 A1 | 5/2003 | |
| WO | WO 03040109 A2 | 5/2003 | |
| WO | WO 03045395 A1 | 6/2003 | |
| WO | WO 03045939 A1 | 6/2003 | |
| WO | WO 03066060 A2 | 8/2003 | |
| WO | WO 03066602 A1 | 8/2003 | |
| WO | WO 03082290 A1 | 10/2003 | |
| WO | WO 03084503 A1 | 10/2003 | |
| WO | WO 03084539 A2 | 10/2003 | |
| WO | WO 03089439 A1 | 10/2003 | |
| WO | WO 03091224 A1 | 11/2003 | |
| WO | WO 03097615 A1 | 11/2003 | |
| WO | WO 2004007457 A2 | 1/2004 | |
| WO | WO 2004007481 A2 | 1/2004 | |
| WO | WO 2004035543 A1 | 4/2004 | |
| WO | WO 2004078114 | 9/2004 | |
| WO | WO2005003100 | * 1/2005 | |
| WO | WO 2006014420 A1 | 9/2006 | |

OTHER PUBLICATIONS

Dorwald F. A. Side Reactions in Organic Synthesis, 2005, Wiley: VCH, Weinheim p. IX of Preface.*

Vippagunta et. al. Advanced Drug Delivery Reviews 48 (2001) 3-26.*

Borisy et al., "Systematic discovery of multicomponent therapeutics", PNAS—Proceedings of the National Academy of Sciences of the United States of America, Jun. 24, 2003, 100(13):7977-7982.

Abramovitch et al., "Direct acylamination of quinoline, isoquinoline, benzimidazole, pyridazine, and pyrimidine 1-oxides. Novel 1, 5-sigmatropic shift", Journal of Organic Chemistry, 1975, 40(1): 41-50.

Allais et al., "Analgesic compounds with no narcotic activity. Study of new 4 (2' -alkoxycarbonyl phenylamino) quinolines and related molecules", Chimica Therapeutica, 1973, 8(2):154-168.

Almog et al., "Mesomerism in N, N-dialkyl-N-(heteroaryl) amines", Tetrahedron, 1974, 30(4):549-552.

Anwar et al., "Some reactions of 4-cholorquinazoline, 6-nitro- and 6-amino-4 (3H)—quinazolones", Revue Roumaine de Chimie, 1981, 26(11-12):1469-1478.

Apelt et al., "Development of a New Class of Nonimidazole Histmine H3 Receptor Ligands with Combined Inhibitory Histamine N-Methyltransferase Activity", Journal of Medicinal Chemistry, 2002, 45(5):1128-1141.

Assefa et al., "3D-QSAR and docking studies on 4-anilinoquinazoline and 4-anilinoquinoline epidermal growth factor receptor (EGFR) tyrosine kinase inhibitors", Journal of Computer-Aided Molecular Design, 2003, 17(8):475-493.

Bala et al., "Studies on the structure of 2-phenylquinoline-3-carboxylic acid derivatives", Zeszyty Naukowe Uniwersytetu Jagiellonskiego, Prace Chemiczne, 1976, 21:179-189.

Barluenga et al., "Reaction of 3-amino-2-alkenimines with alkali metals: unexpected synthesis of substituted 4- (arylamino) quinolines", Journal of Organic Chemistry, 1989, 54(11):2596-2598.

Berlot et al., "Aminoquinolines. XI. Decomposition of tertiary 4-aminoquinolines and of related amines by hydrobromic acid in aqueous solution. Influence of the nature of the ring and of the hydrocarbon chain", Bulletin de la Societe Chimique de France, 1973, 11 Pt. 2:3175-3178.

Bethegnies et al., "7-Chloro (phenylthio)-4-phenylaminoquinolines. Study on the anti-inflammatory and analgesic activities", Farmaco, Edizione Scientifica, 1986, 41(6):471-477.

Boschelli et al., "Synthesis and Src kinase inhibitory activity of a series of 4-phenylamino-3-quinolinecarbonitriles", Journal of Medicinal Chemistry, 2001, 44(5):822-833.

Bouey-Bencteux et al., "Synthesis and antiproliferative properties of 4-aminoquinazoline derivatives as inhibitors of EGF receptor-associated tyrosine kinase activity", Anti-Cancer Drug Design, 1998, 13(8):893-922.

Bridges et al., "Tyrosine kinase inhibitors: unusually steep structure-activity relationship for analogs of 4- (3-bromoanilino)-6, 7-dimethoxyquinazoline (PD 153035), a potent inhibitor of the epidermal growth factor receptor", Journal of Medicinal Chemistry, 1996, 39(1):267-276.

Dass et al., Journal of Scientific & Industrial Research, 1952, 11B:461-463.

Database Beilstein 1992, XP002314667, Database Accession No. 636504.

Database Beilstein 1992, XP002314668, Database Accession No. 329732.

Database Caplus, Chemical Abstracts Services, XP002314666, Database Accession No. 1960:131417.

Denny, William A., "The 4-anilinoquinazoline class of inhibitors of the erbB family of receptor tyrosine kinases", Farmaco, 2001, 56(1-2):51-56.

Desai et al., "Quinoline derivatives as antitubercular/antibacterial agents", Indian Journal of Chemistry, Section B: Organic Chemistry Including Medicinal Chemistry, 1996, 35B(8):871-873.

Doleschall et al., "4H-3, 1-Benzoxazin-4-ones. VII. Water elimination reactions of N-(2-ureidobenzoyl) anthranilic acids", Tetrahedron, 1968, 24(16):5529-5545.

Dorwald, "Side Reactions in Organic Synthesis", Wiley, 2005, VCH, Weinheim, p. IX of Preface.

Dymek et al., "Additional syntheses and transformations of compounds of the 2, 4-diarylaminoquinazoline type. III", Ann. Univ. Mariae Curie-Sklodowska, Lublin-Polonia Sect. AA, 1956, volume date 1954, 9:45-52.

Dymek et al., "Reactions of acetamide with aniline and phenyl isothiocyanate", Ann. Univ. Mariae Curie-Sklodowska, Lublin-Poloina Sect. AA 1956, volume date 1954, 9:35-43.

Elslager et al., "Amodiaquine N-oxides and other 7-chloro-4-aminoquinoline N-oxides", Journal of Heterocyclic Chemistry, 1984, 1(1):6-12.

Elslager et al., "Antifilarial agents. I. Effects of 4-[(7-chloro-4-quinolyl)amino]-α-(mono-and dialkylamino)-o-cresols and related compounds against Litomosoides carnii in gerbils", Journal of Medicinal Chemistry, 1969, 12(5):965-969.

Elslager et al., "Synthesis and Antimalarial Effects of N2-Aryl-N4-[(dialkylamino)alkyl]- and N4-Aryl-N2-[(dialkylaminoa)alkyl]-2,4-quinazolinediamines", *J. Med. Chem.*, 1981, 24(2):127-140.

Fusco et al., "Reactions of α-arylazo-α-cholroacetic acid esters with cyclic tertiary bases", Gazzetta Chimica Italiana, 1968, 98(5):511-534.

Galanakis et al., "Synthesis and Quantitative Structure-Activity Relationship of Dequalinim Analogs as K+ Channel Blockers: Investigations on the Role of the Substituent at Position 4 of the Quinoline Ring", Journal of Medicinal Chemistry, 1995, 38(18):3536-3546.

Gershuns et al., "Interaction of 2- (2'-benzimidazolyl) quinoline derivatives with Cu+ ions", Ukrainskii Khimicheskii Zhurnal (Russia Edition), 1971, 37(3):263-265.

Gfesser et al., "Synthesis and structure-activity relationships of 5-heteroatom-substituted pyridopyrimidines as adenosine kinase inhibitors", European Journal of Medicinal Chemistry, 2003, 38(3):245-252.

Gineinah et al., "Study on the synthesis of some new 1, 4-dihydro-4-oxoquinazoline derivatives", Zhonghua Yaoxue Zazhi, 1993, 45(1):7-14.

Girgis et al., "Phosphorus pentoxide in organic synthesis 25. New one-step synthesis of 4-aminoquinazolines. Comparison between mass spectra of 4-aminoquinazolines and 6-aminopurines", Chemica Scripta, 1986, 26(4):617-621.

Goossens et al., "DNA Interaction of the Tyrosine Protein Kinase Inhibitor PD153035 and Its N-Methyl Analogue", Biochemistry, 2001, 40(15):4663-4671.

Hamana et al., "Preparation of 2- and 4-substituted quinolines from 1-(2-quinolyl)—and 1- (4-quinolyl) pyridinium salts", Yakugaku Zasshi, 1964, 84:42-47.

Hassan et al., "Determination of glafenine in dosage forms and serum by thin-layer densitometry and high performance liquid chromatography", Journal of Pharmaceutical and Biomedical Analysis, 1997, 16(2):215-221.

Hidaka et al., "Selective inhibitors of three forms of cyclic nucleotide phosphodiesterase—basic and potential clinical applications", Advances in Cyclic Nucleotide and Protein Phosphorylation Research, 1984, 16:245-259.

Himbert et al., "Aminoethynyl metalations. 11. Reaction of silylated and stannylated ynamines with carbodiimides", Liebigs Annalen der Chemie, 1983, (7):1185-1193.

Himbert et al., "Aminoethynyl metalation. Part 3. 3-aminopropiolimidic acid derivatives—(aminoethynyl) stannylation of isocyanates, isothiocyanates, and carbodiimides", Tetrahedron Letters, 1978, (22):1951-1954.

Himbert et al., "Aminoethynyl metalations. 13. Synthesis and reactions of 3-aminopropiolamidines", Liebigs Annalen der Chemie, 1984 (1):85-97.

Hutchings et al., "Unusually high probability of second harmonic generation by some crystalline organic aldehydes", MCLC Section B: Nonlinear Optics, 1994, 7(1-2):157-166.

Ife et al., "Reversible Inhibitors of the Gastric (H+/K+)-ATPase. 5. Substituted 2, 4-Diaminoquinazolines and Thienopyrimidines", Journal of Medicinal Chemistry, 1995, 38(14):2763-2773.

Iida et al., "Fluorescence of 2, 4, 6, 8-substituted pyrimido [5, 4d] pyrimidines", Kogyo Kagaku Zasshi 1967, 70(12):2308-2312.

International Search Report. Mailed Feb. 15, 2005, International Application No. PCT/US2004/021631, Filed Jul. 6, 2004.

Johannsen et al., "Reaction of 4-quinazolinamines with organolithium reagents", Chemica Scripta, 1987, 27(2):277-281.

Kappe et al., "Rearrangements of heterocycles. VIII. Mesoionic six-membered-ring heterocycles. XII. Ketenoid rearrangements of mesoionic pyrimidines", Chemische Berichte, 1979, 112(10):3424-3431.

Kasibhatla et al., "MPC-6827: A Small-Molecule Inhibitor of Microtubule Formation That Is Not a Substrate for Multidrug Resistance Pumps", Cancer Research, Jun. 15, 2007, 67(12):5865-5871.

Lee et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities", Journal of Medicinal Chemistry, 1995, 38(18):3547-3557.

Leiter, "Cancer chemotherapy screening data. VII", Cancer Research, 1960, 20(No. 7, Pt. 2):471-684.

Lin et al., "Some physicochemical parameters of 11H-indolo [3,2-c] quinoline", Heterocycles, 1989, 29(12):2353-2359.

McDonald et al., "Conversion of (2-chlorallyl) amines into heterocyclic compounds. I. 2-Methylindoles, 1,5,6,7-tetrahydro-3methylindol-4-ones, and related heterocycles", Journal of the Chemical Society, Perkin Transactions, 1: Organic and Bio-Organic Chemistry (1972-1999), 1975, (15):1446-1450.

Moreau et al., "Autocorrelation of molecular structures. Application to SAR studies", Nouveau Journal de Chimie, 1980, 4(12):757-764.

Myers et al., "The preparation and SAR of 4- (anilino), 4- (phenoxy), and 4- (thiophenoxy)-quinazolines: inhibitors of p56lck and EGF-R tyrosine kinase activity", Bioorganic Medicinal Chemistry Letters, 1997, 7(4):417-420.

Myers et al., "The synthesis and SAR of new 4-(N-alkyl-N-phenyl) amino-6, 7-dimethoxyquinazolines and 4- (N-alkyl-N-phenyl) aminopyrazolo [3,4,d] pyrimidnes, inhibitors of CSF-1R tyrosine kinase activity", Bioorganic Medicinal Chemistry Letters, 1997, 7(4):421-424.

Rachid et al., "The Combi-Targeting Concept: Chemical Dissection of the Dual Targeting Properties of a Series of "Combi-Triazenes"", Journal of Medicinal Chemistry, 2003, 46(20):4313-4321.

Rewcastle et al., "Tyrosine kinase inhibitors. 5. Synthesis and structure-activity relationships for 4-[ (phenylmethyl) amino]—and 4-(phenylamino) quinazolines as potent adenosine 5'-triphosphate binding site inhibitors of the tyrosine kinase domain of the epidermal growth factor receptor", Journal of Medicinal Chemistry, 1995, 38(18):3482-3487.

Rigby et al., "Preparation of Highly Substituted 4-Aminopyridones via the Reaction of 2-Methylene Dihydrobenzimidazole with Vinyl Isocyanates", Organic Letters, Mar. 14, 2003, 5(7):1151-1153.

Schaumann et al., "New synthesis and reaction behavior of aminoethynyl sulfides", Chemische Berichte, 1983, 116(2):509-513.

Tronchet et al., "C-Glycosyl derivatives. XLII. Synthesis of novel types of C-glycosyl derivatives from acetylenic sugars or their partial synthetic equivalents. Preliminary Communicaton", Helvetica Chimica Acta, 1981, 64(7):2322-2327.

Warhurst et al., "The chemotherapy of rodent malaria. XXXIII. The activity of chloroquine and related blood schizonticides and of some analogs in drug-induced pigment clumping", Annals of Tropical Medicine Parasitology, 1982, 76(3):257-264.

Wright et al., "Anilinoquinazoline Inhibitors of Fructose 1, 6-Bisphosphatase Bind at a Novel Allosteric Site: Synthesis, in Vitro Characterization, and X-ray Crystallography", Journal of Medicinal Chemistry, 2002, 45(18):3865-3877.

Yum et al., "Synthesis and pharmacological profile of 1-aryl-3-substituted pyrrolo [3,2-c] quinolines", Bioorganic Medicinal Chemistry Letters, 1999, 9(19):2819-2822.

Zankowska-Jasinska et al., "2-Benzhydrylmethyl-4-phenylaminoquinoline salts with dicarboxylic acids", Zeszyty Naukowe Uniwersytetu Jagiellonskiego, Prace Chemiczne, 1976, 21:127-132.

Zieba et al., "Azinyl sufides, part LXIII. 1-Alkyl-4- (arylamino) quinolinium-3-thiolates and 7-alkyl-12H-quino [3,4-b]-1,4-benzothiazinium salts", European Journal of Organic Chemistry, 2000, 16:2947-2953.

Vippagunta et al., Advanced Drug Delivery Reviews, 2001, 48:3-26.

Cecil Textbook of Medicine, $21^{st}$ Edition (2000), Goldman & Bennett (Editors), W.B. Saunders Company (Publisher), Chapter 198, pp. 1060-1074.

* cited by examiner

4-ARYLAMIN-OR-4-HETEROARYLAMINO-QUINAZOLINES AND ANALOGS AS ACTIVATORS OF CASPASES AND INDUCERS OF APOPTOSIS AND THE USE THEREOF

CROSS REFERENCE TO RELATED U.S. APPLICATION

This application is a continuation-in-part of U.S. application Ser. No. 10/885,903, filed Jul. 6, 2004, which claims the benefit of U.S. Provisional Application Ser. No. 60/484,325 filed Jul. 3, 2003, U.S. Provisional Application Ser. No. 60/493,006 filed Aug. 7, 2003, U.S. Provisional Application Ser. No. 60/557,556, filed Mar. 29, 2004, and U.S. Provisional Application Ser. No. 60/571,288, filed May 14, 2004. This application is also a continuation-in-part of international patent application no. PCT/US2006/000056, filed Jan. 3, 2006, which claims the benefit of U.S. Provisional Application Ser. No. 60/641,260, filed on Jan. 3, 2005, each of which are incorporated herein by reference in their entirety.

FIELD OF THE INVENTION

This invention is in the field of medicinal chemistry. In particular, the invention relates to compounds that are activators of caspases and inducers of apoptosis. The invention also relates to the use of these compounds as therapeutically effective anti-cancer agents.

TECHNICAL BACKGROUND

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al, *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. M phase specific antineoplastic drugs, such as vinblastine and paclitaxel, are known to affect tubulin polymerization. The ability of cells to appropriately polymerize and depolymerize tubulin is thought to be an important activity for M phase cell division.

Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

EP520722 discloses derivatives of 4-anilino-quinazolines as inhibitors of the EGFR tyrosine kinase with antitumor activity:

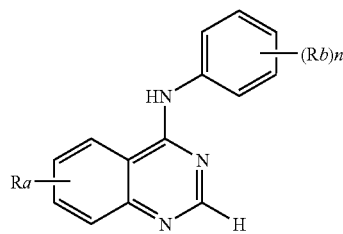

wherein, for example, Ra is hydrogen, trifluoromethyl, or nitro, n is 1; and Rb is halogen, trifluoromethyl or nitro.

EP602851 discloses quinazolines as inhibitors of the EGFR tyrosine kinase:

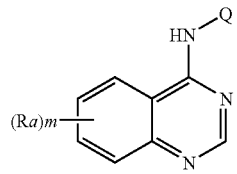

wherein, for example $R^a$ is hydroxy, amino, ureido, or trifluoromethoxy, m is 1, 2 or 3; Q is a 9 or 10-membered bicyclic heterocyclic moiety.

EP635498 discloses 4-anilino-quinazolines as inhibitors of the EGFR tyrosine kinase:

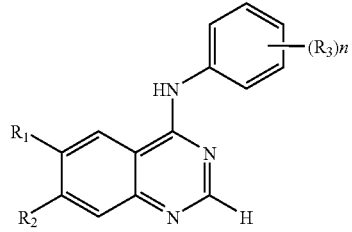

wherein, for example $R_1$ includes hydroxy, amino or $C_{1-4}$ alkoxy, $R_2$ is hydrogen, hydroxy, or halogen, $R_3$ is halogen, n is 1, 2 or 3.

EP635507 discloses tricyclic derivatives as inhibitors of the EGFR tyrosine kinase:

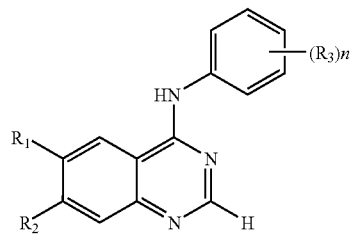

wherein, $R_1$ and $R_2$ together form an optionally substituted 5 or 6 membered ring containing at least one heteroatom; $R_3$ includes hydrogen, hydroxy, or halogen, m is 1, 2 or 3.

WO9609294 discloses substituted heteroaromatic compounds as inhibitors of protein tyrosine kinase:

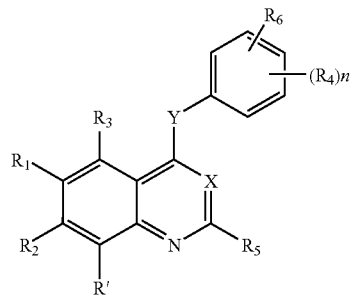

wherein, for example X is N or CH; Y is O, S, or $NR^a$ wherein $R^a$ is H or $C_{1-8}$ alkyl; $R_1$, $R_2$, $R_3$ and $R_{3'}$ includes amino, hydrogen, hydroxy, or halogen; $R_4$ includes amino, hydrogen, hydroxy, or halogen; n is 1, 2 or 3; $R_5$ is selected from the group comprising hydrogen, halogen, trifluoromethyl, $C_{1-4}$ alkyl and $C_{1-4}$ alkoxy; $R_6$ is a group $ZR_7$ wherein Z includes O, S or NH and $R_7$ is an optionally substituted $C_{3-6}$ cycloalkyl, or an optionally substituted 5,6,7,8,9,10-membered carbocyclic or heterocyclic moiety.

WO9713771 discloses substituted heteroaromatic compounds as inhibitors of protein tyrosine kinase:

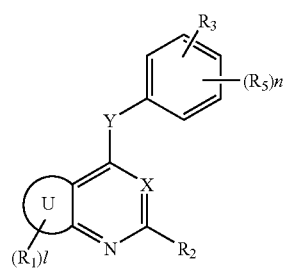

wherein, for example X is N or CH; U represents a fused 5,6,7-membered heterocyclic ring; Y is O, S, or $NR^a$ wherein $R^a$ is H or $C_{1-8}$ alkyl; $R_1$ included 5,6-membered heterocyclic ring, or amino, hydrogen, hydroxy, or halogen; n is 0, 1, 2 or 3. $R_2$ is selected from the group comprising hydrogen, halogen, trifluoromethyl, $C_{1-4}$ alkyl and $C_{1-4}$ alkoxy; $R_3$ is a group $ZR_4$ wherein Z includes O, S or NH and $R_4$ is an optionally substituted $C_{3-6}$ cycloalkyl, or an optionally substituted 5,6, 7,8,9,10-membered carbocyclic or heterocyclic moiety. $R_5$ includes hydrogen, hydroxy, or halogen; n is 1, 2 or 3.

WO9802438 discloses bicyclic heteroaromatic compounds as inhibitors of protein tyrosine kinase:

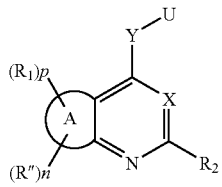

wherein, for example X is N or CH; Y is O, S, or $NR^a$ wherein $R^a$ is H or $C_{1-8}$ alkyl; R" represents a phenyl group or a 5- or 6-membered heterocyclic ring, or amino, hydrogen, hydroxy, or halogen; n is 0 or 1. $R_1$ includes amino, hydrogen, hydroxy, or halogen; p is 0 to 3. $R_2$ is selected from the group comprising hydrogen, halogen, trifluoromethyl, $C_{1-4}$ alkyl and $C_{1-4}$ alkoxy; U represents a 5 to 10-membered mono or bicyclic ring system; A represents a fused 5, 6, or 7-membered heterocyclic ring.

Myers et al (*Bioorg. Med. Chem. Lett.* 7:421-424 (1997)) reported 4-(N-methyl-N-phenyl)amino-6,7-dimethoxyquinazoline as inhibitor of CSF-1R tyrosine kinase. It was reported that substitutions on the phenyl ring resulted in reduced activity. Replacement of the 6,7-dimethoxy groups by hydrogen resulted in more than 40-fold reduction in potency. Substitution in the 2-position of quinazoline by a Cl or methoxy group resulted in inactive compounds ($IC_{50}$>50 μM).

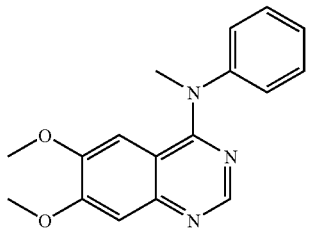

Rewcastle et al. (*J. Med. Chem.* 38:3482-3487 (1995)) reported 4-(phenylamino)-quinazolines as inhibitors of tyrosine kinase of Epidermal Growth Factor Receptor. It was reported that N-methylation of the amino group ($R_1$=Me, $R_2$=$R_3$=$R_4$=H) completely abolished activity ($IC_{50}$>100,000 nM). The 6,7-dimethoxy compound ($R_1$=H, $R_2$=$R_3$=OMe, $R_4$=Br, $IC_{50}$=0.029 nM) was almost 1000-fold more potent than the corresponding non-substituted analog ($R_1$=H, $R_2$=$R_3$=H, $R_4$=Br, $IC_{50}$=27 nM).

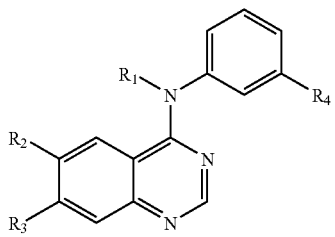

Bridges et al. (*J. Med. Chem.* 39:267-276 (1996)) reported analogs of 4-(3-bromoanilino)-6,7-dimethoxyquinazoline as inhibitors of tyrosine kinase of Epidermal Growth Factor Receptor. It was reported that introduction of a methyl group to the 2-position ($R_1$=Me, $R_2$=3'-Br, $R_3$=H) resulted in at least 400,000-fold loss of potency ($IC_{50}$>10,000 nM) vs the hydrogen analog. Introduction of an amino group to the 2-position ($R_1$=NH_2, $R_2$=3'-Br, $R_3$=H) also resulted in over 18,000-fold loss of potency ($IC_{50}$>10,000 nM). Methylation of the anilino nitrogen ($R_3$=Me) led to 6.000-fold drop in activity. The 4'-Br analog ($IC_{50}$=0.96 nM) was almost 40-fold less active than the 3'-Br analog ($IC_{50}$=0.025 nM), and the 2'-Br analog ($IC_{50}$=128 nM) was at least 5.000-fold less active than the 3'-Br analog.

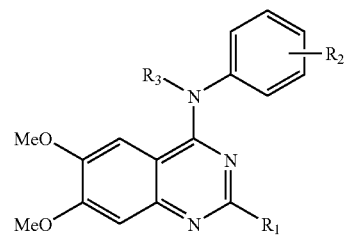

SUMMARY OF THE INVENTION

The present invention is related to the discovery that 4-arylamino-quinazolines and analogs, as represented in Formulae I-II below, are activators of the caspase cascade leading to the activation of caspase-3 and are inducers or promoters of apoptosis. Thus, they are useful in treating or delaying the onset of diseases and disorders that are responsive to the induction of apoptosis.

Accordingly, one aspect of the present invention is directed to the use of compounds of the present invention in inducing capase activities, particularly caspase-3 activities, in inhibiting tubulin, in inhibiting topoisomerase I or II, and inducing or promoting apoptosis, by administering the compounds to cells in vitro or in vivo in warm-blood animals, particularly mammals.

Another aspect of the present invention is to provide a method for treating or delaying the onset of diseases and disorders that are responsive to inhibition of tubulin or topoisomerase II, including but not limited to neoplastic diseases (such as cancer), psoriasis, autoimmune diseases, and fungi infection. The method comprises administering to a subject mammal in need of the treatment a therapeutically effective amount of a compound of the present invention.

Many of the compounds as represented by Formulae I-II below are novel compounds. Therefore, another aspect of the present invention is to provide novel compounds, and to also provide for the use of these novel compounds for treating, preventing or ameliorating neoplasia and cancer.

Yet another aspect of the present invention is to provide a pharmaceutical composition useful for treating disorders responsive to the inhibition of tubulin or topoisomerase II, and the induction of apoptosis, containing an effective amount of a compound of the present invention, preferably in admixture with one or more pharmaceutically acceptable carriers or diluents.

In yet another aspect of the present invention, methods are provided for the preparation of the novel compounds of the present invention.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

It has been discovered that compounds of the present invention are potent inhibitors of tubulin. It is also discovered that the compounds can also inhibit topoisomerase activities, such as topoisomerase II-dependent conversion of supercoiled DNA to topoisomers. The compounds are potent and highly efficacious activators of the caspase cascade particularly caspase-3, and inducers of apoptosis. Therefore, the compounds are useful for treating diseases and disorders responsive to induction of apoptosis, inhibition of tubulin and/or inhibition of topoisomerase II.

Thus, the present invention provides a method of inhibiting tubulin in cells in vitro or in warm-blood animals, particularly mammals, more particularly humans. As used herein, the term "inhibiting tubulin" means inhibiting the polymerization (or assembly) of tubulin monomers or promoting depolymerization of microtubules (i.e., tubulin disassembly). Inhibition of tubulin can be assayed, e.g., by the method described in Example 44 below. The present invention also provides a method for inhibiting topoisomerase II in cells in vitro or in warm-blood animals, particularly mammals, more particularly humans. As used herein, the term "inhibiting topoisomerase II" means inhibiting the activities of the enzyme topoisomerase II in topoisomerase II-dependent conversion of supercoiled DNA to topoisomers. Inhibition of topoisomerase II activities can be assayed by, e.g., a method described in Example 51. In addition, the present invention also provides a method of activating caspase, particularly caspase-3 and inducing apoptosis in cells in vitro or in warm-blood animals, particularly mammals, more particularly humans. The term "activating caspase" as used herein means activating or enhancing the enzymatic (protease) activity of a caspase (e.g., caspase-3), which, if occurring inside cells, results in promoted apoptosis or cell death. The ability of a compound in activating caspase, particularly caspase-3, can be assayed in a method as provided in Example 43 below. The term "inducing apoptosis" as used herein means inducing apoptosis in cells so as to cause cell death. The ability of a compound to induce apoptosis can be tested in a method as described in Example 47 below. Also provided are methods for treating or delaying the onset of diseases and disorders responsive to inhibiting tubulin, inhibiting topoisomerase II, activating caspase-3, or inducing apoptosis. Specific examples of such diseases and disorders are provided in details below.

The above various methods of the present invention can be practiced by or comprise treating cells in vitro or a warm-blood animal, particularly mammal, more particularly a human with an effective amount of a compound according to the present invention. As used herein, the phrase "treating . . . with . . . a compound" means either administering the compound to cells or an animal, or administering to cells or an animal the compound or another agent to cause the presence or formation of the compound inside the cells or the animal. Preferably, the methods of the present invention comprise administering to cells in vitro or to a warm-blood animal, particularly mammal, more particularly a human, a pharmaceutical composition comprising an effective amount of a compound according to the present invention.

Specifically, the methods of the present invention comprise treating cells in vitro or a warm-blood animal, particularly mammal, more particularly a human with an effective amount of a compound according to Formula I:

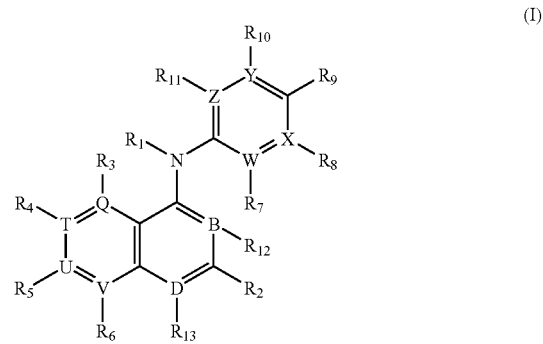

(I)

or a pharmaceutically acceptable salt or solvate thereof, wherein:

$R_1$ is $C_{1-6}$ alkyl, preferably methyl or ethyl, more preferably methyl;

$R_2$ is —$OR_{14}$, —$SR_{14}$, or $NR_{14}R_{15}$ wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl, and any of the groups are optionally substituted by halo, hydroxyl, carboxyl, amino, nitro, cyano, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{1-6}$ acyl, $C_{1-6}$ acylamino, or $C_{1-6}$ acyloxy;

$R_3$-$R_{13}$, are independently selected from:

(a) H, halo, $N_3$, nitro, hydroxy, thiol, and CN, (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$, or -$G^3C(=G^1)G^2R_{41}$, (c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —$N(R^{52})(R^{53})$, —$N(R^{52})C(=O)R_{42}$, —$N(R^{52})C(=O)N(R^{52})(R^{53})$, —$C(=O)N(R^{52})(R^{53})$, —$OC(=O)N(R^{52})(R^{53})$, $R_{42}C(=O)$—, $R_{42}C(=O)O$—, $R_{42}C(=G^1)$-, $R_{42}C(=G^1)G^2$-, $R_{42}C(=G^1)G^2(R^{52})$—, —$C(=G^1)G^2R_{43}$, or -$G^4C(=G)G^2R_{43}$, (d) —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$, or -$G^3C(=G^1)G^2R_{41}$, $G^1$ is S or N; $G^2$ and $G^3$ are independently S or $N(R^{50})$; $G^4$ is $N(R^{52})$;

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$, is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH ($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle (e.g., piperidinyl, pyrrolidinyl, and morpholinyl), wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and B, D, Q, T, U, V, W, X, Y and Z are independently C or N, provided that at least one of B and D is N and when B, D, Q, T, U, V, W, X, Y or Z is N then there is no substituent at the N.

In one embodiment, $R_1$ is $C_{1-2}$ alkyl, preferably $CH_3$;

$R_2$ is —$OR_{14}$, —$SR_{14}$, or $NR_{14}R_{14}$ wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl, and any of the groups are optionally substituted by halo, hydroxyl, carboxyl, amino, nitro, cyano, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{1-6}$ acyl, $C_{1-6}$ acylamino, or $C_{1-6}$ acyloxy;

$R_3$, $R_4$, $R_6$-$R_8$, $R_{10}$-$R_{13}$ are independently $R_{16}$, $OR_{16}$, $SR_{16}$ or $NR_{16}R_{17}$, wherein $R_{16}$ and $R_{17}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy);

$R_5$ is H, F, or $C_{1-3}$ alkyl, preferably H or F, and more preferably H; and $R_9$ is H; OH; halo; $N_3$; $C_{1-6}$ alkyl; $C_{1-6}$ haloalkyl —$OR_{9a}$, wherein $R_{9a}$, is $C_{1-6}$ alkyl or $C_{1-6}$ haloalkyl; —NH($R^a$) or —N($R^a$)($R^b$) where $R^a$ and $R^b$ are independently $C_{1-6}$ alkyl, $C_{1-6}$ acyl, $C_{1-6}$ acyloxy, amino, —(C=O)N($R^c$)($R^d$) wherein $R^d$ and $R^d$ are independently H or $C_{1-6}$ alkyl; or —$COOR_{9b}$, wherein $R_{9b}$ is $C_{1-6}$ alkyl; optionally $R_9$ and one of $R_8$ and $R_{10}$ together form a 3, 4, 5, or 6-membered heterocycle; and any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy); and B, D, Q, T, U, V, W, X, Y and Z are independently C or N, provided that at least one of B and D is N and when B, D, Q, T, U, V, W, X, Y or Z is N then there is no substituent at the N.

In specific embodiments, $R_2$ is $NR_{14}R_{15}$, wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl; and each group is optionally substituted by halo, hydroxyl, carboxyl, amino, nitro, cyano, $C_{1-3}$ alkyl, $C_{2-3}$ alkenyl, $C_{2-3}$ alkynyl, $C_{1-3}$ alkoxy, $C_{1-3}$ alkylthio, $C_{1-3}$ haloalkyl, $C_{1-3}$ acyl, $C_{1-3}$ acylamino, or $C_{1-6}$ acyloxy. In a specific embodiment, $R_2$ is $NR_{14}R_{15}$, wherein $R_{14}$ is arylalkyl (e.g., benzyl or phenylethyl), or heteroarylalkyl ($C_{1-2}$ alkyl substituted with pyridine, pyridazine, pyrimidine, pyrazine or triazine) and $R_{15}$ is H, $C_{1-3}$ alkyl.

In specific embodiments, $R_9$ is H; OH; Cl; $N_3$; $C_{1-3}$ alkyl (preferably methyl; $C_{1-3}$ haloalkyl (preferably monofluoromethyl, difluoromethyl, trifluoromethyl); —$OR_{9a}$, wherein $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —NH($R^a$) or —N($R^a$)($R^b$) where $R^a$ and $R^b$ are independently $C_{1-3}$ alkyl, $C_{1-3}$ acyl, $C_{1-3}$ acyloxy, —(C=O)N($R^e$)($R^f$) wherein $R^e$ and $R^f$ are independently H, or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle.

Preferably, $R_9$ is selected from the group:
—$OR_{19}$, wherein $R_{19}$ is selected from the group of methyl, ethyl, fluoromethyl (e.g., $CH_2F$, $CHF_2$, $CF_3$), and fluoroethyl;
—$NHCH_3$;
—$N(CH_3)_2$;
—$N_3$;
—$COOR_{20}$; and
—NC(O)N($R_{21}$)($R_{22}$) or —NC(O)$R_{20}$ wherein $R_{20}$ is methyl or ethyl; and $R_{21}$ and $R_{22}$ are independently H, methyl or ethyl.

In specific embodiments, $R_3$ is H; halo; $C_{1-3}$ alkyl; or $C_{1-3}$ alkoxy;

$R_4$ and $R_6$ are independently H; halo; $NO_2$, $N_3$; $C_{1-6}$ alkyl; $C_{1-3}$ alkoxy; or —N($R_{2b}$)($R_{2c}$) wherein $R_{2b}$ and $R_{2c}$ are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with —N($R_{2d}$)($R_{2e}$) wherein $R_{2d}$ and $R_{2e}$ are independently H, OH, $C_{1-3}$ alkyl or $C_{2-3}$ hydroxyalkyl, wherein $R_{2b}$ and $R_{2c}$, together may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_5$ is H or F;

$R_7$ and $R_{11}$ are independently H; halo; $CH_3$; or $OCH_3$; and $R_8$ and $R_{10}$ are independently H; halo; OH; $N_3$; $C_{1-3}$ alkyl; $C_{1-3}$ alkoxy; $C_{1-3}$ haloalkyl; —$OR_{9a}$, —$SR_{9a}$ where $R_{9a}$ is $C_{1-4}$ alkyl or $C_{1-3}$ haloalkyl; —NH($R^a$) or —N($R^a$)($R^b$) where $R^a$ and $R^b$ are independently $C_{1-3}$ alkyl; or —$COOR_{9b}$, wherein $R_{9b}$ is $C_{1-3}$ alkyl (preferably methyl or ethyl).

Compounds of Formula I include compounds according to Formula II:

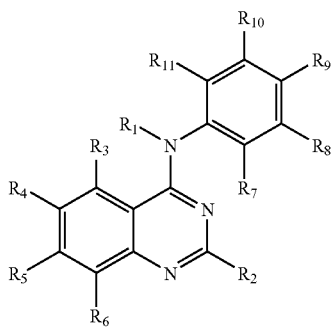

(II)

or pharmaceutically acceptable salts, or solvates thereof, wherein:

$R_1$ is $C_{1-2}$ alkyl, preferably $CH_3$;

$R_2$ is —$OR_{14}$, —$SR_{14}$, or $NR_{14}R_{15}$ wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl, and any of the groups are optionally substituted by halo, hydroxyl, carboxyl, amino, nitro, cyano, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{1-6}$ acyl, $C_{1-6}$ acylamino, or $C_{1-6}$ acyloxy;

$R_3$-$R_{11}$ are independently selected from:
(a) H, halo, $N_3$, nitro, hydroxy, thiol, and CN,
(b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-16}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$,
(c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —$N(R^{52})(R^{53})$, —$N(R^{52})C(=O)R_{42}$, —$N(R^{52})C(=O)N(R^{52})(R^{53})$, —$C(=O)N(R^{52})(R^{53})$, —$OC(=O)N(R^{52})(R^{53})$, $R_{42}C(=O)$—, $R_{42}C(=O)O$—, $R_{42}C(=G^1)$-, $R_{42}C(=G^1)G^2$-, $R_{42}C(=G^1)G^2(R^{52})$—, —$C(=G^1)G^2R_{43}$, or -$G^4C(=G)G^2R_{43}$,
(d) —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$, $G^1$ is S or N; $G^2$ and $G^3$ are independently S or $N(R^{50})$; $G^4$ is $N(R^{52})$;

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle (e.g., piperidinyl, pyrrolidinyl, and morpholinyl), wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl.

In one embodiment, $R_1$ is $C_{1-2}$ alkyl, preferably $CH_3$;

$R_2$ is —$OR_{14}$, —$SR_{14}$, or $NR_{14}R_{14}$ wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl, and any of the groups are optionally substituted by halo, hydroxyl, carboxyl, amino, nitro, cyano, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{1-6}$ acyl, $C_{1-6}$ acylamino, or $C_{1-6}$ acyloxy;

$R_3$, $R_4$, $R_6$-$R_8$, $R_{10}$ and $R_{11}$ are independently $R_{16}$, $OR_{16}$, $SR_{16}$ or $NR_{16}R_{17}$, wherein $R_{16}$ and $R_{17}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy);

$R_5$ is H, F, or $C_{1-3}$ alkyl, preferably H or F, and more preferably H; and $R_9$ is H; OH; halo; $N_3$; $C_{1-6}$ alkyl; $C_{1-6}$ haloalkyl —$OR_{9a}$ wherein $R_{9a}$ is $C_{1-6}$ alkyl or $C_{1-6}$ haloalkyl; —$NH(R^a)$ or —$N(R^a)(R^b)$ where $R^a$ and $R^b$ are independently $C_{1-6}$ alkyl, $C_{1-6}$ acyl, $C_{1-6}$ acyloxy, amino, —(C=O)N($R^c$)($R^d$) wherein $R^c$ and $R^d$ are independently H or $C_{1-6}$ alkyl; or —COOR$_{9b}$, wherein $R_{9b}$ is $C_{1-6}$ alkyl; optionally $R_9$ and one of $R_8$ and $R_{10}$ together form a 3, 4, 5, or 6-membered heterocycle; and any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy).

In specific embodiments, $R_2$ is $NR_{14}R_{15}$, wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl; and each group is optionally substituted by halo, hydroxyl, carboxyl, amino, nitro, cyano, $C_{1-3}$ alkyl, $C_{2-3}$ alkenyl, $C_{2-3}$ alkynyl, $C_{1-3}$ alkoxy, $C_{1-3}$ alkylthio, $C_{1-3}$ haloalkyl, $C_{1-3}$ acyl, $C_{1-3}$ acylamino, or $C_{1-6}$ acyloxy. In a specific embodiment, $R_2$ is $NR_{14}R_{15}$, wherein $R_{14}$ is arylalkyl (e.g., benzyl or phenethyl), or heteroarylalkyl ($C_{1-2}$ alkyl substituted with pyridine, pyridazine, pyrimidine, pyrazine or triazine) and $R_{15}$ is H, $C_{1-3}$ alkyl.

In specific embodiments, $R_9$ is H; OH; Cl; $N_3$; $C_{1-3}$ alkyl (preferably methyl; $C_{1-3}$ haloalkyl (preferably monofluoromethyl, difluoromethyl, trifluoromethyl); —OR$_{9a}$, wherein $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —NH($R^a$) or —N($R^a$)($R^b$) where $R^a$ and $R^b$ are independently $C_{1-3}$ alkyl, $C_{1-3}$ acyl, $C_{1-3}$ acyloxy, —(C=O)N($R^e$)($R^f$) wherein $R^e$ and $R^f$ are independently H, or $C_{1-3}$ alkyl; or —COOR$_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle.

Preferably, $R_9$ is selected from the group:
—OR$_{19}$, wherein $R_{19}$ is selected from the group of methyl, ethyl, fluoromethyl (e.g., $CH_2F$, $CHF_2$, $CF_3$), and fluoroethyl;
—NHCH$_3$;
—N(CH$_3$)$_2$;
—N$_3$;
—COOR$_{20}$; and
—NC(O)N($R_{21}$)($R_{22}$) or —NC(O)$R_{20}$ wherein $R_{20}$ is methyl or ethyl; and $R_{21}$ and $R_{22}$ are independently H, methyl or ethyl.

In specific embodiments,
$R_3$ is H; halo; $C_{1-3}$ alkyl; or $C_{1-3}$ alkoxy;
$R_4$ and $R_6$ are independently H; halo; $NO_2$, $N_3$; $C_{1-6}$ alkyl; $C_{1-3}$ alkoxy; or —N($R_{2b}$)($R_{2c}$) wherein $R_{2b}$ and $R_{2c}$ are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with —N($R_{2d}$)($R_{2e}$) wherein $R_{2d}$ and $R_{2e}$ are independently H, OH, $C_{1-3}$ alkyl or $C_{2-3}$ hydroxyalkyl, wherein $R_{2b}$ and $R_{2c}$ together may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;
$R_5$ is H or F;
$R_7$ and $R_{11}$ are independently H; halo; $CH_3$; or $OCH_3$; and
$R_8$ and $R_{10}$ are independently H; halo; OH; $N_3$; $C_{1-3}$ alkyl; $C_{1-3}$ alkoxy; $C_{1-3}$ haloalkyl; —OR$_{9a}$,
—SR$_{9a}$, where $R_{9a}$ is $C_{1-4}$ alkyl or $C_{1-3}$ haloalkyl; —NH($R^a$) or —N($R^a$)($R^b$) where $R^a$ and $R^b$ are independently $C_{1-3}$ alkyl; or —COOR$_{9b}$, wherein $R_{9b}$ is $C_{1-3}$ alkyl (preferably methyl or ethyl).

The methods of the present invention also comprise treating cells in vitro or a warm-blood animal, particularly mammal, more particularly a human with an effective amount of a compound according to Formula I:

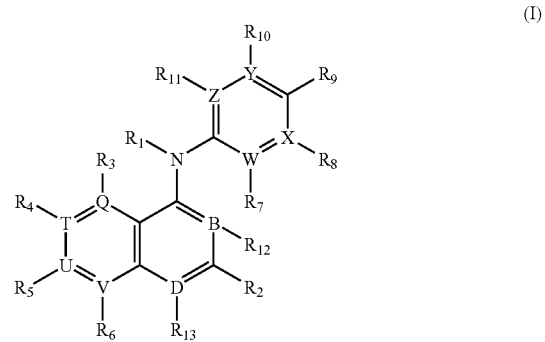

(I)

or a pharmaceutically acceptable salt or solvate thereof, wherein:
$R_1$ is $C_{1-2}$ alkyl, preferably $CH_3$;
$R_2$ is H; halo; $NHNH_2$, $N_3$; $C_{1-6}$ alkyl optionally substituted with OH or halo; —OR$_{2a}$ or —SR$_{2a}$ wherein $R_{2a}$ is $C_{1-6}$ alkyl optionally substituted with OH or halo; —CO$_2C_{1-3}$ alkyl; —N($R^e$)N($R^a$)($R^b$), or —N($R^a$)($R^b$) wherein $R^e$, $R^a$ and $R^b$ are independently H, OH($R^a$ and $R^b$ are not both OH), $C_{1-3}$ alkyl, $C_{1-6}$ hydroxyalkyl, $C_{1-3}$ acyl, $C_{1-3}$ acyloxy, (C=O)N ($R^c$)($R^d$) or $C_{1-6}$ alkyl that is optionally substituted with —N($R^e$)($R^d$) wherein $R^e$ and $R^d$ are independently H, OH($R^c$ and $R^d$ are not both OH), $C_{1-3}$ alkyl, or $C_{2-3}$ hydroxyalkyl, and wherein optionally $R^a$ and $R^b$ together with the nitrogen they both are linked to may form a 3, 4, 5 or 6-membered heterocycle;
$R_3$, $R_4$, $R_6$-$R_8$, $R_{10}$-$R_{13}$ are independently $R_{16}$, OR$_{16}$, SR$_{16}$, $NR_{16}R_{17}$, or $NO_2$, wherein $R_{16}$ and $R_{17}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy);
$R_5$ is H, F, or $C_{1-3}$ alkyl, preferably H or F, and more preferably H;
$R_9$ is H; OH; halo; $N_3$; $C_{1-6}$ alkyl; $C_{1-6}$ haloalkyl —OR$_{9a}$, wherein $R_{9a}$ is $C_{1-6}$ alkyl or $C_{1-6}$ haloalkyl; —NH($R_9$) or —N($R^g$)($R^h$) where $R^g$ and $R^h$ are independently $C_{1-6}$ alkyl, $C_{1-6}$ acyl, $C_{1-6}$ acyloxy, amino, —(C=O)N($R^j$)($R^k$) wherein $R^j$ and $R^k$ are independently H or $C_{1-6}$ alkyl; or —COOR$_{9b}$, wherein $R_{9b}$ is $C_{1-6}$ alkyl; optionally $R_9$ and one of $R_8$ and $R_{10}$ together form a 3, 4, 5, or 6-membered heterocycle; and any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy); and
B, D, Q, T, U, V, W, X, Y and Z are independently C or N, provided that at least one of B and D is N and when B, D, Q, T, U, V, W, X, Y or Z is N then there is no substituent at the N.

In specific embodiments,
$R_3$ is H; halo; $C_{1-3}$ alkyl; or $C_{1-3}$ alkoxy;
$R_4$ and $R_6$ are independently H; halo; $NO_2$, $N_3$; $C_{1-6}$ alkyl; $C_{1-3}$ alkoxy; or —N($R_{2b}$)($R_{2c}$) wherein $R_{2b}$ and $R_{2c}$, are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with —N($R_{2d}$)($R_{2e}$) wherein $R_{2d}$ and $R_{2e}$ are independently H, OH, $C_{1-3}$ alkyl or $C_{2-3}$ hydroxyalkyl, wherein $R_{2b}$ and $R_{2c}$ together may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_5$ is H or F;

$R_7$ and $R_1$ are independently H; halo; $CH_3$; or $OCH_3$; and $R_8$ and $R_{10}$ are independently H; halo; OH; $N_3$; $C_{1-3}$ alkyl; $C_{1-3}$ alkoxy; $C_{1-3}$ haloalkyl; $-OR_{9a}$, $-SR_{9a}$, where $R_{9a}$ is $C_{1-4}$ alkyl or $C_{1-3}$ haloalkyl; $-NH(R^a)$ or $-N(R^a)(R^b)$ where $R^a$ and $R^b$ are independently $C_{1-3}$ alkyl; or $-COOR_{9b}$, wherein $R_{9b}$ is $C_{1-3}$ alkyl (preferably methyl or ethyl).

Preferably, $R_2$ is $-N(R^{50})C(=O)R_{40}$, $-N(R^{50})C(=O)N(R^{50})(R^{51})$, $C(=O)N(R^{50})(R^{51})$, or $-OC(=O)N(R^{50})(R^{51})$; and preferably $R_9$ is $-N(R^{50})C(=O)R_{40}$, $-N(R^{50})C(=O)N(R^{50})(R^{51})$, $-C(=O)N(R^{50})(R^{51})$, or $-OC(=O)N(R^{50})(R_{51})$; wherein $R_{40}$ is selected from: H, $-OH$, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy and $C_{1-4}$ alkylthiol, wherein $R_{40}$ is optionally substituted with from one to three substituents independently selected from halo, $N_3$, nitro, hydroxy, thiol, CN, and $C_{1-4}$ alkyl, and preferably $R_{40}$ is $C_{1-4}$ alkyl optionally substituted by 1-3 F or Cl;

$R^{50}$ and $R^{51}$ are independently H, OH($R^{50}$ and $R^{51}$ are not both OH), $C_{1-4}$ alkyl, $C_{2-4}$ alkenyl, $C_{2-4}$ alkynyl, $C_{1-4}$ alkoxy, $C_{1-4}$ alkylthiol, $C_{2-4}$ alkenyloxy, $C_{2-4}$ alkynyloxy, $C_{1-4}$ haloalkyl, $C_{2-4}$ hydroxyalkyl, $C_{1-4}$ alkyl-O—$C_{1-4}$ alkyl-, or $R^{50}$ and $R^{51}$ together with the nitrogen atom to which they are both linked form a 3, 4, 5 or 6-membered heterocycle (e.g., piperidinyl, pyrrolidinyl, and morpholinyl), and preferably $R^{50}$ and $R^{51}$ are independently H or $C_{1-4}$ alkyl, said alkyl being optionally substituted with 1-3 F or Cl.

In one embodiment of the compounds of Formula I, B is C and D is N. In another embodiment of the compounds of Formula I, B is N and D is C. In other embodiments of the compounds of Formula I, X and/or Y are N; W and/or Z are N; or W and X are N. In additional embodiments of the compounds of Formula I, Q and/or T is N; U and/or V is N; T and U are N; or Q and V are N.

The methods of the present invention also comprise treating cells in vitro or a warm-blood animal, particularly mammal, more particularly a human with an effective amount of a compound according to Formula II:

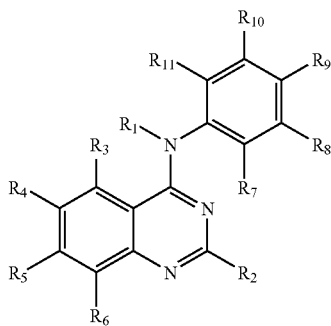

(II)

or a pharmaceutically acceptable salt or solvate thereof, wherein:

$R_1$ is $C_{1-2}$ alkyl, preferably $CH_3$;

$R_2$ is H; halo; $NHNH_2$, $N_3$; $C_{1-6}$ alkyl optionally substituted with OH or halo; $-OR_{23}$ or $-SR_{23}$ wherein $R_{23}$ is $C_{1-6}$ alkyl optionally substituted with OH or halo; $-CO_2C_{1-3}$ alkyl;+ or $-N(R^a)(R^b)$ wherein $R^a$ and $R^b$ are independently H, OH($R^a$ and $R^b$ are not both OH), $C_{1-3}$ alkyl, $C_{1-6}$ hydroxyalkyl, $C_{1-3}$ acyl, $C_{1-3}$ acyloxy, $(C=O)N(R^e)(R^f)$ or $C_{1-6}$ alkyl that is optionally substituted with $-N(R^e)(R^f)$ wherein $R^e$ and $R^f$ are independently H, OH($R^e$ and $R^f$ are not both OH), $C_{1-3}$ alkyl, or $C_{2-3}$ hydroxyalkyl, and wherein optionally $R^a$ and $R^b$ together with the nitrogen they both are linked to may form a 3, 4, 5 or 6-membered heterocycle;

$R_3$, $R_4$, $R_6$-$R_8$, $R_{10}$ and $R_{11}$ are independently $R_{16}$, $OR_{16}$, $SR_{16}$, $NR_{16}R_{17}$, or $NO_2$, wherein $R_{16}$ and $R_{17}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy);

$R_5$ is H, F, or $C_{1-3}$ alkyl, preferably H or F, and more preferably H; and $R_9$ is H; OH; halo; $N_3$; $C_{1-6}$ alkyl; $C_{1-6}$ haloalkyl $-OR_9$, wherein $R_{9a}$ is $C_{1-6}$ alkyl or $C_{1-6}$ haloalkyl; $-NH(R^a)$ or $-N(R^a)(R^b)$ where $R^a$ and $R^b$ are independently $C_{1-6}$ alkyl, $C_{1-6}$ acyl, $C_{1-6}$ acyloxy, amino, $-(C=O)N(R^c)(R^d)$ wherein $R^c$ and $R^d$ are independently H or $C_{1-6}$ alkyl; or $-COOR_{9b}$, wherein $R_{9b}$ is $C_{1-6}$ alkyl; optionally $R_9$ and one of $R_8$ and $R_{10}$ together form a 3, 4, 5, or 6-membered heterocycle; and any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy).

Preferably, $R_2$ is $-N(R^{50})C(=O)R_{40}$, $-N(R^{50})C(=O)N(R^{50})(R^{51})$, $-C(=O)N(R^{50})(R^{51})$, or $-OC(=O)N(R^{50})(R^{51})$; and preferably $R_9$ is $-N(R^{50})C(=O)R_{40}$, $-N(R^{50})C(=O)N(R^{50})(R^{51})$, $-C(=O)N(R^{50})(R^{51})$, or $-OC(=O)N(R^{50})(R^{51})$; wherein $R_{40}$ is selected from: H, $-OH$, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy and $C_{1-4}$ alkylthiol, wherein $R_{40}$ is optionally substituted with from one to three substituents independently selected from halo, $N_3$, nitro, hydroxy, thiol, CN, and $C_{1-4}$ alkyl, and preferably $R_{40}$ is $C_{1-4}$ alkyl optionally substituted by 1-3 F or Cl; and $R^{50}$ and $R^{51}$ are independently H, OH($R^{50}$ and $R^{51}$ are not both OH), $C_{1-4}$ alkyl, $C_{2-4}$ alkenyl, $C_{2-4}$ alkynyl, $C_{1-4}$ alkoxy, $C_{1-4}$ alkylthiol, $C_{2-4}$ alkenyloxy, $C_{2-4}$ alkynyloxy, $C_{1-4}$ haloalkyl, $C_{2-4}$ hydroxyalkyl, $C_{1-4}$ alkyl-O—$C_{1-4}$ alkyl-, or $R^{50}$ and $R^{51}$ together with the nitrogen atom to which they are both linked form a 3, 4, 5 or 6-membered heterocycle (e.g., piperidinyl, pyrrolidinyl, and morpholinyl) and preferably $R^{50}$ and $R^{51}$ are independently H or $C_{1-4}$ alkyl, said alkyl being optionally substituted with 1-3 F or Cl.

In other embodiments, $R_3$ is H; halo; $C_{1-3}$ alkyl; or $C_{1-3}$ alkoxy;

$R_4$ and $R_6$ are independently H; halo; $NO_2$, $N_3$; $C_{1-6}$ alkyl; $C_{1-3}$ alkoxy; or $-N(R_{2b})(R_{2c})$ wherein $R_{2b}$ and $R_{2c}$, are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with $-N(R_{2d})(R_{2e})$ wherein $R_{2d}$ and $R_{2e}$ are independently H, OH, $C_{1-3}$ alkyl or $C_{2-3}$ hydroxyalkyl, wherein $R_{2b}$ and $R_{2c}$ together may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_5$ is H or F;

$R_7$ and $R_{11}$ are independently H; halo; $CH_3$; or $OCH_3$; and $R_8$ and $R_{10}$ are independently H; halo; OH; $N_3$; $C_{1-3}$ alkyl; $C_{1-3}$ alkoxy; $C_{1-3}$ haloalkyl; —$OR_{9a}$, —$SR_{9a}$, where $R_{9a}$ is $C_{1-4}$ alkyl or $C_{1-3}$ haloalkyl; —NH($R^a$) or —N($R^a$)($R^b$) where $R^a$ and $R^b$ are independently $C_{1-3}$ alkyl; or —$COOR_{9b}$, wherein $R_{9b}$ is $C_{1-3}$ alkyl (preferably methyl or ethyl).

The methods of the present invention also comprise treating cells in vitro or a warm-blood animal, particularly mammal, more particularly a human with an effective amount of a compound according to Formula I:

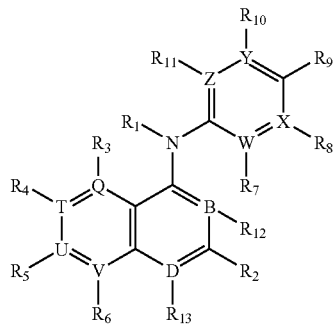

(I)

or a pharmaceutically acceptable salt or solvate thereof, wherein:

$R_1$ is $C_{1-6}$ alkyl, preferably methyl or ethyl, more preferably methyl;

$R_2$-$R_{13}$, are independently selected from:

(a) H, halo, $N_3$, nitro, hydroxy, thiol, and CN, (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, C(=$G^1$)$G^2R_{41}$ or -$G^3$C(=$G^1$)$G^2R_{41}$, (c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$)—C(=O)N($R^{52}$)($R^{53}$) OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C(=$G^1$)$G^2R_{43}$, or -$G^4$C(=G)$G^2R_{43}$, (d) —N($R^{50}$)($R^{51}$), —N($R^{50}$)C(=O)$R_{40}$, —N($R^{50}$)C(=O)N($R^{50}$)($R^{51}$), C(=O)N($R^{50}$)($R^{51}$)$_5$—OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$ ($R^{50}$)—, —C(=$G^1$)$G^2R_{41}$ or -$G^3$C(=$G^1$)$G^2R_{41}$, $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl, and preferably $R_{40}$ is $C_{1-4}$ alkyl optionally substituted by 1-3 F or Cl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle (e.g., piperidinyl, pyrrolidinyl, and morpholinyl), wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl, and preferably $R^{50}$ and $R^{51}$ are independently H or $C_{1-4}$ alkyl, said alkyl being optionally substituted with 1-3 F or Cl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

B, D, Q, T, U, V, W, X, Y and Z are independently C or N, provided that at least one of B and D is N and when B, D, Q, T, U, V, W, X, Y or Z is N then there is no substituent at the N; and wherein at least one of $R_2$-$R_{13}$ is $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{40}$, In specific embodiments, $R_2$ is $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$ wherein $R_{40}$, $R_{41}$, $R^{50}$, $G^1$, $G^2$, and $G^3$ are as defined immediately above. In specific embodiments, $R_9$ is $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$ wherein $R_{40}$, $R_{41}$, $R^{50}$, $G^1$, $G^2$, and $G^3$ are as defined immediately above.

Preferably, $R_9$ is selected from the group:

—$OR_{19}$, wherein $R_{19}$ is selected from the group of methyl, ethyl, fluoromethyl (e.g., $CH_2F$, $CHF_2$, $CF_3$), and fluoroethyl;

—$NHCH_3$;

—$N(CH_3)_2$;

—$N_3$;

—$COOR_{20}$; and

—NC(O)N($R_{21}$)($R_{22}$) or —NC(O)$R_{20}$ wherein $R_{20}$ is methyl or ethyl; and $R_{21}$ and $R_{22}$ are independently H, methyl or ethyl.

In preferred embodiments, $R_3$ is H; halo; $C_{1-3}$ alkyl; or $C_{1-3}$ alkoxy;

$R_4$ and $R_6$ are independently H; halo; $NO_2$, $N_3$; $C_{1-6}$ alkyl; $C_{1-3}$ alkoxy; or —N($R_{2b}$)($R_{2c}$) wherein $R_{2b}$ and $R_{2c}$ are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with —N($R_{2d}$)($R_{2e}$) wherein $R_{2d}$ and $R_{2e}$ are independently H, OH, $C_{1-3}$ alkyl or $C_{2-3}$ hydroxyalkyl, wherein $R_{2b}$ and $R_{2c}$, together may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_5$ is H or F;

$R_7$ and $R_{11}$ are independently H; halo; $CH_3$; or $OCH_3$; and $R_8$ and $R_{10}$ are independently H; halo; OH; $N_3$; $C_{1-3}$ alkyl; $C_{1-3}$ alkoxy; $C_{1-3}$ haloalkyl; —$OR_{9a}$, —$SR_{9a}$ where $R_{9a}$ is $C_{1-4}$ alkyl or $C_{1-3}$ haloalkyl; —NH(R) or —N($R^a$)($R^b$) where $R^a$ and $R^b$ are independently $C_{1-3}$ alkyl; or —$COOR_{9b}$, wherein $R_{9b}$ is $C_{1-3}$ alkyl (preferably methyl or ethyl).

Compounds of Formula I include compounds according to Formula II:

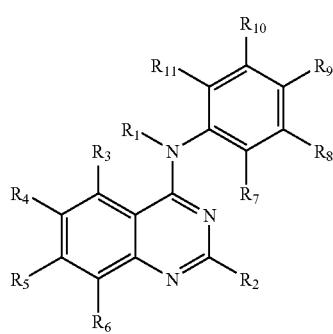

(II)

or pharmaceutically acceptable salts, or solvates thereof, wherein:

$R_1$ is $C_{1-6}$ alkyl, preferably methyl or ethyl, more preferably methyl;

$R_2$-$R_{11}$, are independently selected from:

(a) H, halo, $N_3$, nitro, hydroxy, thiol, and CN, (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—C(=$G^1$)$G^2$$R_{41}$ or -$G^3$C(=$G^1$)$G^2$$R_{41}$, (c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$)—C(=O)N($R^{52}$)($R^{53}$) OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C(=$G^1$)$G^2$$R_{43}$, or -$G^4$C(=$G^1$)$G^2$$R_{43}$ (d) —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2$$R_{41}$ or -$G^3$C(=$G^1$)$G^2$$R_{41}$.

$G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl, and preferably $R_{40}$ is $C_{1-4}$ alkyl optionally substituted by 1-3 F or Cl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle (e.g., piperidinyl, pyrrolidinyl, and morpholinyl), wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl, and preferably $R^{50}$ and $R^{51}$ are independently H or $C_{1-4}$ alkyl, said alkyl being optionally substituted with 1-3 F or Cl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and wherein at least one of $R_2$-$R_{11}$ is $R_{40}$C(=$G^1$)-, $R_{40}$C(=$G^1$)$G^2$-, $R_{40}$C(=$G^1$)$G^2$($R^{50}$)—, —C(=$G^1$)$G^2$$R_{41}$ or -$G^3$C(=$G^1$)$G^2$$R_{41}$.

In specific embodiments, $R_2$ is $R_{40}$C(=$G^1$)-, $R_{40}$C(=$G^1$)$G^2$-, $R_{40}$C(=$G^1$)$G^2$($R^{50}$)—, —C(=$G^1$)$G^2$$R_{41}$ or -$G^3$C(=$G^1$)

$G^2R_{41}$ wherein $R_{40}$, $R_{41}$, $R^{50}$, $G^1$, $G^2$, and $G^3$ are as defined immediately above. In specific embodiments, $R_9$ is $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$ wherein $R_{40}$, $R_{41}$, $R^{50}$, $G^1$, $G^2$, and $G^3$ are as defined immediately above.

Preferably, $R_9$ is selected from the group:
—$OR_{19}$, wherein $R_{19}$ is selected from the group of methyl, ethyl, fluoromethyl (e.g., $CH_2F$, $CHF_2$, $CF_3$), and fluoroethyl;
—$NHCH_3$;
—$N(CH_3)_2$;
—$N_3$;
—$COOR_{20}$; and
—$NC(O)N(R_{21})(R_{22})$ or —$NC(O)R_{20}$ wherein $R_{20}$ is methyl or ethyl; and $R_{21}$ and $R_{22}$ are independently H, methyl or ethyl.

In preferred embodiments,
$R_3$ is H; halo; $C_{1-3}$ alkyl; or $C_{1-3}$ alkoxy;
$R_4$ and $R_6$ are independently H; halo; $NO_2$, $N_3$; $C_{1-6}$ alkyl; $C_{1-3}$ alkoxy; or —$N(R_{2b})(R_{2c})$ wherein $R_{2b}$ and $R_{2c}$, are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with —$N(R_{2d})(R_{2e})$ wherein
$R_{2d}$ and $R_{2e}$ are independently H, OH, $C_{1-3}$ alkyl or $C_{2-3}$ hydroxyalkyl, wherein $R_{2b}$ and $R_{2c}$, together may form a 3, 4, 5 or 6-membered heterocycle (e.g., piperidinyl, pyrrolidinyl, and morpholinyl), and wherein $R_{2b}$ and $R_{2c}$, are not both OH, $R_{2d}$ and $R_{2e}$ are not both OH;
$R_5$ is H or F;
$R_7$ and $R_{11}$ are independently H; halo; $CH_3$; or $OCH_3$; and
$R_8$ and $R_{10}$ are independently H; halo; OH; $N_3$; $C_{1-3}$ alkyl; $C_{1-3}$ alkoxy; $C_{1-3}$ haloalkyl; —$OR_{9a}$, —$SR_{9a}$ where $R_{9a}$ is $C_{1-4}$ alkyl or $C_{1-3}$ haloalkyl; —$NH(R)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl).

The present invention also provides novel compounds, which are potent tubulin inhibitors, topoisomerase II inhibitors, caspase-3 activators and/or apoptosis inducers/promoters. Specifically, the novel compounds of the present invention are represented by Formulae I-II as defined above with the proviso that the compound is not $N^4$-methyl-$N^2$-(2-methyl-benzyl)-$N^4$-phenyl-quinazoline-2,4-diamine.

Novel compounds of the present invention include compounds represented by Formulae I-II as defined above with the proviso that when $R_2$ is methylbenzylamino, then $R_9$ is not H, and preferably is selected from the group:
—$OR_{19}$, wherein $R_{19}$ is selected from the group of methyl, ethyl, fluoromethyl (e.g., $CH_2F$, $CHF_2$, $CF_3$), and fluoroethyl;
—$NHCH_3$;
—$N(CH_3)_2$;
—$N_3$;
—$COOR_{20}$; and
—$NC(O)N(R_{21})(R_{22})$ or —$NC(O)R_{20}$ wherein $R_{20}$ is methyl or ethyl; and $R_{21}$ and $R_{22}$ are independently H, methyl or ethyl.

Among all the compounds of the present invention as disclosed above, preferred are those that can induce caspase activation as determined by the method and under conditions (measurement at 24 hours) described in Example 43, preferably at an $EC_{50}$ of no greater than about 1,000 nM, more preferably at an $EC_{50}$ of no greater than about 500 nM, more preferably at an $EC_{50}$ of no greater than about 200 nM, even more preferably at an $EC_{50}$ of no greater than about 100 nM, and most preferably at an $EC_{50}$ of no greater than about 10 nM. Also preferred compounds are those of Formulae I-II, and pharmaceutically acceptable salts or solvates thereof, that are able to inhibit tubulin at an $IC_{50}$ of no greater than about 2,000 nM, preferably no greater than about 1,000 nM, more preferably less than about 500 nM, as determined by the method and under conditions described in Example 44.

Exemplary compounds of the present invention are compounds provided in Examples 1-42, and pharmaceutically acceptable salts or prodrugs thereof. Specific exemplary compounds include but are not limited to:
(4-Acetamido-phenyl)-(2-methyl-quinazolin-4-yl)-methylamine;
(2-Benzylamino-quinazolin-4-yl)-(4-methoxyphenyl)-methylamine;
(2-Methyl-quinazolin-4-yl)-(4-methoxycarbonylamino-phenyl)-methylamine;
(2-Methyl-quinazolin-4-yl)-(4-ureido-phenyl)-methylamine;
(2-Methyl-quinazolin-4-yl)-(N-methyl-4-acetamido-phenyl)-methylamine;
(2-Methyl-quinazolin-4-yl)-(4-methylamino-phenyl)-methylamine;
(2-Methyl-quinazolin-4-yl)-[4-(N-methyl-methoxycarbonylamino)-phenyl]-methylamine;
[2-(4-Methoxy-benzylamino)-quinazolin-4-yl)]-(4-methoxyphenyl)-methylamine;
(2-Methyl-6-nitroquinazolin-4-yl)-(4-dimethylaminophenyl)-methylamine;
(2-Chloro-6-nitroquinazolin-4-yl)-(4-methoxyphenyl)-methylamine;
(6-Amino-2-methyl-quinazolin-4-yl)-(4-dimethylaminophenyl)-methylamine;
(2-Chloro-quinazolin-4-yl)-(4-dimethylaminophenyl)-methylamine;
(2-Dimethylamino-6-nitroquinazolin-4-yl)-(4-methoxyphenyl)-methylamine;
(2-Methylamino-quinazolin-4-yl)-(4-dimethylaminophenyl)-methylamine;
[2-(N-Methyl-acetamido)-quinazolin-4-yl]-(4-dimethylaminophenyl)-methylamine;
(2-Methylamino-6-nitroquinazolin-4-yl)-(4-methoxyphenyl)-methylamine;
(6-Amino-2-dimethylamino-quinazolin-4-yl)-(4-methoxyphenyl)-methylamine;
(6-Amino-2-methylamino-quinazolin-4-yl)-(4-methoxyphenyl)-methylamine;
(4-Methylthio-phenyl)-(2-methyl-quinazolin-4-yl)-methylamine;
(3,4-Dimethoxy-phenyl)-(2-methyl-quinazolin-4-yl)-methylamine;
(2-Dimethylamino-pyridine-5-yl)-(2-methyl-quinazolin-4-yl)-methylamine;
(4-Methoxy-phenyl)-(2-N-methylacetamido-quinazolin-4-yl)-methylamine;
(4-Methoxy-phenyl)-(2-N-methyl-methoxycarbonylamino-quinazolin-4-yl)-methylamine;
(6-Dimethylamino-2-methyl-quinazolin-4-yl)-(4-methoxyphenyl)-methylamine;
(6-Acetamido-2-methyl-quinazolin-4-yl)-(4-methoxy-phenyl)-methylamine;
(2-Hydrazinyl-quinazolin-4-yl)-(4-methoxy-phenyl)-methylamine;
(6-methoxycarbonylamino-2-methyl-quinazolin-4-yl)-(4-methoxy-phenyl)-methylamine;
(3,4-Dimethoxy-phenyl)-(2-methyl-6-nitro-quinazolin-4-yl)-methylamine;
(6-N-methyl-acetamido-2-methyl-quinazolin-4-yl)-(4-methoxy-phenyl)-methylamine;

(2-Acetamido-quinazolin-4-yl)-(4-methoxy-phenyl)-methylamine;

N-{4-[Methyl(2-methylquinazolin-4-yl)amino]phenyl}formamide;

and pharmaceutically acceptable salts or prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, which may be optionally substituted. Alkoxy substituents include, without limitation, halo, morpholino, amino including alkylamino and dialkylamino, and carboxy including esters thereof.

Useful alkylthio groups include sulfur substituted by one of the $C_{1-10}$ alkyl groups mentioned above, which may be optionally substituted. Also included are the sulfoxides and sulfones of such alkylthio groups.

Useful amino groups include $-NH_2$, $-NHR_x$ and $-NR_xR_y$, wherein $R_x$ and $R_y$ are $C_{1-10}$ alkyl or cycloalkyl groups, or $R_x$ and $R_y$ are combined with the N to form a ring structure, such as a piperidine, or $R_x$ and $R_y$ are combined with the N and other group to form a ring, such as a piperazine. The alkyl group may be optionally substituted.

Optional substituents on the alkyl, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carboxy or $C_{1-2}$ alkylenedioxy (e.g., methylenedioxy).

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon or on a nitrogen atom if the resulting compound is stable, including an oxo substituent ("=O") wherein two hydrogen atoms are replaced.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, 13-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I-II can be prepared as illustrated by the exemplary reaction in Scheme 1. Reaction of optionally substituted quinazoline-2,4-dione with phosphorylchloride produces the corresponding 2,4-dichloroquinazoline, which is reacted with an optionally substituted aniline, such as N-methyl-4-methoxy-aniline, to produce the substituted 2-chloro-4-anilino-quinazoline.

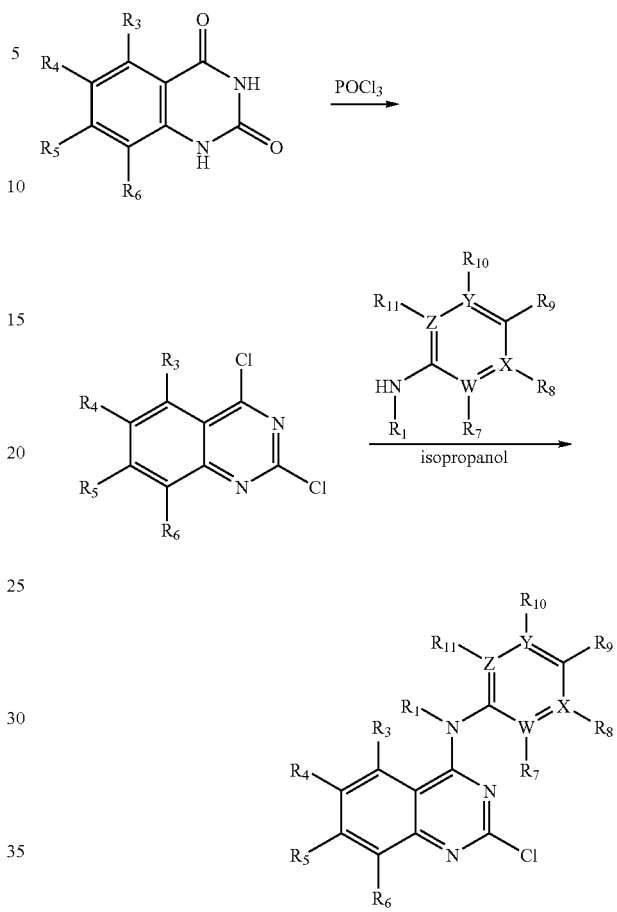

Compounds of this invention with Formulae I-II also could be prepared as illustrated by the exemplary reaction in Scheme 2. Reaction of the substituted 2-chloro-4-anilino-quinazoline with a nucleophile ($R_2$), such as hydroxylamine, in isopropanol heated by microwave irradiation produces the 2-substituted 4-anilino-quinazoline, such as 2-hydroxyamino-4-anilino-quinazoline. Other nucleophiles that can be used in the reaction include NaOMe, $NaN_3$, NaSMe, $NH_3$, $NH_2Me$, or $NHMe_2$, and the reaction can be run at room temperature or elevated temperature.

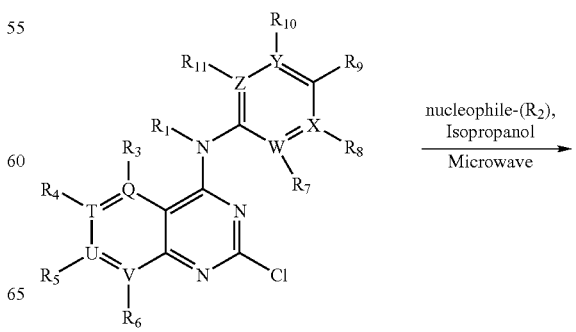

-continued

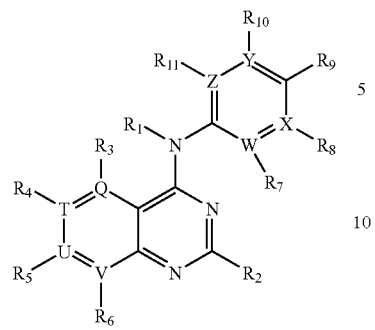

Compounds of this invention with Formulae I-II, could be prepared as illustrated by the exemplary reaction in Scheme 3. Reaction of 2,4-dichloroquinazoline with a substituted arylamine or heteroarylamine, such as a substituted pyridin-3-ylamine, produces the corresponding 4-aryl/heteroarylamino substituted 2-chloro-quinazoline, which is alkylated with a haloalkyl, such as methylated by reaction with methyl iodide in the presence of a base such as NaH, to produce the corresponding 4-N-methyl-aryl/heteroaryl-amino substituted 2-chloro-quinazoline.

-continued

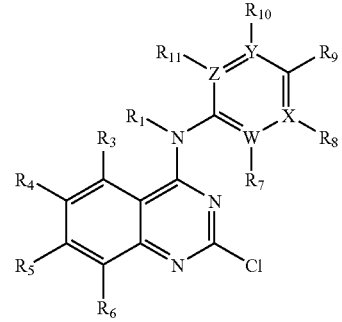

Alternatively, compounds of this invention with Formulae I-II also could be prepared as illustrated by the exemplary reaction in Scheme 4. The N-alkyl-arylamine or N-alkyl-heteroarylamine could be prepared by reaction of the arylamine or heteroarylamine with a ketone or aldehyde, such as acetone, in the presence of a reducing agent, such as NaCNBH₃. The N-alkyl-arylamine or N-alkyl-heteroarylamine is then reacted with optionally substituted 2,4-dichloroquinazoline to produce the corresponding 4-substituted 2-chloro-quinazoline.

Scheme 3

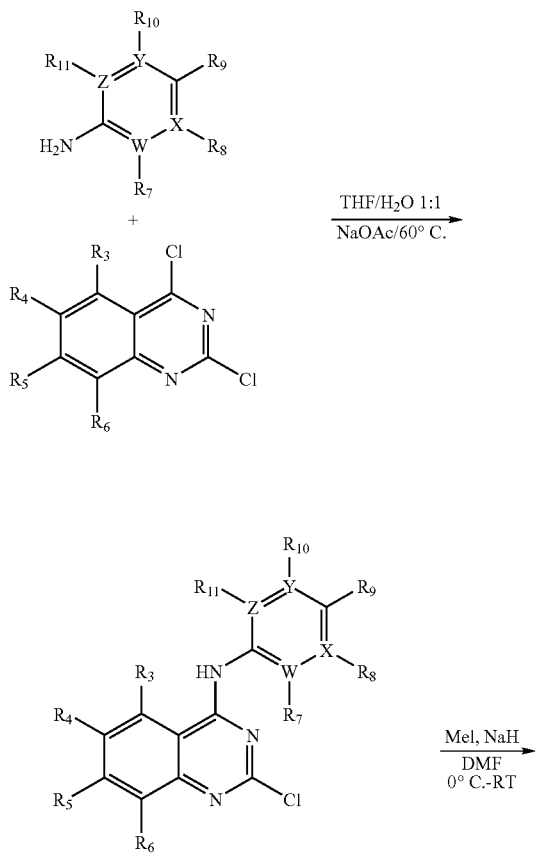

Scheme 4

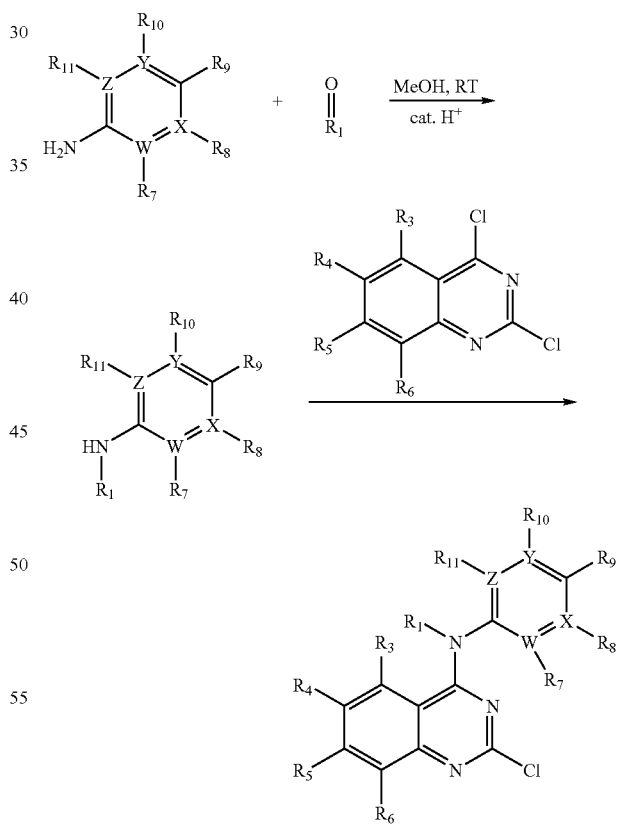

Compounds of this invention with Formulae I-II also could be prepared as illustrated by the exemplary reaction in Scheme 5. Reaction of optionally substituted 2-amino-benzoic acid, such as 2-amino-5-methyl-benzoic acid, with potassium cyanate in the presence of an acid, such as acetic acid, produces the corresponding optionally substituted quinazoline-2,4-dione, such as 6-methyl-quinazoline-2,4-dione, which is converted to the corresponding optionally substituted 2,4-dichloroquinazoline, such as 6-methyl-2,4-dichloroquinazoline by reaction with phosphorylchloride. Reaction of optionally substituted 2,4-dichloroquinazoline, such as 6-methyl-2,4-dichloroquinazoline with a substituted arylamine or heteroarylamine, such as N-methyl-4-methoxy-aniline, produces the corresponding 4-substituted 2-chloro-quinazoline, such as substituted 2-chloro-4-anilino-quinazoline.

reaction with phosphorylchloride. Reaction of 2-substituted 4-chloro-quinazoline, such as 4-chloro-2-fluoromethyl-quinazoline with a substituted aniline, such as N-methyl-4-methoxy-aniline, produces the corresponding 2-substituted 4-anilino-quinazoline, such as 2-fluoromethyl-4-anilino-quinazoline. Other substituted acetonitriles that can be used for the reaction include chloro-acetonitrile and bromo-acetonitrile, as well as acetonitrile and propionitrile.

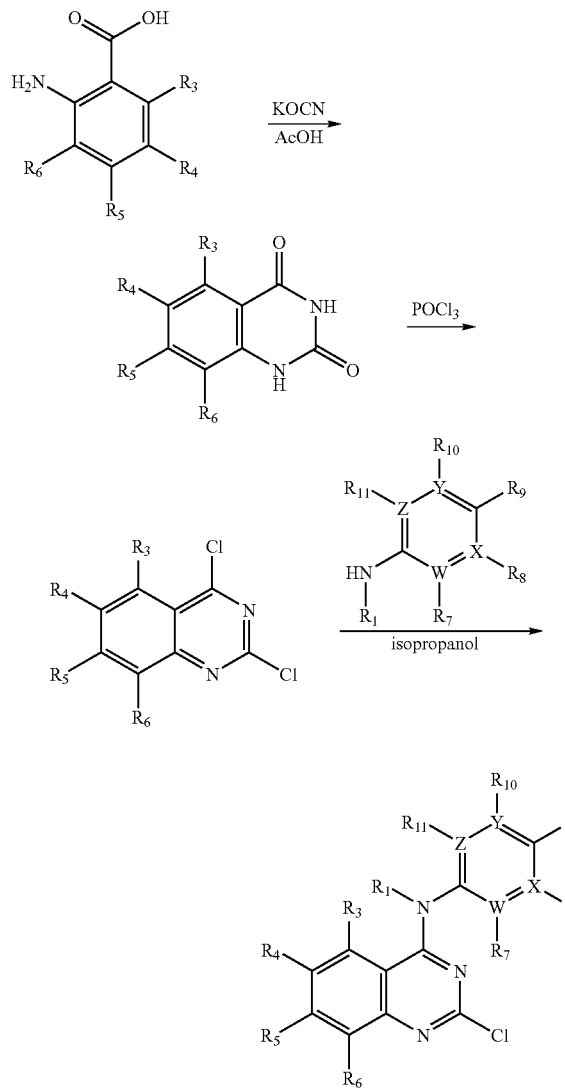

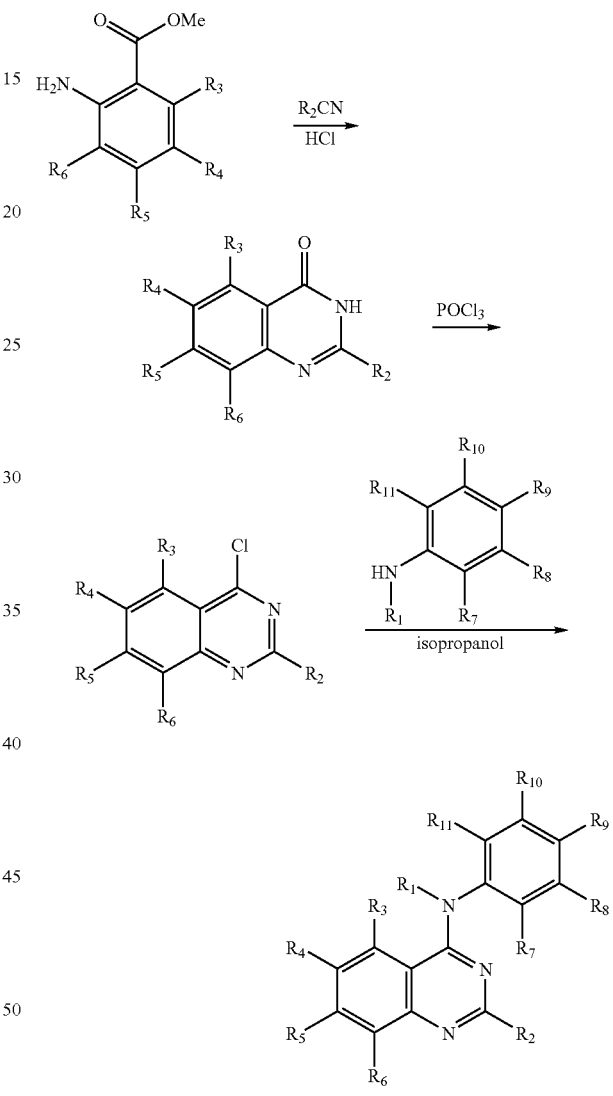

Compounds of this invention with Formulae I-II, wherein $R_2$ is an optionally substituted alkyl group, could be prepared as illustrated by the exemplary reaction in Scheme 6. Reaction of 2-amino-benzoic acid methyl ester with an optionally substituted acetonitrile, such as fluoro-acetonitrile, in the presence of HCl produces the corresponding 2-substituted quinazoline-4(3H)-one, such as 2-fluoromethyl-quinazoline-4(3H)-one, which is converted to 2-substituted 4-chloro-quinazoline, such as 4-chloro-2-fluoromethyl-quinazoline by Compounds of this invention with Formulae I-II, wherein $R_2$ is a substituted alkyl group, could also be prepared as illustrated by the exemplary reaction in Scheme 7. Reaction of a substituted 2-chloroalkyl-4-(N-alkyl-arylamine or N-alkyl-heteroarylamine)-quinazoline, such as N-methyl-2-chloromethyl-4-anilino-quinazoline, with a nucleophile, such as $NHMe_2$, produces the substituted 2-dimethylaminomethyl-4-anilino-quinazoline. Other nucleophiles that can be used in the reaction include $NaOMe$, $NaN_3$, $NaSMe$, $NH_3$, $NH_2Me$, or $NHMe_2$, and the reaction can be run at room temperature and elevated temperature.

Scheme 7

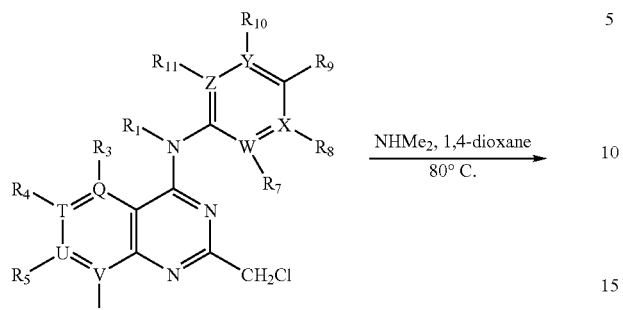

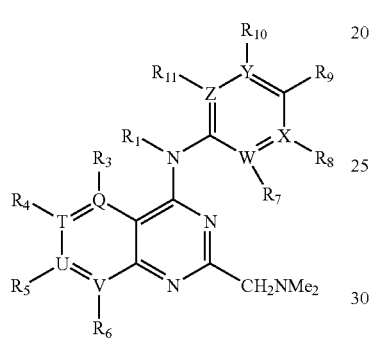

Compounds of this invention with Formulae I-II, wherein $R_1$ is a substituted alkyl, could be prepared as illustrated by the exemplary reaction in Scheme 8. For example, reaction of an optionally substituted 4-(arylamine or heteroarylamine)-quinazoline, such as 2-methyl-4-(6-methoxy-pyridin-3-ylamino)-quinazoline, with a substituted haloalkyl, such as difluoromethyl chloride, in the presence of a base such as NaH, produces the corresponding 4-(N-alkyl-arylamine or N-alkyl-heteroarylamine)-quinazoline, such as 2-methyl-$N^4$-difluoromethyl-4-(4-methoxy-pyridin-3-ylamino)-quinazoline.

Scheme 8

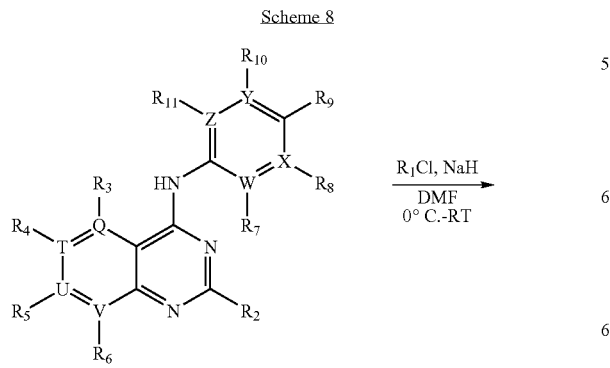

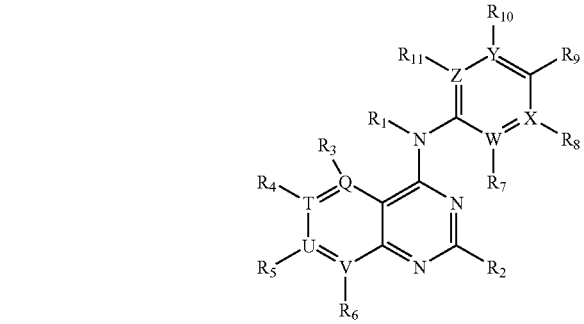

Compounds of this invention with Formulae I-II, wherein $R_2$ is an alkyl group, could be prepared as illustrated by the exemplary reaction in Scheme 9. Reaction of a substituted 2-amino-benzoic acid, such as 2-amino-5-nitro-benzoic acid, with acetic anhydride, produces the corresponding substituted 2-methyl-4H-benzo[d][1,3]oxazine-4-one, such as 2-methyl-6-nitro-4H-benzo[d][1,3]oxazine-4-one, which is converted to the corresponding quinazoline-4(3H)-one, such as 2-methyl-6-nitro-quinazoline-4(3H)-one, by treatment with ammonia in dioxane. The compound is then converted to the corresponding 4-chloro-quinazoline, such as 4-chloro-2-methyl-6-nitro-quinazoline by reaction with phosphorylchloride. Reaction of the 4-chloro-quinazoline, such as 4-chloro-2-methyl-6-nitro-quinazoline with a substituted arylamine or heteroarylamine, such as N-methyl-4-methoxy-aniline, produces the corresponding 4-(arylamino or heteroarylamino)-quinazoline, such as substituted 2-methyl-6-nitro-4-anilino-quinazoline. Other substituted 2-amino-benzoic acid that can be used for the reaction include 2-amino-4-nitro-benzoic acid, 2-amino-5-chloro-benzoic acid.

Scheme 9

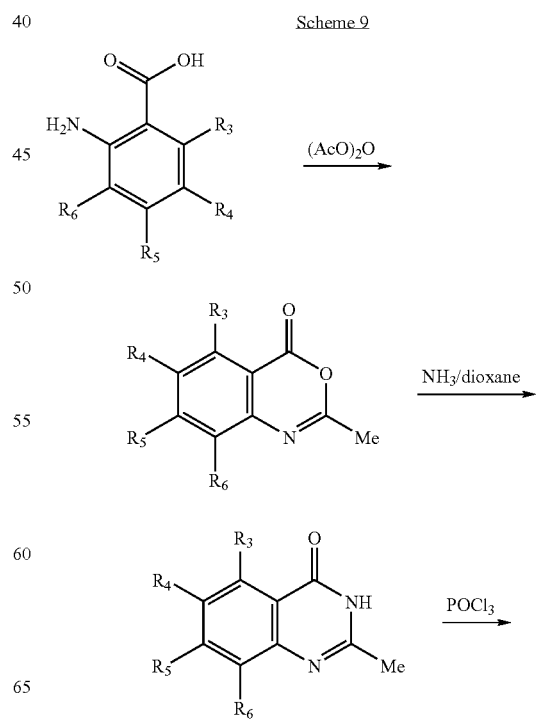

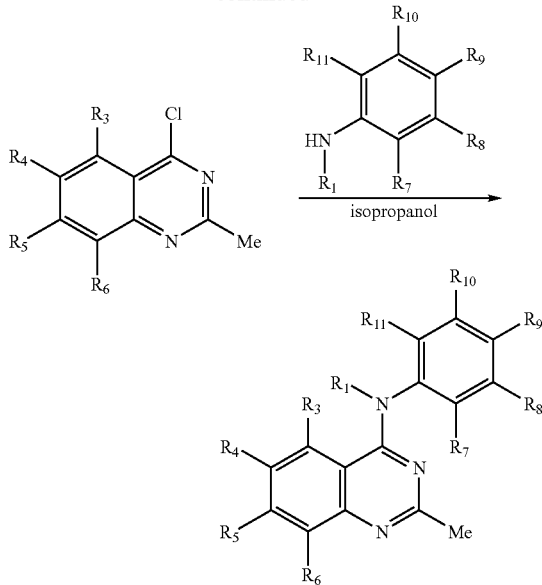

Compounds substituted with a nitro group can be reduced by hydrogenation under H₂ with Pd to produce the amino compound, which can be converted to the azido compounds by diazotization followed by treatment with NaN₃.

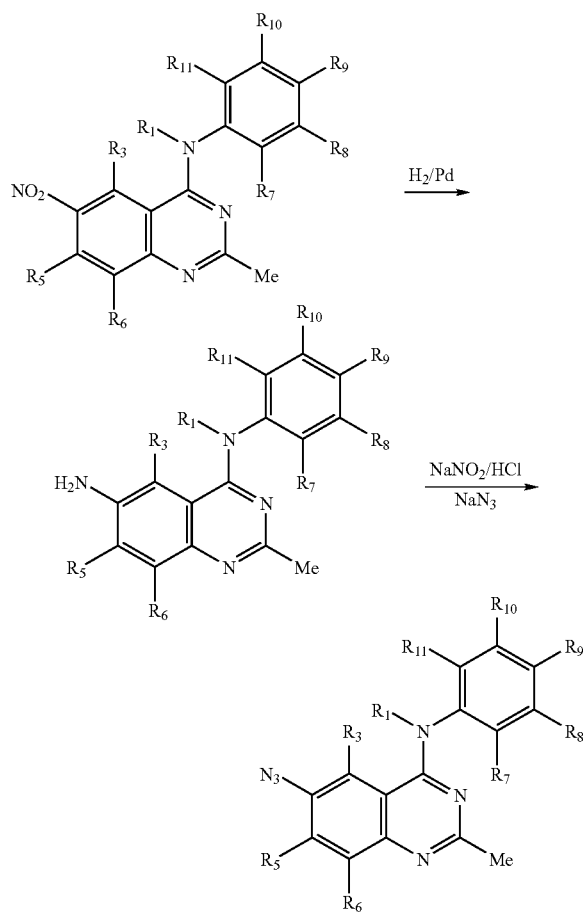

Compounds of this invention with Formulae I-II, , could be prepared as illustrated by the exemplary reaction in Scheme 10. Reaction of an amino-nicotinic acid, such as 2-amino-nicotinic acid, with acetyl chloride, in the presence of base, such as triethylamine, produces the corresponding amide, which is treated with ammonium acetate to produce the corresponding 2-methyl-pyrido[2,3-d](heteroaryl or heterocycle)-4-ol, such as 2-methyl-pyrido[2,3-d]pyrimidin-4-ol. The resulting compound is then converted to the corresponding 4-chloro-2-methyl-pyrido[2,3-d](heteroaryl or heterocycle), such as 4-chloro-2-methyl-pyrido[2,3-d]pyrimidine by reaction with phosphorylchloride, which is treated with an optionally substituted arylamino or heteroarylamino, such as N-methyl-4-methoxy-aniline to produce the corresponding optionally substituted 4-(arylamino or heteroarylamino)-2-methyl-pyrido[2,3-d](heteroaryl or heterocycle), such as substituted 4-anilino-2-methyl-pyrido[2,3-d]pyrimidine.

Scheme 10

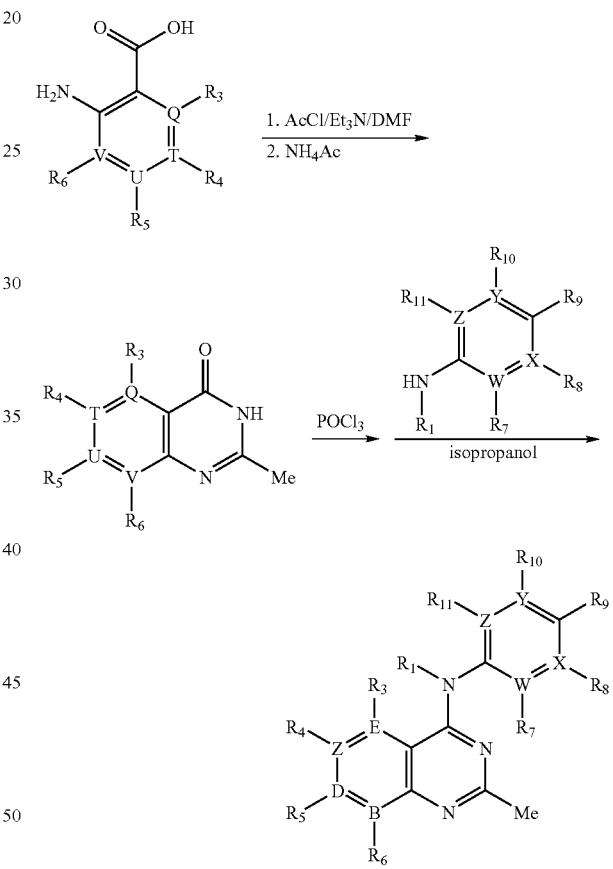

Additional exemplary compounds may be synthesized according to the synthesis schemes below:

Scheme 11

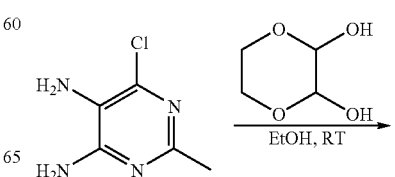

35
-continued
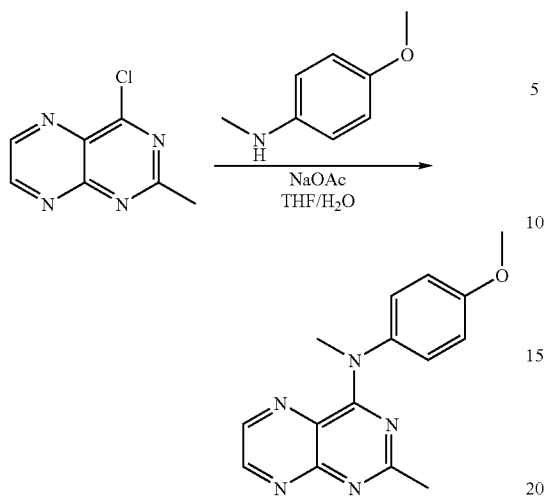
36
-continued
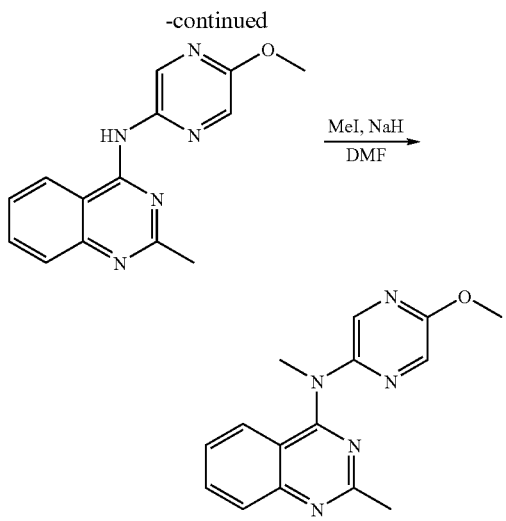
Scheme 12
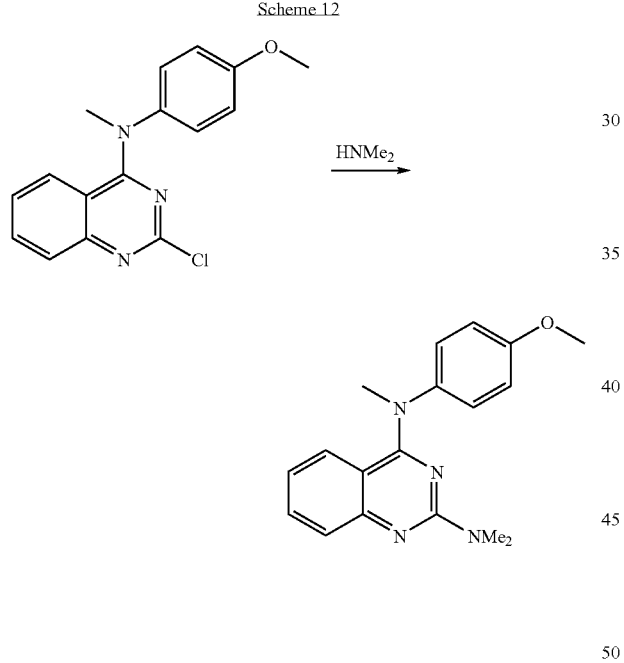
Scheme 14
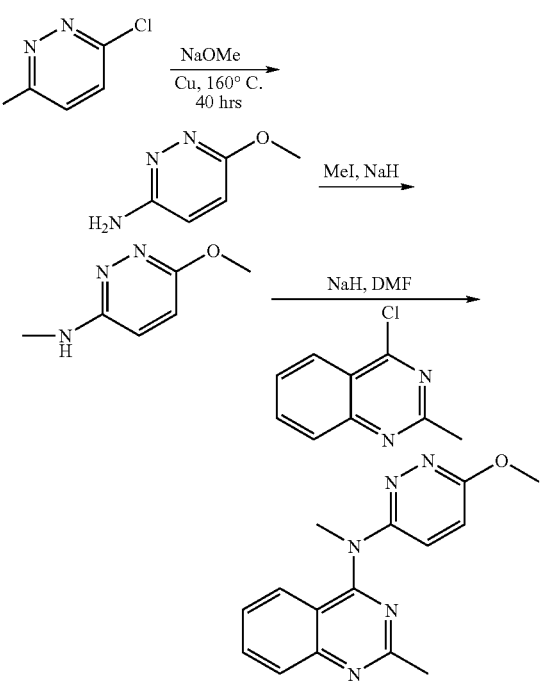
Scheme 13
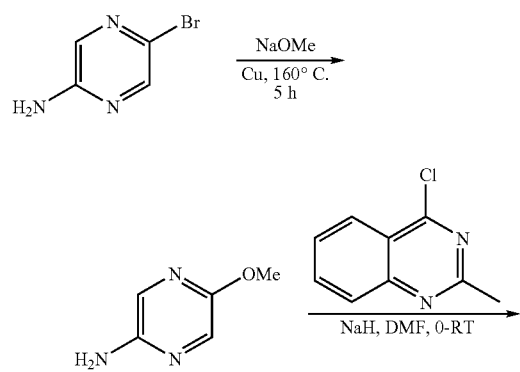
Scheme 15
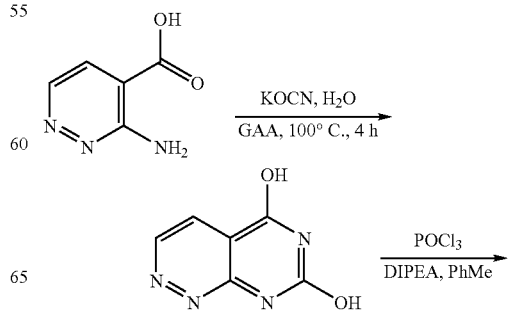

-continued
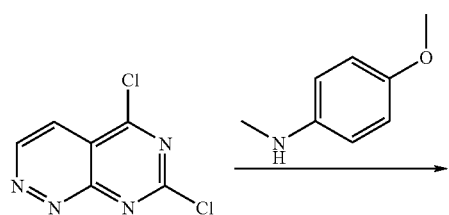
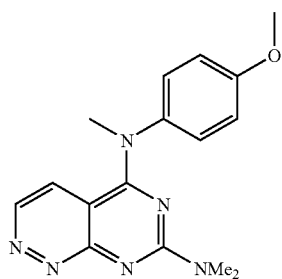
Scheme 17
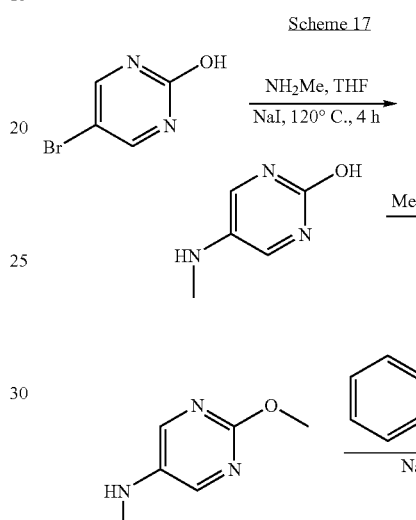
Scheme 16
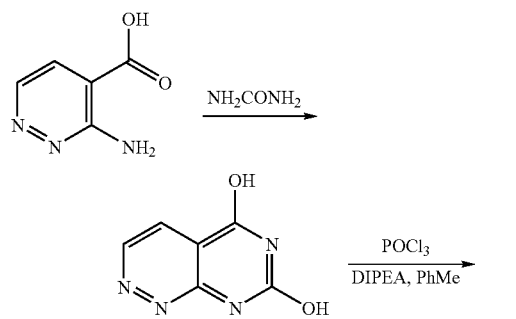
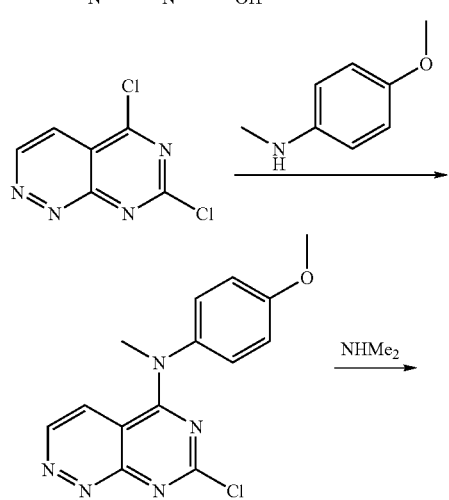
Scheme 18
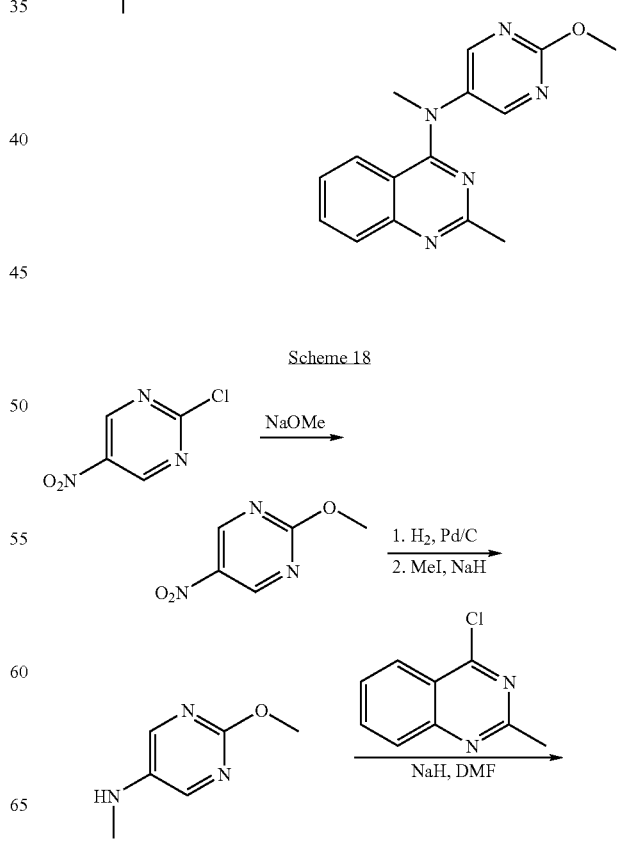

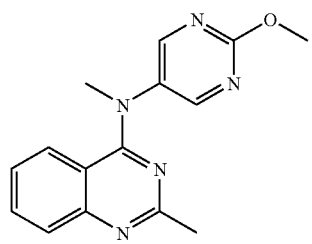
5
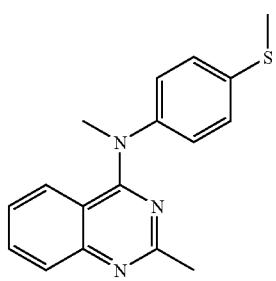
Scheme 19
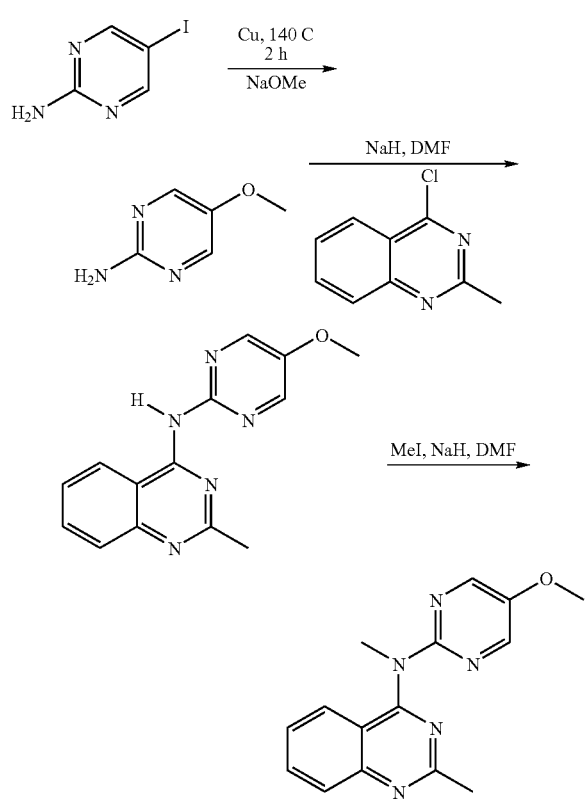
Scheme 20
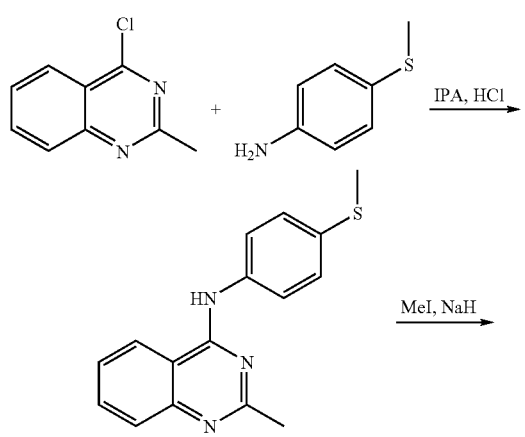
Scheme 21
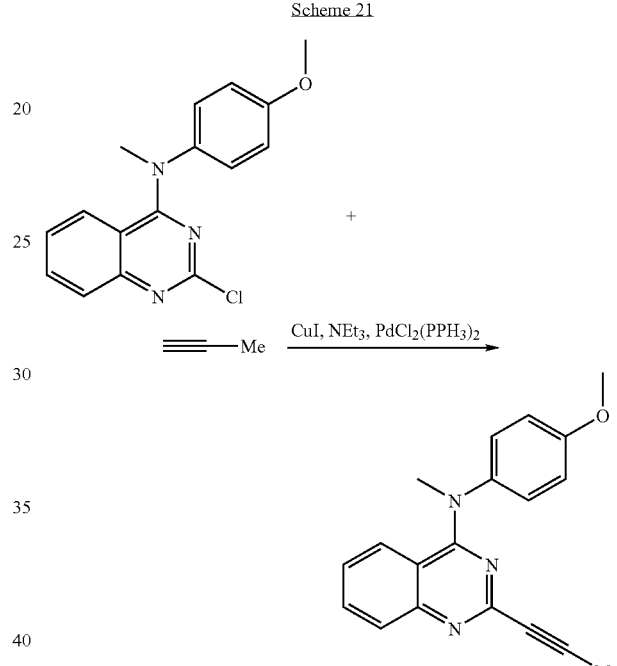
Scheme 22
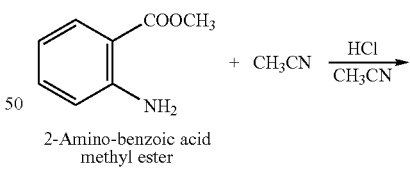
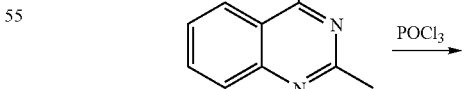
2-Methyl-quinazolin-4-ol
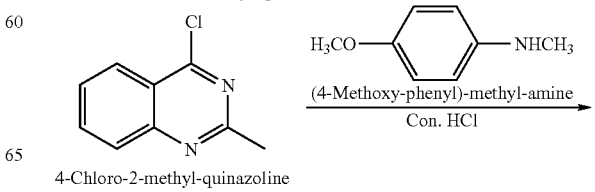
4-Chloro-2-methyl-quinazoline

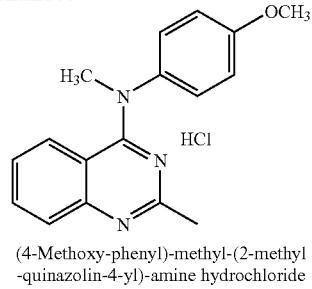

(4-Methoxy-phenyl)-methyl-(2-methyl-quinazolin-4-yl)-amine hydrochloride

An important aspect of the present invention is the discovery that compounds having Formulae I-II are activators of caspases and inducers of apoptosis. Another important aspect of the invention is that compounds having Formulae I-II are inhibitors of tubulin polymerization. Therefore, these compounds are useful in treating diseases that are responsive to activating caspases, inducing apoptosis, or inhibiting tubulin. For example, these compounds are useful in a variety of clinical conditions in which there is uncontrolled cell growth and spread of abnormal cells, such as in the case of cancer.

The present invention also includes a therapeutic method comprising administering to an animal an effective amount of a compound, or a pharmaceutically acceptable salt or prodrug of said compound of Formulae I-II, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

Another aspect of the present invention is to provide a pharmaceutical composition, containing an effective amount of a compound of Formulae I-II, or a pharmaceutically acceptable salt of said compound, in admixture with one or more pharmaceutically acceptable carriers or diluents.

In one embodiment, a pharmaceutical composition comprising a compound of Formulae I-II disclosed herein, or a pharmaceutically acceptable salt of said compound, in combination with a pharmaceutically acceptable vehicle is provided.

Preferred pharmaceutical compositions comprise compounds of Formulae I-II, and pharmaceutically acceptable salts, esters, or prodrugs thereof, that are able to induce caspase activation as determined by the method described in Example 186, preferably at an $EC_{50}$ no greater than 1,000 nM, more preferably at an $EC_{50}$ no greater than 500 nM, more preferably at an $EC_{50}$ no greater than 200 nM, more preferably at an $EC_{50}$ no greater than 100, and most preferably at an $EC_{50}$ no greater than 10 nM. Other preferred compositions comprise compounds of Formulae I-II, and pharmaceutically acceptable salts, esters, or prodrugs thereof, that are able to inhibit tubulin polymerization as determined by the method described in Example 188.

Another embodiment of the present invention is directed to a composition effective to inhibit neoplasia comprising a compound, or a pharmaceutically acceptable salt or prodrug of said compound of Formulae I-II, which functions as a caspase cascade activator and inducer of apoptosis or inhibitor of tubulin polymerization, in combination with at least one known cancer chemotherapeutic agent, or a pharmaceutically acceptable salt of said agent. Examples of known cancer chemotherapeutic agents which may be used for combination therapy include, but not are limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; EGFR inhibitors, such as Iressa® (gefitinib) and Tarceva® (erlotinib); proteosome inhibitors; antibodies, such as campath, Herceptin® (trastuzumab), Avastin® (bevacizumab), or Rituxan® (rituximab). Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

It has been reported that alpha-1-adrenoceptor antagonists, such as doxazosin, terazosin, and tamsulosin can inhibit the growth of prostate cancer cell via induction of apoptosis (Kyprianou, N., et al., *Cancer Res* 60:4550-4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known alpha-1-adrenoceptor antagonist, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., *Cancer Res.* 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., *Cancer Res.* 62:313-322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known sigma-2 receptor agonist, or a pharmaceutically acceptable salt of said agonist. Examples of known sigma-2 receptor agonists which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., *Int. J. Cancer* 97:746-750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., *Nat. Med.* 8:225-232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., *Cancer Chemother. Pharmacol.* 43:145-150 (1999)). 4HPR also was reported to have good activity in combination with gamma-radiation on bladder cancer cell lines (Zou, C., et al., *Int. J. Oncol.* 13:1037-1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433-443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as ST1571 (Gleevec® (imatinib mesylate)), have potent synergetic effect in combination with other anti-leukemic agents, such as etoposide (Liu, W. M., et al. *Br. J. Cancer* 86:1472-1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known tyrosine kinase inhibitor, or a pharmaceutically acceptable salt of said agent. Examples of known tyrosine kinase inhibitors, which can be used for combination therapy include, but are not limited to, Gleevec® (imatinib mesylate), ZD1839 Iressa® (gefitinib), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544-3550 (2001)). Synergy of the protein farnesyltransferase inhibitor SCH66336 and cisplatin in human cancer cell lines also has been reported (Adjei, A. A., et al., *Clin. Cancer. Res.* 7:1438-1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778, 123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209-4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known cyclin-dependent kinase inhibitor, or a pharmaceutically acceptable salt of said agent. Examples of known cyclin-dependent kinase inhibitors, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology* (*Huntingt*) 16(No. 4 Suppl. 3):17-21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known COX-2 inhibitor, or a pharmaceutically acceptable salt of said inhibitor. Examples of known COX-2 inhibitors which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis or inhibitor of tubulin polymerization, in bioconjugation with at least one known therapeutically useful antibody, such as Herceptin® (trastuzumab) or Rituxan® (rituximab), growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® (trastuzumab) or Rituxan® (rituximab).

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis or inhibitor of tubulin polymerization. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al, *Int. J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al, (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-II, which functions as a caspase cascade activator and inducer of apoptosis, is an effective treatment for autoimmune diseases.

Psoriasis is a chronic skin disease that is characterized by scaly red patches. Psoralen plus ultraviolet A (PUVA) is a widely used and effective treatment for psoriasis vulgarism Coven, et al., *Photodermatol. Photoimmunol. Photomed.* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-II, which functions as a caspase cascade activator and inducer of apoptosis, is an effective treatment for hyperproliferative skin diseases, such as psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-II, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-II, which functions as a caspase cascade activator and inducer of apoptosis, is an effective treatment for inflammation.

Caspase cascade activators and inducers of apoptosis may also be a desirable therapy in the elimination of pathogens, such as HIV, Hepatitis C and other viral pathogens. The long lasting quiescence, followed by disease progression, may be explained by an anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis serves as a beneficial host mechanism to limit the spread of HIV and new therapeutics using caspase/apoptosis activators are useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656-64 (2000)). Therefore, apoptosis inducers are useful as therapeutics for HIV, HCV, HBV, and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, are useful as therapeutics for the prevention or reduction of in-stent restenosis.

Another important aspect of the present invention is that compounds of the present invention are potent and highly efficacious activators of caspase-3, inhibitors of tubulin polymerization, and inhibitors of topoisomerase even in drug resistant cancer cells, which enables these compounds to inhibit the growth and proliferation of drug resistant cancer cells, and to cause apoptosis and cell death in the drug resistant cancer cells. Specifically, the compounds of the present invention are not substrates for the MDR transporters such as Pgp-1 (MDR-1), MRP-1 and BCRP. This is particularly surprising in view of the fact that almost all of the commercially available tubulin-interacting chemotherapeutics are substrates for multidrug resistance transporters (MDRs).

Multidrug resistance is the major cause of chemotherapy failure. Drug resistance is typically caused by ATP-dependent efflux of drug from cells by ATP-binding cassette (ABC) transporters. In particular, the ABC transporters ABCB1 (MDR-1, P glycoprotein); ABCC1 (MRP1); and ABCG2 (BCRP, MXR) are typically over-expressed in drug resistant tumors and thus are implicated in drug resistance. In comparison to most standard anti-cancer drugs, which are not effective in killing drug resistant cancer cells, the compounds of the present invention are effective in killing drug resistant cancer cells. Therefore, compounds of this invention are useful for the treatment of drug resistant cancer.

Thus, another aspect of the present invention is the application of the methods and compounds of the present invention as described above to tumors that have acquired resistance to other anticancer drugs. In one embodiment, a compound of the present invention is administered to a cancer patient who has been treated with another anti-cancer drug. In another embodiment, a compound of the present invention is administered to a patient who has been treated with and is not responsive to another anti-cancer drug or developed resistance to such other anti-cancer compound. In another embodiment, a compound of the present invention is administered to a patient who has been treated with another anti-cancer drug and is refractory to said other anti-cancer drug. The compounds of the present invention can be used in treating cancer in a patient who is not responsive or is resistant to any other anti-cancer agent. Examples of such other anti-cancer agent may include alkylating agents, antimitotic agents, topo I inhibitors, topo II inhibitors, RNA/DNA antimetabolites, EGFR inhibitors, angiogenesis inhibitors, tubulin inhibitors (e.g., vinblastine, Taxol® (paclitaxel), and analogues thereof), proteosome inhibitors, etc., some of the exemplary compounds of which are provided above and are general known in the art, e.g., melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine. The compounds can be used in treating patients having any type of diseases responsive to the inhibition of tubulin or inhibition of topoisomerase (including but not limited to the types of cancer described above) who are not responsive or become resistant to another therapeutic agent, e.g., another anti-cancer agent.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. For intramuscular injection, the dose is generally approximately one-half of the oral dose. For example, a suitable intramuscular dose would be approximately 0.0025 to approximately 25 mg/kg of body weight, and most preferably, from approximately 0.01 to approximately 5 mg/kg of body weight. If a known cancer chemotherapeutic agent is also administered, it is administered in an amount that is effective to achieve its intended purpose. The amounts of such known cancer chemotherapeutic agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 10 mg, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, and also preparations that may be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxy-propymethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which may be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

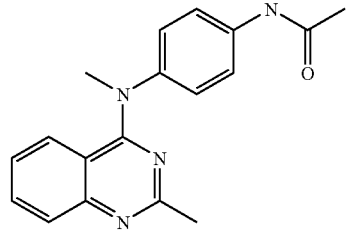

(4-Acetamido-phenyl)-(2-methyl-quinazolin-4-yl)-methylamine

To a solution of (4-amino-phenyl)-(2-methyl-quinazolin-4-yl)-methylamine (28 mg, 0.11 mmol) in 2 mL of dichloromethane with triethylamine (50 uL, 0.36 mmol) cooled at 0° C. was added acetic anhydride (50 uL, 0.53 mmol), followed by a few crystals of 4-dimethylaminopyridine, and the mixture was allowed to warm to room temperature. The reaction mixture was stirred for 0.5 h and 25 mL of ethyl acetate was added. The solution was washed with saturated $NaHCO_3$, dried over anhydrous $Na_2SO_4$, filtered and concentrated. The crude was purified by column chromatography (80% ethyl acetate/hexane) to give the title compound (32.5 mg, 0.11 mmol, 100%). $^1$H NMR ($CDCl_3$): 7.75 (d, J=8.1, 1H), 7.5-7.57 (m, 3H), 6.94-7.12 (m, 4H), 3.60 (s, 3H), 2.72 (s, 3H), 2.42 (s, 3H).

Example 2

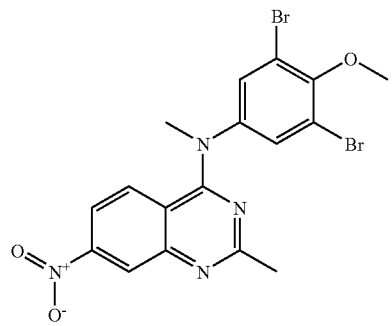

(3,5-Dibromo-4-methoxyphenyl)-(2-methyl-7-nitro-quinazolin-4-yl)-methylamine

A mixture of 4-chloro-2-methyl-7-nitro-quinazolinone (75 mg, 0.34 mmol), and 3,5-dibromo-4-methoxy-N-methylbenzenamine (112 mg, 0.38 mmol) and sodium acetate (55 mg, 0.67 mmol) in 4 mL of solvent (THF:water/1:1), was stirred at 75° C. for 6 h. The reaction mixture was diluted with 25 mL of ethyl acetate and washed with saturated NaCl, organic layer dried over anhydrous $MgSO_4$, filtered and concentrated. The crude product was purified by chromatography (10% ethyl acetate/hexanes) on silica gel to obtain the title compound (43.6 mg, 0.090 mmol, 27%). $^1$H NMR (CDCl$_3$): δ 8.66 (d, J=2.4, 1H), 7.87 (dd, J=9.3, 2.4, 1H), 7.32 (s, 2H), 7.27 (d, J=9.0, 1H), 3.97 (s, 3H), 3.61 (s, 3H), 2.77 (s, 3H).

Example 3

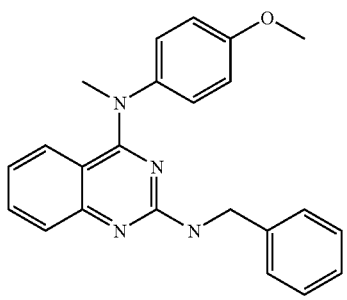

(2-Benzylamino-quinazolin-4-yl)-(4-methoxyphenyl)-methylamine

A solution of (2-chloro-quinazolin-4-yl)-(4-methoxyphenyl)-methylamine (150 mg, 0.5 mmol), benzyl amine (110 uL, 1.0 mmol) and triethyl amine (100 uL) in 5 mL of THF in a seal tube was heated overnight at 80° C. After cooling to room temperature the reaction mixture was diluted with 25 mL of ethyl acetate, washed with saturated NaHCO$_3$, dried over anhydrous Na$_2$SO$_4$, filtered and concentrated. The crude was purified by column chromatography (35% ethyl acetate/hexane) to give the title compound (25 mg, 0.067 mmol, 13%). $^1$H NMR (CDCl$_3$): 7.24-7.46 (m, 7H), 7.10 (m, 2H), 6.84-6.92 (m, 3H), 6.68 (ddd, J=8.1, 6.9, 1.5, 1H), 4.78 (d, J=6.5, 2H), 3.83 (s, 3H), 3.46 (s, 3H).

Example 4

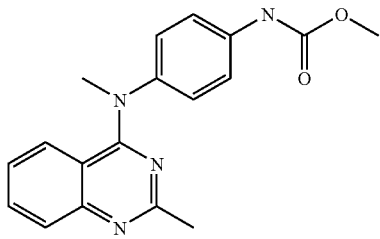

(2-Methyl-quinazolin-4-yl)-(4-methoxycarbonylamino-phenyl)-methylamine

To a mixture of (4-amino-phenyl)-(2-methyl-quinazolin-4-yl)-methylamine (75 mg, 0.28 mmol) in 5 mL of THF with K$_2$CO$_3$ (80 mg, 0.58 mmol) and Na$_2$SO$_4$ (80 mg, 0.56 mmol) cooled at 0° C. was added methyl chloroformate (200 uL, 2.6 mmol), followed by 500 uL of water dropwise while stirring vigorously. The mixture was stirred for 5 min at 0° C., and diluted with 25 mL of ethyl acetate. The mixture was washed with saturated NaHCO$_3$, the organic layer was dried over anhydrous Na$_2$SO$_4$, filtered and concentrated. The crude was purified by column chromatography (45% ethyl acetate/hexane) to give the title compound (65 mg, 0.20 mmol, 71%). $^1$H NMR (CDCl$_3$): 7.74 (m, 1H), 7.53 (ddd, J=8.4, 6.6, 1.8, 1H), 7.40 (m, 2H), 7.04-7.12 (m, 3H), 6.97 (m, 1H), 6.73 (s, broad, 1H), 3.80 (s, 3H), 3.60 (s, 3H), 2.73 (s, 3H).

Example 5

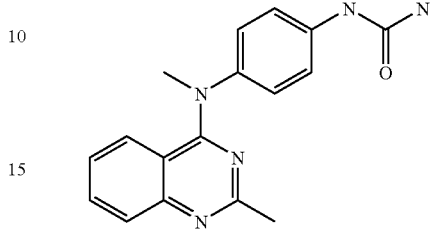

(2-Methyl-quinazolin-4-yl)-(4-ureido-phenyl)-methylamine

To a solution of (4-amino-phenyl)-(2-methyl-quinazolin-4-yl)-methylamine (48 mg, 0.18 mmol) in 250 uL of methanol and 750 uL of 1N HCl was added potassium cyanate (50 mg, 0.62 mmol) in 500 uL of water, and the mixture was stirred overnight at room temperature. The precipitated product was collected by filtration under vacuum, washed with 1 mL of cold water and dried to give the title compound (12.3 mg, 0.04 mmol, 22%). $^1$H NMR (DMSO): 8.75 (s, 1H), 7.60 (m, 2H), 7.45 (m, 2H), 6.99-7.13 (m, 4H), 5.92 (s, 2H), 3.45 (s, 3H), 2.59 (s, 3H).

Example 6

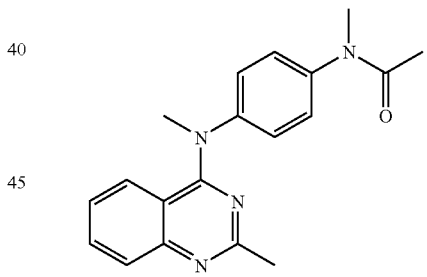

(2-Methyl-quinazolin-4-yl)-(N-methyl-4-acetamidophenyl)-methylamine

To a solution of (4-acetamido-phenyl)-(2-methyl-quinazolin-4-yl)-methylamine (231 mg, 0.075 mmol) in 5 mL of DMF was added methyl iodide (0.9 g, 6.3 mmol) and the mixture was cooled to 0° C. Sodium hydride (60% oil suspension, 75 mg, 1.9 mmol) was added, and the mixture was stirred at 0° C. for 1 h, then allowed to warm to room temperature and stirred for 1 h. The reaction mixture was quenched by adding 50 uL of water, diluted with 25 mL of ethyl acetate, washed with water (25 mL×3) and saturated NaCl. The organic layer was dried over anhydrous MgSO$_4$, filtered and concentrated. The residue was purified by chromatography (90% ethyl acetate/hexanes) to give the title compound (143 mg, 0.45 mmol, 59%). $^1$H NMR (CDCl$_3$):

7.19 (d, J=8.1, 1H), 7.54 (ddd, J=8.4, 6.6, 1.8, 1H), 7.16 (s, broad, 4H), 6.97-7.09 (m, 2H), 3.66 (s, 3H), 3.28 (s, 3H), 2.76 (s, 3H), 1.92 (s, 3H).

Example 7

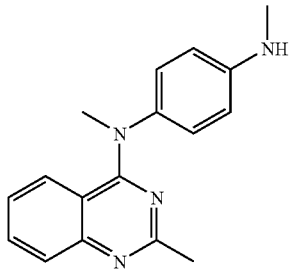

(2-Methyl-quinazolin-4-yl)-(4-methylamino-phenyl)-methylamine

A mixture of (2-methyl-quinazolin-4-yl)-(N-methyl-4-acetamido-phenyl)-methylamine (103 mg, 0.321 mmol) in 3 mL of methanol and 3 mL of 2N NaOH was heated at 90° C. for 4 h. The reaction mixture was cooled to room temperature and diluted 25 mL of ethyl acetate. It was washed with saturated $NaHCO_3$, and the organic layer was dried over anhydrous $Na_2SO_4$, filtered and concentrated. The crude was purified by column chromatography (40% ethyl acetate/hexane) to give the title compound (28 mg, 0.10 mmol, 31%). $^1$H NMR ($CDCl_3$): 7.71 (m, 1H), 7.50 (ddd, J=8.4, 6.9, 1.5, 1H), 6.93-7.11 (m, 4H), 6.60 (m, 2H), 3.84 (s, broad, 1H), 3.57 (s, 3H), 2.87 (s, 3H), 2.70 (s, 3H).

Example 8

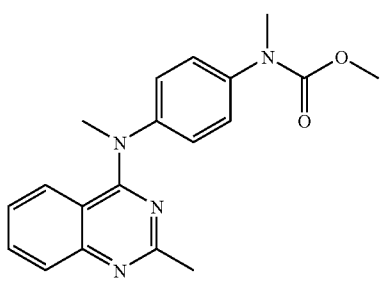

(2-Methyl-quinazolin-4-yl)-[4-(N-methyl-methoxycarbonylamino)-phenyl]-methylamine The title compound was prepared from (2-methyl-quinazolin-4-yl)-(4-methylamino-phenyl)-methylamine by a procedure similar to example 4. $^1$H NMR ($CDCl_3$): 7.76 (m, 1H), 7.55 (m, 1H), 7.24 (m, 2H), 6.98-7.13 (m, 4H), 3.75 (s, 3H), 3.63 (s, 3H), 3.32 (s, 3H), 2.74 (s, 3H).

Example 9

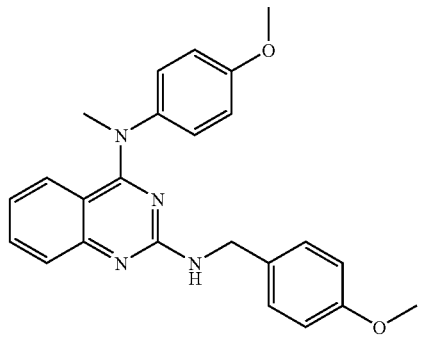

[2-(4-Methoxy-benzylamino)-quinazolin-4-yl)]-(4-methoxyphenyl)-methylamine

The title compound was prepared from (2-chloro-quinazolin-4-yl)-(4-methoxyphenyl)-methylamine and 4-methoxybenzyl amine by a procedure similar to example 3. $^1$H NMR ($CDCl_3$): 7.35-7.45 (m, 4H), 7.10 (m, 2H), 6.88 (m, 5H), 6.67 (ddd, J=8.4, 6.9, 1.5, 1H), 5.25 (s, broad, 1H), 4.70 (d, J=6.0, 2H), 3.83 (s, 3H), 3.81 (s, 3H), 3.47 (s, 3H).

Example 10

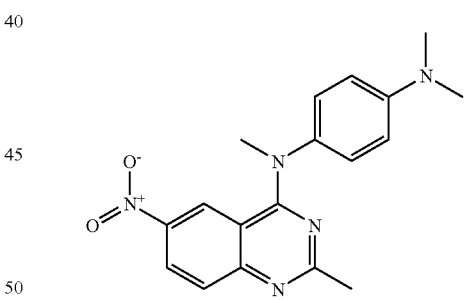

(2-Methyl-6-nitroquinazolin-4-yl)-(4-dimethylaminophenyl)-methylamine

A mixture of 4-chloro-2-methyl-6-nitro-quinazolinone (160 mg, 0.72 mmol), $N^1,N^1,N^4$-trimethylbenzene-1,4-diamine (0.84 mmol) and sodium acetate (70 mg, 0.90 mmol) in 5 mL of solvent (THF:water/1:1) was stirred at room temperature for 45 min. The reaction mixture was diluted with 50 mL of ethyl acetate and washed with saturated $NaHCO_3$. The organic layer was dried over anhydrous $MgSO_4$, filtered and concentrated. The crude product was purified by chromatography (40% ethyl acetate/hexanes) on silica gel to give the title compound (231 mg, 0.68 mmol, 96%). $^1$H NMR (CDCl₃): 8.24 (dd, J=9.6, 3.0, 1H), 7.82 (d, J=2.4, 1H), 7.72 (d, J=9.0, 1H), 7.08 (m, 2H), 6.78 (m, 2H), 3.64 (s, 3H), 3.01 (s, 6H), 2.71 (s, 3H).

Example 11

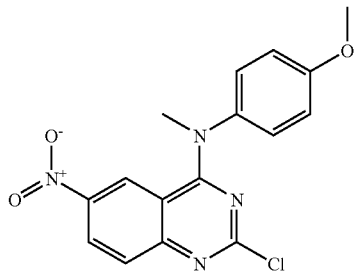

(2-Chloro-6-nitroquinazolin-4-yl)-(4-methoxyphenyl)-methylamine

The title compound was prepared from 2,4-dichloro-6-nitro-quinazoline and 4-methoxy-N-methylaniline by a procedure similar to example 10. ¹H NMR (CDCl₃): 8.31 (dd, J=9.6, 3.6, 1H), 7.78 (d, J=9.3, 1H), 7.73 (d, J=2.4, 1H), 7.21 (m, 2H), 7.06 (m, 2H), 3.90 (s, 3H), 3.69 (s, 3H).

Example 12

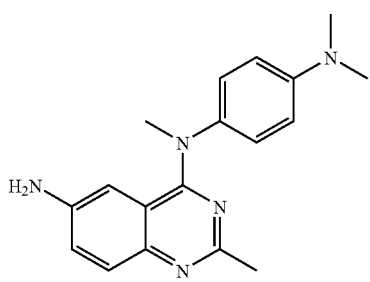

(6-Amino-2-methyl-quinazolin-4-yl)-(4-dimethylaminophenyl)-methylamine

A mixture of (2-methyl-6-nitroquinazolin-4-yl)-(4-dimethylaminophenyl)-methylamine (214 mg, 0.634 mmol) in 20 mL of ethyl acetate and methanol (1:1) with 5% Palladium on carbon was hydrogenated at 70 psi for 5 h. The reaction mixture was filtered and concentrated. The crude product was purified by chromatography (5% methanol/methylene chloride) to give the title compound (195 mg, 0.634 mmol, 100%). ¹H NMR (CDCl₃): 7.58 (d, J=8.7, 1H), 7.02 (m, 2H), 6.97 (dd, J=9.0, 2.7, 1H), 6.69 (m, 2H), 6.21 (d, J=2.4, 1H), 3.54 (s, 3H), 3.45 (s, broad, 2H), 2.97 (s, 6H), 2.67 (s, 3H).

Example 13

(2-Chloro-quinazolin-4-yl)-(4-dimethylaminophenyl)-methylamine

The title compound was prepared from 2,4-dichloro-6-nitro-quinazoline and N¹,N¹,N⁴-trimethylbenzene-1,4-diamine by a procedure similar to example 10. ¹H NMR (CDCl₃): 7.71 (m, 1H), 7.51-7.56 (m, 1H), 7.07 (m, 2H), 6.99 (m, 2H), 6.71 (m, 2H), 3.59 (s, 3H), 3.01 (s, 6H).

Example 14

(2-Dimethylamino-6-nitroquinazolin-4-yl)-(4-methoxyphenyl)-methylamine

A solution of (2-chloro-6-nitroquinazolin-4-yl)-(4-methoxyphenyl)-methylamine (48 mg, 0.14 mmol) in 2 mL of dimethylamine in methanol (2M, 25 mmol) was heated overnight in a seal tube at 70° C. for 48 h. The reaction mixture was cooled to room temperature and concentrated under vacuum. The residue was purified by chromatography (15% ethyl acetate/hexane) to give the title compound (39 mg, 79%). ¹H NMR (CDCl₃): 8.08 (dd, J=9.3, 2.4, 1H), 7.71 (d, J=2.4, 1H), 7.35 (d, J=9.3, 1H), 7.14 (m, 2H), 6.97 (2H), 3.85 (s, 3H), 3.55 (s, 3H), 3.33 (s, 6H).

Example 15

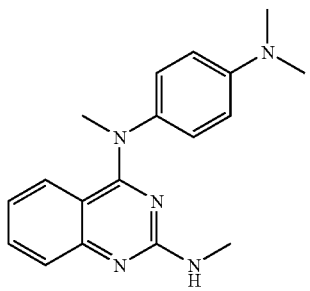

(2-Methylamino-quinazolin-4-yl)-(4-dimethylaminophenyl)-methylamine

The title compound was prepared from (2-chloro-quinazolin-4-yl)-(4-dimethylaminophenyl)-methylamine and methyl amine by a procedure similar to example 14. $^1$H NMR (CDCl$_3$): 7.42-7.42 (m, 1H), 7.34 (ddd, J=8.1, 6.9, 4.0, 1H), 7.04 (m, 2H), 6.94 (m, 1H), 6.63-6.71 (m, 3H), 5.13 (s, broad, 1H), 3.49 (s, 3H), 3.10 (d, J=4.8, 3H), 2.97 (s, 6H).

Example 16

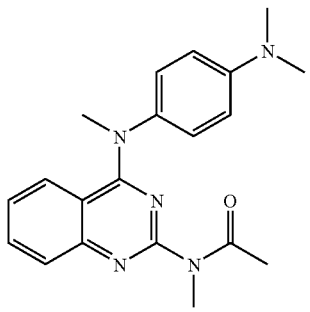

[2-(N-Methyl-acetamido)-quinazolin-4-yl]-(4-dimethylaminophenyl)-methylamine

To a solution of (2-methylamino-quinazolin-4-yl)-(4-dimethylaminophenyl)-methylamine (40 mg, 0.13 mmol) in 4 mL of methylenechloride cooled at 0° C. was added triethylamine (50 uL, 0.36 mmol), few crystals of dimethylaminopyridine and acetic anhydride (50 uL, 0.53 mmol). The reaction mixture was stirred for 1 h at 0° C., warmed to room temperature, and stirred overnight. The reaction mixture was diluted with 25 mL of ethyl acetate and washed with 25 mL of saturated sodium bicarbonate. The organic layer was dried over anhydrous NaSO$_4$, filtered and concentrated. The residue was purified by chromatography (40% ethyl acetate/hexane) to give the title compound (39 mg, 0.11 mmol, 85%). $^1$H NMR (CDCl$_3$): 7.65-7.69 (m, 1H), 7.52 (ddd, J=8.4, 6.6, 1.8, 1H), 6.93-7.12 (m, 4H), 6.72 (m, 2H), 3.56 (s, 3H), 3.01 (s, 6H), 2.52 (s, 3H).

Example 17

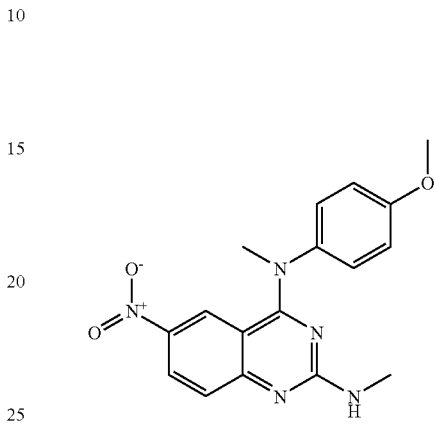

(2-Methylamino-6-nitroquinazolin-4-yl)-(4-methoxyphenyl)-methylamine

The title compound was prepared from (2-chloro-6-nitroquinazolin-4-yl)-(4-methoxyphenyl)-methylamine and methyl amine by a procedure similar to example 14. $^1$H NMR (CDCl$_3$): 8.11 (dd, J=9.3, 8.0, 1H), 7.73 (d, J=2.4, 1H), 7.33 (m, 1H), 7.15 (m, 2H), 6.98 (m, 2H), 5.29 (s, broad, 1H), 3.86 (s, 3H), 3.55 (s, broad, 3H), 3.14 (d, J=4.8, 3H).

Example 18

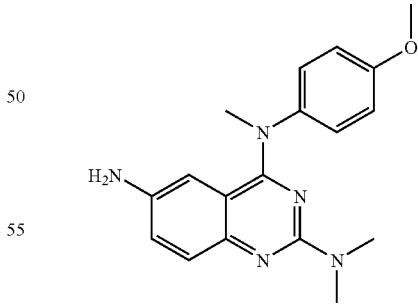

(6-Amino-2-dimethylamino-quinazolin-4-yl)-(4-methoxyphenyl)-methylamine

The title compound was prepared from (2-dimethylamino-6-nitroquinazolin-4-yl)-(4-methoxyphenyl)-methylamine by a procedure similar to example 12. $^1$H NMR (CDCl$_3$): 7.74

(m, 1H), 7.11 (m, 2H), 6.89 (m, 3H), 6.00 (m, 1H), 3.83 (s, 3H), 3.52 (s, 3H), 3.33 (s, 6H).

Example 19

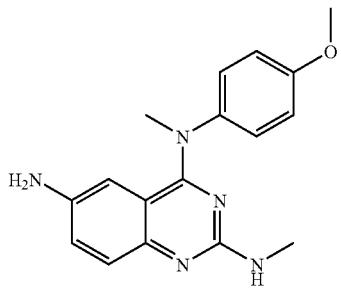

(6-Amino-2-methylamino-quinazolin-4-yl)-(4-methoxyphenyl)-methylamine

The title compound was prepared from (2-methylamino-6-nitroquinazolin-4-yl)-(4-methoxyphenyl)-methylamine by a procedure similar to example 12. $^1$H NMR (CDCl$_3$): 7.34 (m, 1H), 7.06-7.13 (m, 3H), 6.90 (m, 3H), 6.04 (m, 1H), 5.67 (s, broad, 1H), 3.82 (s, 3H), 3.50 (s, 3H), 3.08 (d, J=5.1, 3H).

Example 20

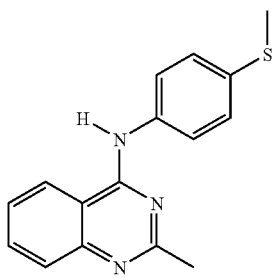

(4-Methylthio-phenyl)-(2-methyl-quinazolin-4-yl)-amine

A mixture of 4-chloro-2-methyl-quinazoline (178.6 mg, 1.0 mmol), 4-methylthio-aniline (139.2 mg, 1.0 mmol) and sodium acetate (98.4 mg, 1.20 mmol) in 4 mL of solvent (THF:water=1:1) was stirred at 60-70° C. for 3 h. The reaction mixture was diluted with 30 mL of ethyl acetate. It was washed with brine, dried over anhydrous Na$_2$SO$_4$, filtered and concentrated. The crude product was rinsed with ethyl acetate and dried, yielding 273 mg of title compound (97.2%). $^1$H NMR (CDCl$_3$): 7.86-7.82 (m, 2H), 7.79-7.73 (m, 3H)), 7.50-7.45 (m, 2H), 7.34-7.26 (m, 2H), 2.7 (s, 3H), 2.51 (s, 3H),

Example 21

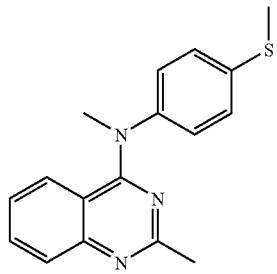

(4-Methylthio-phenyl)-(2-methyl-quinazolin-4-yl)-methylamine

To a solution of (4-methylthio-phenyl)-(2-methyl-quinazolin-4-yl)-amine (263 mg, 0.94 mmol) in DMF (4 ml) at 0° C. was added sodium hydride (56.4 mg, 1.40 mmol, 60% oil dispersion) and followed by methyl iodide (0.09 ml, 1.40 mmol). The mixture was stirred at 0° C. for 1 h, then allowed to warm to room temperature and stirred for another 2 h. The reaction mixture was diluted with EtOAc (15 ml), washed with saturated NaHCO$_3$ aq., brine, dried over Na$_2$SO$_4$, filtered and concentrated by vacuum. The residue was purified by chromatography on silica gel with acetate and hexane (1:2 to 1:1) as eluent, yielding 120 mg of title compound (40.7%). $^1$H NMR (CDCl$_3$): 7.76 (d, J=9.0 Hz, 1H), 7.54 (t, J=7.5 Hz, 1H), 7.24-7.19 (m, 2H), 7.10-6.97 (m, 4H), 3.59 (s, 3H), 2.74 (s, 3H), 2.48 (s, 3H)

Example 22

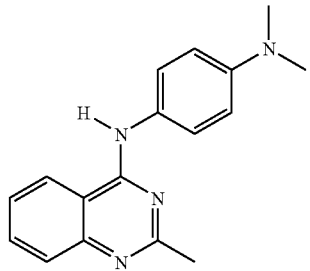

(4-Dimethylamino-phenyl)-(2-methyl-quinazolin-4-yl)-amine

The title compound was prepared from 4-chloro-2-methyl-quinazoline (178.6 mg, 1.0 mmol), 4-dimethylamino-aniline (136.2 mg, 1.0 mmol) and sodium acetate (98.4 mg, 1.2 mmol) similar to example 20 to give 222 mg (79.9%) of gray solids. $^1$H NMR (CDCl$_3$): 7.82-7.70 (m, 3H), 7.62 (d, J=9.0 Hz, 2H), 7.45 (t, J=7.5 Hz, 1H), 6.80 (d, J=9.0 Hz, 2H), 2.97 (s, 6H), 2.66 (s, 3H).

Example 23

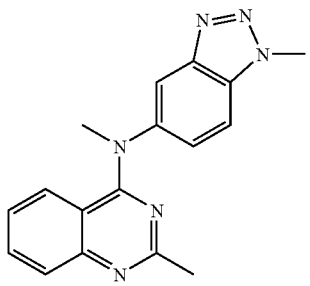

(1-Methyl-1H-benzotriazol-5-yl)-(2-methyl-quinazolin-4-yl)-methylamine

The title compound was prepared from 4-chloro-2-methyl-quinazoline (178.6 mg, 1.0 mmol), (1-methyl-1H-1,2,3-benzotriazol-5-yl)methylamine (162.2 mg, 1.0 mmol) and sodium acetate (98.4 mg, 1.2 mmol) similar to example 20 to give 85 mg (28%) of yellow solids. $^1$H NMR (CDCl$_3$): 8.07 (s, 1H), 7.80 (d, J=7.8 Hz, 1H), 7.74-7.67 (m, 2H), 7.61 (d, J=8.4 Hz, 1H), 7.51 (d, J=8.4 Hz, 1H), 7.40 (t, J=8.1 Hz, 1H), 6.04 (brs, 1H)), 5.06 (d, J=5.4 Hz, 2H), 4.31 (s, 3H), 2.68 (s, 3H).

Example 24

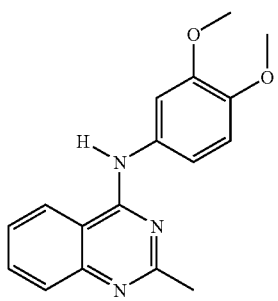

(3,4-Dimethoxy-phenyl)-(2-methyl-quinazolin-4-yl)-amine

The title compound was prepared from 4-chloro-2-methyl-quinazoline (178.6 mg, 1.0 mmol), 3,4-dimethoxy-aniline (153 mg, 1.0 mmol) and sodium acetate (98.4 mg, 1.2 mmol) similar to example 20 to give 295 mg (100%) of off white solids. $^1$H NMR (CDCl$_3$): 7.85-7.70 (m, 4H), 7.51-7.46 (m, 1H), 7.38 (brs, 1H), 7.16 (dd, J=2.1 Hz, J=8.7 Hz, 1H), 6.90 (d, J=8.7 Hz, 1H), 3.95 (s, 3H)), 3.91 (s, 3H), 2.69 (s, 3H).

Example 25

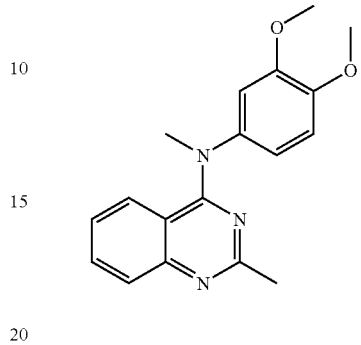

(3,4-Dimethoxy-phenyl)-(2-methyl-quinazolin-4-yl)-methylamine

The title compound was prepared from (3,4-dimethoxy-phenyl)-(2-methyl-quinazolin-4-yl)-amine (288 mg, 0.98 mmol), methyl iodide (0.094 ml, 1.47 mmol), sodium hydride (60 mg, 1.5 mmol) in DMF similar to example 21 to give 70 mg (23%) of off white solids. $^1$H NMR (CDCl$_3$): 7.75-7.72 (m, 1H), 7.56-7.50 (m, 1H), 7.05-6.94 (m, 2H), 6.85 (d, J=7.5 Hz, 1H), 6.76-6.71 (m, 2H), 3.92 (s, 3H)), 3.78 (s, 3H), 3.61 (s, 3H), 2.73 (s, 3H).

Example 26

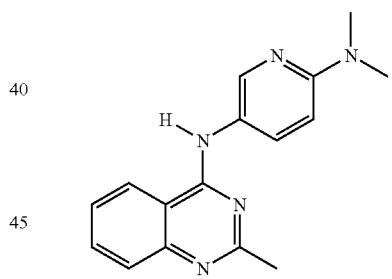

(2-Dimethylamino-pyridine-5-yl)-(2-methyl-quinazolin-4-yl)-amine

2-Dimethylamino-5-nitropyridine: To a solution of 2-chloro-5-nitropyridine (317.08 mg, 2 mmol) in 1 ml of methanol was added of 2 M dimethylamine/MeOH (5 ml, 10 mmol) in a sealed tube at 0° C. The reaction mixture was warmed up to room temperature and stirred over night. After evaporating the solvent, the residue was diluted with EtOAc (20 ml), washed with saturated NaHCO$_3$ aq., brine, dried over Na$_2$SO$_4$, filtered and concentrated by vacuum, yielding 334 mg (100%) of yellow solids. $^1$H NMR (CDCl$_3$): 9.06 (d, J=2.7 Hz, 1H), 8.22-8.18 (m, 1H), 6.46 (d, J=9.3 Hz, 1H), 3.23 (s, 6H).

(2-Dimethylamino-pyridine-5-yl)-(2-methyl-quinazolin-4-yl)-amine: To a solution of 2-dimethylamino-5-nitropyridine (334 mg, 2 mmol) in 100 ml of methanol was added 5% Pd/C (100 mg, 0.94 mmol). The reaction mixture was hydrogenated under 45 psi at room temperature for 2 h, then it was filtered through a layer of celite (2.5 in d×2 in h) and washed with additional methanol (25 ml). The organic filtrate was concentrated to yield 200 mg (73%) of 2-dimethylamino-5-amino-pyridine as dark brown sticky solids. The title compound was prepared from 4-chloro-2-methyl-quinazoline (182.2 mg, 1.02 mmol), 2-dimethylamino-5-amino-pyridine (140 mg, 1.02 mmol) and sodium acetate (98.4 mg, 1.2 mmol) similar to example 20 to give 60 mg (21%) of paint yellow solids. $^1$H NMR (CDCl$_3$): 8.43 (d, J=2.4 Hz, 1H), 7.95 (dd, J=2.7 Hz, J=9.3 Hz, 1H), 7.84-7.72 (m, 3H), 7.47 (t, J=8.1 Hz, 1H), 7.16 (brs, 1H), 6.61 (d, J=9.0 Hz, 1H), 3.12 (s, 6H), 2.65 (s, 3H).

Example 27

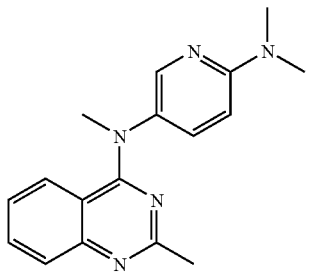

(2-Dimethylamino-pyridine-5-yl)-(2-methyl-quinazolin-4-yl)-methylamine

The title compound was prepared from (2-dimethylamino-pyridine-5-yl)-(2-methyl-quinazolin-4-yl)-amine (45 mg, 0.16 mmol), methyl iodide (0.016 ml, 0.24 mmol), sodium hydride (9.6 mg, 0.24 mmol, 60% oil dispersion) in DMF similar to example 21 to give 22 mg (47%) of paint yellow solids. $^1$H NMR (CDCl$_3$): 8.07 (d, J=2.4 Hz, 1H), 7.63 (dd, J=0.9 Hz, J=8.4 Hz, 1H), 7.56-7.51 (m, 1H), 7.27-7.18 (m, 2H), 7.05-7.00 (m, 1H), 6.50 (d, J=9.3 Hz, 1H), 3.55 (s, 3H), 3.12 (s, 6H), 2.72 (s, 3H).

Example 28

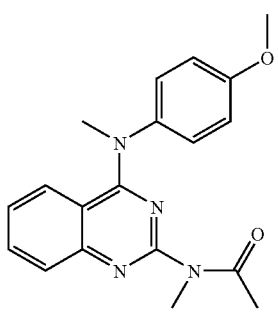

(4-Methoxy-phenyl)-(2-N-methylacetamido-quinazolin-4-yl)-methylamine

To a solution of (4-methoxy-phenyl)-(2-methylamine-quinazolin-4-yl)-methylamine (100 mg, 0.34 mmol) in 5 ml of dichloromethane was added triethylamine (0.071 ml, 0.51 mmol), acetyl chloride (0.036 ml, 0.51 mmol) followed by 2 mg of DMAP at 0° C. The reaction mixture was allowed to warm to room temperature and stirred for 2 h. The solvent was removed by vacuum. The residue was dissolved in EtOAc (20 ml), washed with water, brine, dried over Na$_2$SO$_4$, filtered and concentrated by vacuum. The crude product was purified by chromatography on silica gel with acetate, hexane and methanol (1:3 to 1:1:0.05) as eluent, yielding 36 mg of title compound (31.5%) as white solids. $^1$H NMR (CDCl$_3$): 7.70-7.67 (m, 1H), 7.56-7.52 (m, 1H), 7.17-7.14 (m, 2H), 6.97-6.93 (m, 4H), 3.86 (s, 3H), 3.57 (s, 6H), 2.52 (s, 3H).

Example 29

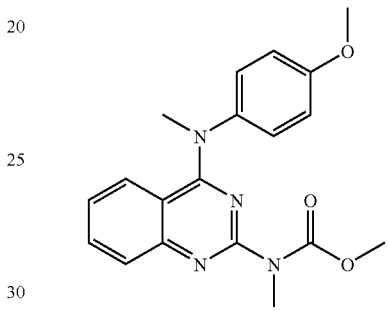

(4-Methoxy-phenyl)-(2-N-methyl-methoxycarbony-lamino-quinazolin-4-yl)-methylamine The title compound was prepared from (4-methoxy-phenyl)-(2-methylamine-quinazolin-4-yl)-methylamine (100 mg, 0.34 mmol), triethylamine (0.071 ml, 0.51 mmol), methyl chloroformate (0.039 ml, 0.51 mmol), and DMAP (2 mg) in 5 ml of THF similar to example 28 to give 26 mg (21.7%) of off white liquid. $^1$H NMR (CDCl$_3$): 7.73 (d, J=7.8 Hz, 1H), 7.54-7.48 (m, 1H), 7.16-7.12 (m, 2H), 6.95-6.90 (m, 4H), 3.85-3.84 (m, 6H), 3.58 (s, 3H), 3.55 (s, 3H).

Example 30

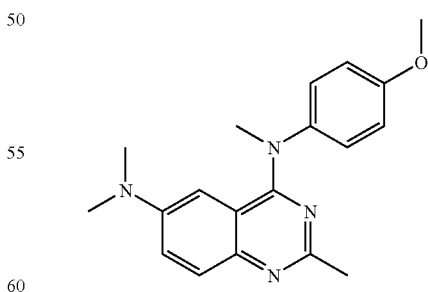

(6-Dimethylamino-2-methyl-quinazolin-4-yl)-(4-methoxy-phenyl)-methylamine

To a mixture of (6-amino-2-methyl-quinazolin-4-yl)-(4-methoxy-phenyl)-methylamine (16 mg, 0.05 mmol), 2 ml of 37% formaldehyde water solution and sodium cyanoborohydride (6.3 mg, 0.1 mmol) was added 2 N HCl (0.05 ml) at 0° C. The reaction mixture was stirred for 1 h at 0° C., then diluted by EtOAc (10 ml), washed with saturated NaHCO$_3$ aq., brine, dried over Na$_2$SO$_4$, filtered and concentrated by vacuum. The crude product was purified by chromatography on silica gel with acetate, hexane (1:3 to 1:1) as eluent, yielding 11 mg of title compound (68.8%) as yellow solids. $^1$H NMR (CDCl$_3$): 7.63 (d, J=9.0 Hz, 1H), 7.20-7.12 (m, 3H), 6.91-6.88 (m, 2H), 6.23 (d, J=2.7 Hz, 1H), 3.80 (s, 3H), 3.57 (s, 3H), 2.69 (s, 3H), 2.62 (s, 6H).

Example 31

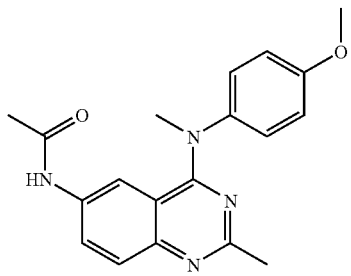

(6-Acetamido-2-methyl-quinazolin-4-yl)-(4-methoxy-phenyl)-methylamine

The title compound was prepared from (6-amino-2-methyl-quinazolin-4-yl)-(4-methoxy-phenyl)-methylamine (30 mg, 0.102 mmol), triethylamine (0.021 ml, 0.153 mmol), acetyl chloride (0.011 ml, 0.153 mmol) and DMAP (1 mg) in 5 ml of dichloromethane similar to example 28 to give 3 mg (9%) of paint brown solids. $^1$H NMR (CDCl$_3$): 7.71 (s, 2H), 7.19 (s, 1H), 7.12-7.09 (m, 2H), 6.93-6.91 (m, 3H), 3.84 (s, 3H), 3.56 (s, 3H), 2.71 (s, 3H), 2.07 (s, 3H).

Example 32

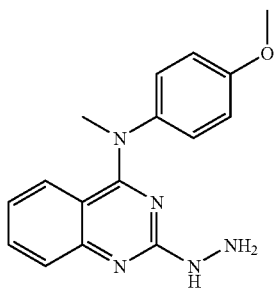

(2-Hydrazinyl-quinazolin-4-yl)-(4-methoxy-phenyl)-methylamine

To a solution of (2-chloro-quinazolin-4-yl)-(4-methoxy-phenyl)-methylamine (100 mg, 0.33 mmol) in 2 ml of 1,4-dioxane was added 0.4 ml of hydrazine. The reaction mixture was stirred at room temperature overnight. After evaporating the solvent, the residue was diluted with EtOAc (20 ml), washed with saturated NaHCO$_3$ aq., brine, dried over Na$_2$SO$_4$, filtered and concentrated by vacuum, yielding 20 mg (21%) of yellow solids. $^1$H NMR (CDCl$_3$): 7.52-7.49 (m, 1H), 7.44-7.39 (m, 1H), 7.12-7.08 (m, 2H), 6.93-6.88 (m, 3H), 6.77-6.71 (m, 1H), 6.01 (brs, 1H), 4.11 (brs, 2H), 3.83 (s, 3H), 3.50 (s, 3H).

Example 33

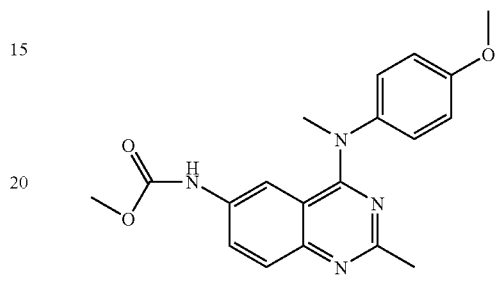

(6-methoxycarbonylamino-2-methyl-quinazolin-4-yl)-(4-methoxy-phenyl)-methylamine To a solution of (6-amino-2-methyl-quinazolin-4-yl)-(4-methoxy-phenyl)-methylamine (150 mg, 0.51 mmol) in 5 ml of THF was added potassium carbonate (160 mg, 1.16 mmol), 2 mg of sodium sulfate. The reaction mixture was cooled to 0° C., and methyl chloroformate (0.4 ml, 5 mmol) was added. The reaction mixture was stirred at 0° C. for 10-15 min, then diluted with EtOAc (20 ml), washed with water, brine, dried over Na$_2$SO$_4$, filtered and concentrated by vacuum. The crude product was purified by chromatography on silica gel with acetate, hexane (1:3 to 1:1) as eluent, yielding 129 mg of title compound (72%) as yellow solids. $^1$H NMR (CDCl$_3$): 7.70 (s, 2H), 7.12-7.07 (m, 2H), 6.94-6.89 (m, 3H), 6.32 (brs, 1H), 3.84 (s, 3H), 3.70 (s, 3H), 3.57 (s, 3H), 2.70 (s, 3H).

Example 34

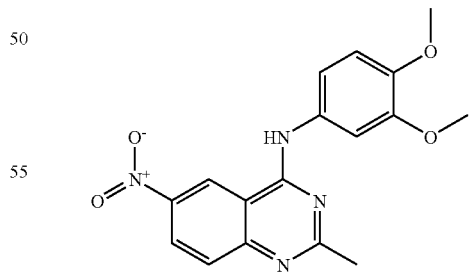

(3,4-Dimethoxy-phenyl)-(2-methyl-6-nitro-quinazolin-4-yl)-amine

The title compound was prepared from 4-chloro-2-methyl-6-nitro-quinazoline (80 mg, 0.36 mmol), 3,4-dimethoxy-aniline (54.8 mg, 0.36 mmol) and sodium acetate (35.2 mg, 0.43 mmol) similar to example 20 to give 109 mg (89.5%) of yellow solids. ¹H NMR (CDCl₃): 8.87 (d, J=2.7 Hz, 1H), 8.56 (dd, J=2.4 Hz, J=9.0 Hz, 1H), 7.91 (d, J=9.0 Hz, 1H), 7.63-7.61 (m, 2H), 7.28-7.24 (m, 1H), 6.94 (d, J=8.7 Hz, 1H), 3.96 (s, 3H)), 3.93 (s, 3H), 2.71 (s, 3H).

Example 35

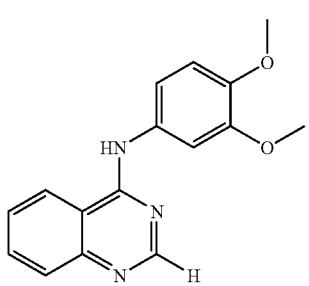

(3,4-Dimethoxy-phenyl)-(quinazolin-4-yl)-amine

The title compound was prepared from 4-chloro-quinazoline (82.3 mg, 0.5 mmol), 3,4-dimethoxy-aniline (76.6 mg, 0.5 mmol) and sodium acetate (49.2 mg, 0.6 mmol) similar to example 20 to give 138 mg (92.5%) of off white solids. ¹H NMR (CDCl₃): 8.74 (s, 1H), 7.91 (t, J=8.7 Hz, 2H), 7.57 (t, J=8.1 Hz, 1H), 7.57 (t, J=8.1 Hz, 1H), 7.45 (s, 1H), 7.38 (d, J=2.4 Hz, 1H), 7.16-7.13 (m, 1H), 6.92 (d, J=8.4 Hz, 1H), 3.93-3.91 (m, 6H).

Example 36

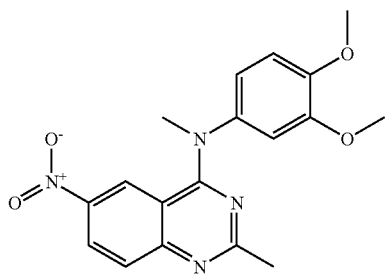

(3,4-Dimethoxy-phenyl)-(2-methyl-6-nitro-quinazolin-4-yl)-methylamine

The title compound was prepared from (3,4-dimethoxy-phenyl)-(2-methyl-6-nitro-quinazolin-4-yl)-amine (105 mg, 0.31 mmol), methyl iodide (0.029 ml, 0.46 mmol), sodium hydride (19 mg, 0.46 mmol, 60% oil dispersion) in DMF similar to example 21 to give 10.1 mg (9.2%) of yellow solids. ¹H NMR (CDCl₃): 8.30-8.62 (m, 1H), 7.91 (d, J=2.4 Hz, 1H), 7.76 (d, J=9.3 Hz, 1H), 6.97 (d, J=8.4 Hz, 1H), 6.86-6.82 (m, 1H), 6.74 (d, J=2.7 Hz, 1H), 3.95 (s, 3H)), 3.81 (s, 3H), 3.66 (s, 3H), 2.73 (s, 3H).

Example 37

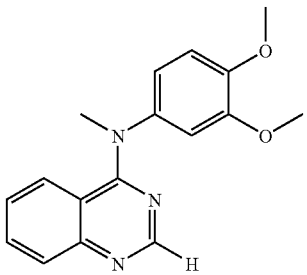

(3,4-Dimethoxy-phenyl)-(quinazolin-4-yl)-methylamine

The title compound was prepared from (3,4-dimethoxy-phenyl)-quinazolin-4-yl-amine (130 mg, 0.46 mmol), methyl iodide (0.043 ml, 0.7 mmol), sodium hydride (28 mg, 0.7 mmol, 60% oil dispersion) in DMF similar to example 21 to give 2.0 mg (2%) of white solids. ¹H NMR (CDCl₃): 7.88 (s, 1H), 7.55-7.45 (m, 2H), 7.31 (d, J=7.2 Hz, 1H), 6.97 (t, J=7.2 Hz, 1H), 6.86 (d, J=8.4 Hz, 1H), 6.45 (d, J=2.1 Hz, 1H), 6.37 (d, J=2.4 Hz, J=8.1 Hz, 1H), 3.91 (s, 3H), 3.82 (s, 3H), 3.53 (s, 3H).

Example 38

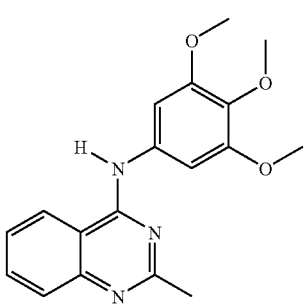

(2-Methyl-quinazolin-4-yl)-(3,4,5-trimethoxy-phenyl)-amine

The title compound was prepared from 4-chloro-2-methyl-quinazoline (179 mg, 1.0 mmol), 3,4,5-trimethoxy-aniline (183 mg, 1.0 mmol) and sodium acetate (98.4 mg, 1.2 mmol) similar to example 20 to give 239 mg (73.5%) of white solids.

¹H NMR (CDCl₃): 7.88 (t, J=7.2 Hz, 2H), 7.77 (t, J=7.2 Hz, 1H), 7.51 (t, J=8.1 Hz, 2H), 7.22 (s, 2H), 3.92-3.87 (m, 9H), 2.72 (s, 3H).

Example 39

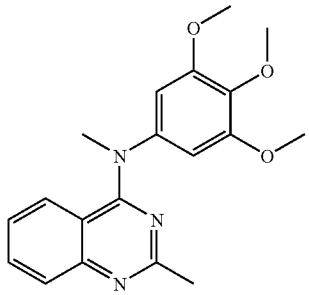

(3,4,5-trimethoxy-phenyl)-(2-methyl-quinazolin-4-yl)-methylamine

The title compound was prepared from (3,4,5-trimethoxy-phenyl)-(2-methyl-quinazolin-4-yl)-amine (232 mg, 0.71 mmol), methyl iodide (0.07 ml, 1.08 mmol), sodium hydride (43 mg, 1.08 mmol, 60% oil dispersion) in DMF similar to example 21 to give 65 mg (27%) of white solids. ¹H NMR (CDCl₃): 7.75 (d, J=8.4 Hz, 1H), 7.58-7.53 (m, 1H), 7.11-7.00 (m, 2H), 6.39 (s, 2H), 3.88 (s, 3H), 3.73 (s, 6H), 3.62 (s, 3H), 2.74 (s, 3H).

Example 40

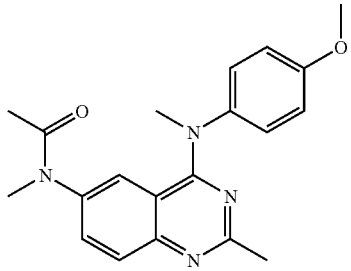

(6-N-methyl-acetamido-2-methyl-quinazolin-4-yl)-(4-methoxy-phenyl)-methylamine

The title compound was prepared from (6-acetamido-2-methyl-quinazolin-4-yl)-(4-methoxy-phenyl)-methylamine (240 mg, 0.71 mmol), methyl iodide (0.08 ml, 1.34 mmol), sodium hydride (54 mg, 1.34 mmol, 60% oil dispersion) in DMF similar to example 21 to give 32 mg (13%) of paint yellow solids. ¹H NMR (CDCl₃): 7.76 (d, J=8.7 Hz, 1H), 7.33 (d, J=7.2 Hz, 1H), 7.09 (d, J=8.7 Hz, 2H), 6.91-6.84 (m, 3H), 3.81 (s, 3H), 3.58 (s, 3H), 2.99 (s, 3H), 2.73 (s, 3H).

Example 41

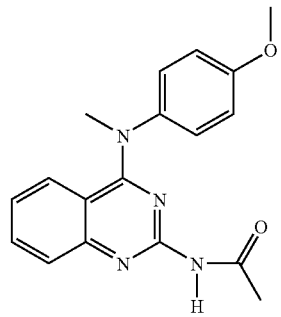

(2-Acetamido-quinazolin-4-yl)-(4-methoxy-phenyl)-methylamine

The title compound was prepared from (2-amino-quinazolin-4-yl)-(4-methoxy-phenyl)-methylamine (20 mg, 0.07 mmol), triethylamine (0.02 ml, 0.14 mmol), acetyl chloride (0.01 ml, 0.14 mmol) and DMAP (1 mg) in 2 ml of dichloromethane similar to example 28 to give 3 mg (13.6%) of white solids. ¹H NMR (CDCl₃): 7.88 (s, 1H), 7.62 (d, J=8.1 Hz, 1H), 7.52-7.47 (m, 1H), 7.15-7.12 (m, 2H), 6.95-6.86 (m, 4H), 3.85 (s, 3H), 3.55 (s, 3H), 2.68 (s, 3H).

Example 42

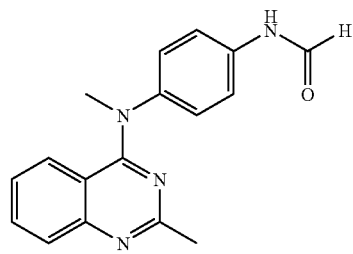

N-{4-[Methyl(2-methylquinazolin-4-yl)amino]phenyl}formamide

To a solution of formic acid 1 mL and acetic anhydride 1 mL, stirred at room temperature for 1 h, was added a solution of N-methyl-N-(2-methylquinazolin-4-yl)benzene-1,4-diamine 0.132 g (0.5 mmol) in CH₂Cl₂ 5 mL dropwise at 0° C. The reaction mixture was stirred at room temperature for 16 h. After concentration, the crude product was purified by recrystallization in EtOAc/MeOH to give the titled compound in 85% yield. The compound was further purified with preparative HPLC for analytical uses. ¹H NMR (CD₃OD, 400 MHz): δ 7.84-7.79 (m, 2H), 7.71-7.65 (m, 1H), 7.44-7.41 (m, 1H), 7.27-7.28 (m, 2H), 7.02-6.99 (m, 2H), [3.84 (s, 1H), 3.81 (s, 2H)], [2.78 (s, 1H), 2.76 (s, 2H)] (Two isomers were observed in 2:1 ratio.). m/e: 293.1438 (M+1).

Example 43

Identification of (2-Chloro-quinazolin-4-yl)-(4-dimethylaminophenyl)-methylamine and Analogs as Caspase Cascade Activators and Inducers of Apoptosis in Solid Tumor Cells Human breast cancer cell lines T-47D and DLD-1 were grown according to media component mixtures designated by American Type Culture Collection+10% FCS (Invitrogen Corporation), in a 5% $CO_2$-95% humidity incubator at 37° C. T-47D and DLD-1 cells were maintained at a cell density between 50 and 80% confluency at a cell density of 0.1 to $0.6 \times 10^6$ cells/mL. Cells were harvested at 600×g and resuspended at $0.65 \times 10^6$ cells/mL into appropriate media+10% FCS. An aliquot of 22.5 µL of cells was added to a well of a 384-well microtiter plate containing 2.5 µL of a 10% DMSO in RPMI-1640 media solution containing 0.16 to 100 µM of (2-chloro-quinazolin-4-yl)-(4-dimethylaminophenyl)-methylamine or other test compound (0.016 to 10 µM final). An aliquot of 22.5 µL of cells was added to a well of a 384-well microtiter plate containing 2.5 µL of a 10% DMSO in RPMI-1640 media solution without test compound as the control sample. The samples were mixed by agitation and then incubated at 37° C. for 48 h in a 5% $CO_2$-95% humidity incubator. After incubation, the samples were removed from the incubator and 25 µL of a solution containing 14 µM of N-(Ac-DEVD)-N'-ethoxycarbonyl-R110 fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model SPECTRAfluor Plus, Tecan), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - Control\ RFU_{(T=0)} = Net\ RFU_{(T=3h)}$$

The activity of caspase cascade activation was determined by the ratio of the net RFU value for (2-chloro-quinazolin-4-yl)-(4-dimethylaminophenyl)-methylamine or other test compounds to that of control samples. The $EC_{50}$ (nM) was determined by a sigmoidal dose-response calculation (Prism 3.0, GraphPad Software Inc.).

The capase activity (Ratio) and potency ($EC_{50}$) are summarized in Table I:

TABLE I

| Caspase Activity and Potency | | |
|---|---|---|
| | T-47D (24 hr) | |
| Exa. Cmpd. | Ratio | $EC_{50}$ (nM) |
| 1 | 8.1 | 47 |
| 2 | 1.1 | >10,000 |
| 3 | 8.2 | 75 |
| 4 | 8.5 | 73 |
| 5 | 9.3 | 32 |
| 6 | 9.2 | 210 |
| 7 | 3.4 | 18 |
| 8 | 8.0 | 558 |
| 9 | 5.6 | 258 |
| 10 | 2.6 | 979 |
| 11 | 4.0 | 5081 |
| 12 | 3.8 | 33 |
| 13 | 4.2 | 4 |
| 14 | 4.2 | 2360 |
| 15 | 3.9 | 39 |
| 16 | 2.4 | 14 |
| 17 | 3.7 | 619 |
| 18 | 4.7 | 221 |
| 19 | 4.3 | 214 |
| 20 | 1.1 | >10,000 |
| 21 | 7.5 | 4 |
| 22 | 8.7 | 2860 |
| 23 | 1.1 | >10,000 |
| 24 | 1.3 | >10,000 |
| 25 | 10.2 | 9 |
| 26 | 1.3 | >10,000 |
| 27 | 9.0 | 14 |
| 28 | 4.0 | 7 |
| 29 | 9.6 | 34 |
| 30 | 6.4 | 382 |
| 31 | 3.2 | 796 |
| 32 | 7.4 | 68 |
| 33 | 6.7 | 293 |
| 34 | 1.1 | >10,000 |
| 35 | 1.0 | >10,000 |
| 36 | 4.0 | 1871 |
| 37 | NA | NA |
| 38 | 0.9 | >10,000 |
| 39 | NA | NA |
| 40 | 2.7 | 290 |
| 41 | 3.5 | 27 |

NA = Not available

Thus, (2-chloro-quinazolin-4-yl)-(4-dimethylaminophenyl)-methylamine (Example 13) and analogs are identified as potent caspase cascade activators and inducers of apoptosis and are thus useful in treating the various diseases and disorders discussed above.

Example 44

Identification of Compounds as Antineoplastic Compounds that Inhibit Cell Proliferation ($GI_{50}$)

T-47D, DLD, H1299, MX-1 and SW620 cells are grown and harvested as in Example 43. An aliquot of 90 µL of cells ($4.4 \times 10^4$ cells/mL) is added to a well of a 96-well microtiter plate containing 5 µL of a 10% DMSO in RPMI-1640 media solution containing 10 nM to 100 µM of test compound (1 nM to 10 µM final). An aliquot of 45 µL of cells is added to a well of a 96-well microtiter plate containing 5 µL of a 10% DMSO in RPMI-1640 media solution without compound as the control sample for maximal cell proliferation ($L_{max}$). The samples are mixed by agitation and then incubated at 37° C. for 48 h in a 5% $CO_2$-95% humidity incubator. After incubation, the samples are removed from the incubator and 25 µL of CellTiter-Glo™ reagent (Promega) is added. The samples are mixed by agitation and incubated at room temperature for 10-15 min. Plates are then read using a luminescent plate reader (Model SPECTRAfluor Plus, Tecan) to give $L_{test}$ values.

Baseline for $GI_{50}$ (dose for 50% inhibition of cell proliferation) of initial cell numbers is determined by adding an aliquot of 45 µL of cells or 45 µL of media, respectively, to wells of a 96-well microtiter plate containing 5 μL of a 10% DMSO in RPMI-1640 media solution. The samples are mixed by agitation and then incubated at 37° C. for 0.5 h in a 5% $CO_2$-95% humidity incubator. After incubation, the samples are removed from the incubator and 25 μL of Cell-Titer-Glo™ reagent (Promega) is added. The samples are mixed by agitation and incubated at 37° C. for 10-15 min at room temperature in a 5% $CO_2$-95% humidity incubator. Fluorescence is read as above, ($L_{start}$) defining luminescence for initial cell number used as baseline in $GI_{50}$ determinations.

Calculation:

$GI_{50}$ (dose for 50% inhibition of cell proliferation) is the concentration where $[(L_{Test}-L_{start})/(L_{Max}-L_{start})]=0.5$.

Example 45

Inhibition of Tubulin Polymerization Assays

Lyophilized tubulin (Cytoskeleton #ML113, 1 mg, MAP-rich) is assayed for the effect of the test compound on tubulin polymerization as measured by change in fluorescence for 4',6-diamidino-2-phenylindole (DAPI) (Barron, D. M. et al. *Analytical Biochem.*, 2003, 315, 49-56.). One μl of serial dilutions of each test compound (from 100×DMSO stock) is added to a 96 well plate and preincubated for 30 minutes with 94 ul of the non-GTP supplemented tubulin supernatant. Five μl of DAPI/GTP solution is added to initiate polymerization and incubated for 30 minutes at 37° C. Fluorescence is read with excitation at 350 nm, emission at wavelength 485 nm on a Tecan Spectrafluor Plus. Polymerized tubulin (DMSO and with the tubulin stabilizer Taxol® (paclitaxel)) gives a higher DAPI fluorescence as compared to non-polymerized tubulin (vinblastine and colchicine used to determine baseline). The $IC_{50}$ for tubulin inhibition is the concentration found to decrease the fluorescence of DAPI by 50% as calculated with Prism 3.0.

Example 46

Multidrug Resistant Cell Assays

Cytotoxicity of compounds in multidrug resistant cells can be determined by administering compounds to cell lines that overexpress the multidrug resistance pump MDR-1 and determining the viability of the cell lines. NCI-ADR/Res and P388/ADR cell lines are known to overexpress the multidrug resistance pump MDR-1 (also known as P-glycoprotein-1; Pgp-1); whereas MCF-7 and P388 cell lines do not overexpress the multidrug resistance pumps MDR-1, MRP-1, or BCRP.

NCI-ADR/Res, MCF-7, P388, and P388/ADR cell lines are obtained from American Type Culture Collection (Manassas, Va.) and maintained in RPMI-1640 media supplemented with 10% FCS, 10 units/ml penicillin and streptomycin, 2 mM Glutamax and 1 mM sodium pyruvate (Invitrogen Corporation, Carlsbad, Calif.). For compound testing, cells are plated in 96 well dishes at a concentration of $1.5 \times 10^4$ cells/well. Cells are allowed to adhere to the plate overnight and then incubated with compounds at final concentrations ranging from 0.13 nM to 10 uM for 72 hours. Cell viability is then assessed using the ATP-lite reagent (Perkin Elmer, Foster City, Calif.). Plates are read on a Wallac Topcount luminescence reader (Perkin Elmer, Foster City, Calif.) and the results graphed in Prism software (Graphpad Software, Inc., San Diego, Calif.). Non-linear regression with variable slope analysis was performed to obtain $IC_{50}$ concentration values.

Example 47

Propidium Iodide and Annexin V Flow Cytometer-Based Assay to Detect Apoptosis

Necrotic versus apoptotic killing of human cell lines by compounds can be determined using dual annexin V-FITC and propidium iodide (PI) staining. Flipping of phosphatidylserine to the outer leaflet of the plasma membrane is a characteristic of all apoptotic cells. AnnexinV is a serum protein that binds to phosphatidylserine in the presence of the divalent cations (calcium). PI is a DNA stain that is excluded from live cells and is used to discriminate between cells with intact or damaged plasma membranes.

Cells are plated at varying densities in 6 well plates and treated with varying concentrations of compounds for 18-72 hours. Cells are grown in RPMI-1640 media supplemented with 10% FCS. DMSO concentrations do not exceed 0.1% v:v in any assay. All cells in the wells are harvested and rinsed 1× with cold Hanks buffered saline solution (HBSS) containing calcium and magnesium (Invitrogen, Carlsbad Calif.). Carefully aspirate supernatant after the wash and resuspend in 100 μl Annexin V-FITC (Annexin V/PI Apoptosis Detection Kit; R & D Systems TA4638; Minneapolis, Minn.) in binding buffer (10 mM HEPES pH 7.4, 150 mM NaCl, 5 mM KCl, 1 mM $MgCl_2$, 1.8 mM $CaCl_2$ and 2% bovine serum albumin w:v). Incubate in dark for 15 minutes on ice. Prior to analyzing samples, the volume is adjusted to 500 μl with 1× Binding Buffer and 25 μl PI is added per sample. Staining can be quantified on a flow cytometer (Becton-Dickenson, Franklin Lake, N.J.).

Example 48

| Injection Formulation | |
|---|---|
| Excipients | Amount |
| Active Compound | 5 mg |
| PEG-400 | 5 grams |
| TPGS | 10 grams |
| Benzyl alcohol | 0.5 gram |
| Ethanol | 2 grams |
| D5W | Add to make 50 mL |

An injection formulation of a compound selected from Formulae I-II (the "Active Compound") can be prepared according to the following method. Five mg of the Active Compound is dissolved into a mixture of the d-α-tocopheryl polyethylene glycol 1000 succinate (TPGS), PEG-400, ethanol, and benzyl alcohol. D5W is added to make a total volume of 50 mL and the solution is mixed. The resulting solution is filtered through a 0.2 μm disposable filter unit and is stored at 25° C. Solutions of varying strengths and volumes are prepared by altering the ratio of Active Compound in the mixture or changing the total amount of the solution.

Example 49

| Tablet Formulation | |
|---|---|
| Active Compound | 100.0 mg |
| Lactose | 100.0 mg |
| Corn Starch | 50.0 mg |
| Hydrogenated Vegetable Oil | 10.0 mg |
| Polyvinylpyrrolidone | 10.0 mg |
| | 270.0 mg |

A formulation of tablets of a compound selected from Formula I (e.g. Example 1 compound) (the "Active Compound") can be prepared according to the following method. One hundred mg of Active Compound) is mixed with 100 mg lactose. A suitable amount of water for drying is added and the mixture is dried. The mixture is then blended with 50 mg of corn starch, 10 mg hydrogenated vegetable oil, and 10 mg polyvinylpyrrolidinone. The resulting granules are compressed into tablets. Tablets of varying strengths are prepared by altering the ratio of Active Compound in the mixture or changing the total weight of the tablet.

Example 50

| Capsule Formulation | |
|---|---|
| Active Compound | 100.0 mg |
| Microcrystalline Cellulose | 200.0 mg |
| Corn Starch | 100.0 mg |
| Magnesium Stearate | 400.0 mg |
| | 800.0 mg |

A formulation of capsules containing 100.0 mg of a compound selected from Formulae I-II (e.g. Example 1 compound) (the "Active Compound") can be prepared according to the following method. One hundred mg of Active Compound is mixed with 200 mg of microcrystalline cellulose and 100 mg of corn starch. Four hundred mg of magnesium stearate is then blended into the mixture and the resulting blend is encapsulated into a gelatin capsule. Doses of varying strengths can be prepared by altering the ratio of the Active Compound to pharmaceutically acceptable carriers or changing the size of the capsule.

Example 51

Inhibition of Topoisomerase Assay

The ability of compounds to inhibit Topoisomerase II activity in relaxing supercoiled DNA can be determined by adding compounds to DNA samples and measuring the formation of topoisomers. The addition of Topoisomerase II to DNA samples results in the formation of topoisomers, which migrate faster than open circular DNA and slower than supercoiled DNA substrate when run on a gel. Ethidium Bromide, a known intercalator, and etoposide (VP 16), a known topoisomerase II inhibitor, are used as controls.

Assay reagents can be obtained from TopoGEN, Inc. (Columbus, Ohio). Samples are prepared by combining 10 μl of D/W, 2 μl of 10×TOPO II assay buffer, and 1 μl (0.25 μg) pRYG DNA. 5 μl of test compound, Ethidium Bromide, or VP16 are added to samples at varying concentrations. 2 μl of TOPO II (4 units in 20 μl reaction) is added to the samples and the samples are incubated at 37° C. in a water bath for 50 minutes. 2 μl of 10% SDS and 0. Proteinase K (500 μg/ml) are added and the samples are incubated again at 37° C. in a water bath for 50 minutes. Half of the reaction is loaded on a 1% gel without ethidium bromide and run in 1×TAE buffer at 20 volts/cm for 2 hours. The gel is stained with 0.5 μg/ml Ethidium Bromide for 10 seconds and destained in D/W for 30 seconds.

Inspection of the amount of supercoiled DNA present in the sample with 100 μM of test compound indicates whether inhibition of DNA relaxation is substantial. In order to distinguish between direct inhibition of topoisomerase II activity and intercalation, the effect of the test compound is determined on topoisomerase I-mediated relaxation of supercoiled DNA.

Samples are prepared by combining 10 μl of D/W, 2 μl of 10×TOPO II assay buffer, and 1 μl (0.25 μg) Form I DNA. 5 μl of test compound, Ethidium Bromide, or VP16 are added to samples at varying concentrations. 1 μl of TOPO 1 (5 units in 20 μl reaction) is added to the samples and the samples are incubated at 37° C. in a water bath for 50 minutes. 2 μl of 10% SDS and 0. Proteinase K (500 μg/ml) are added and the samples are incubated again at 37° C. in a water bath for 50 minutes. Half of the reaction is loaded on a 1% gel without ethidium bromide and run in 1×TAE buffer at 20 volts/cm for 2 hours. The gel is stained with 0.5 μg/ml Ethidium Bromide for 10 seconds and destained in D/W for 30 seconds.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:
1. A compound according to Formula I:

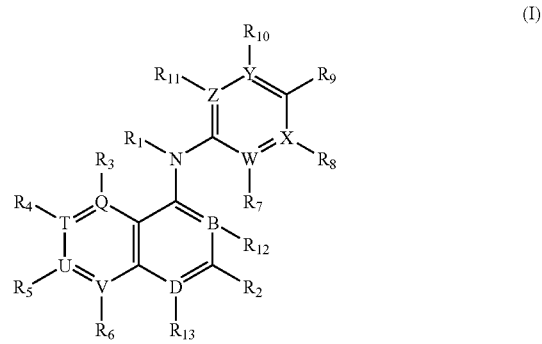

(I)

or a pharmaceutically acceptable salt thereof, wherein:
$R_1$ is $C_{1-6}$ alkyl;
$R_2$ is —$OR_{14}$, —$SR_{14}$, or $NR_{14}R_{15}$ wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl, and any of the groups are optionally substituted by halo, hydroxyl, carboxyl, amino, nitro, cyano, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{1-6}$ acyl, $C_{1-6}$ acylamino, or $C_{1-6}$ acyloxy;

$R_5$ is H, F, or $C_{1-3}$ alkyl;

$R_3$, $R_4$, and $R_6$-$R_{11}$ are independently selected from:
(a) H, halo, $N_3$, nitro, hydroxy, thiol, and CN,
(b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$,
(c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$), —C(=O)N($R^{52}$)($R^{53}$), —OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C(=$G^1$)$G^2R_{43}$, or -$G^4$C(=$G^1$)$G^2R_{43}$,
(d) —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$, $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

B and D are N and $R_{12}$ and $R_{13}$ are not present, Q, T, U, and V are C, and W, X, Y and Z are independently C or N, provided that W, X, Y or Z is N then there is no substituent at the N;

wherein any heterocycle or heteroaryl moiety is a 5 or 6-membered ring comprising from one to four heteroatoms independently selected from O, N, and S; and with the proviso that the compound is not $N^4$-methyl-$N^2$-(2-methyl-benzyl)-$N^4$-phenyl-quinazoline-2,4-diamine.

2. The compound of claim 1 wherein the compound has a structure according to Formula II:

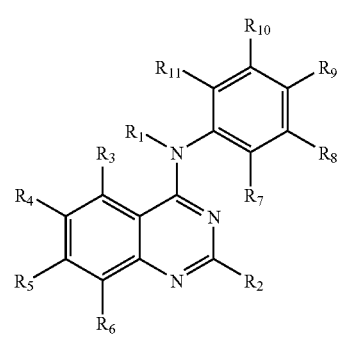

(II)

or a pharmaceutically acceptable salt thereof, wherein:

$R_1$ is $C_{1-2}$ alkyl;

$R_2$ is —$OR_{14}$, —$SR_{14}$, or $NR_{14}R_{15}$ wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl, and any of the groups are optionally substituted by halo, hydroxyl, carboxyl, amino, nitro, cyano, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{1-6}$ acyl, $C_{1-6}$ acylamino, or $C_{1-6}$ acyloxy;

$R_5$ is H, F, or $C_{1-3}$ alkyl;

$R_3$, $R_4$, and $R_6$-$R_{11}$ are independently selected from:
(a) H, halo, $N_3$, nitro, hydroxy, thiol, and CN,
(b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$, (c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$), —C(=O)N($R^{52}$)($R^{53}$), —OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C(=$G^1$)$G^2R_{43}$, or -$G^4$C(=$G^1$)$G^2R_{43}$;

(d) —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$, $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

wherein any heterocycle or heteroaryl moiety is a 5 or 6-membered ring comprising from one to four heteroatoms independently selected from O, N, and S.

3. The compound of claim 2, with the proviso that when $R_2$ is methylbenzylamino then $R_9$ is not H.

4. The compound of claim 3, wherein:

$R_1$ is $C_{1-2}$ alkyl;

$R_2$ is —$OR_{14}$, —$SR_{14}$, or $NR_{14}R_{14}$ wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl, and any of the groups are optionally substituted by halo, hydroxyl, carboxyl, amino, nitro, cyano, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{1-6}$ acyl, $C_{1-6}$ acylamino, or $C_{1-6}$ acyloxy;

$R_3$, $R_4$, $R_6$-$R_8$, $R_{10}$, $R_{11}$, and $R_{12}$ and $R_{13}$ if present, are independently $R_{16}$, $OR_{16}$, $SR_{16}$ or $NR_{16}R_{17}$, wherein $R_{16}$ and $R_{17}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy;

$R_5$ is H, F, or $C_{1-3}$ alkyl; and $R_9$ is H; OH; halo; $N_3$; $C_{1-6}$ alkyl; $C_{1-6}$ haloalkyl —$OR_{9a}$, wherein $R_{9a}$ is $C_{1-6}$ alkyl or $C_{1-6}$ haloalkyl; —NH($R^a$) or —N($R^a$)($R^b$) where $R^a$ and $R^b$ are independently $C_{1-6}$ alkyl, $C_{1-6}$ acyl, $C_{1-6}$ acyloxy, amino, —(C=O)N($R^c$)($R^d$) wherein $R^c$ and $R^d$ are independently H or $C_{1-6}$ alkyl; or —$COOR_{9b}$, wherein $R_{9b}$ is $C_{1-6}$ alkyl; optionally $R_9$ and one of $R_8$ and $R_{10}$ together form a 3, 4, 5, or 6-membered heterocycle; and any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy;

wherein, unless indicated otherwise, any heterocycle or heteroaryl moiety is a 5 or 6-membered ring comprising from one to four heteroatoms independently selected from O, N, and S.

5. The compound of claim 4, wherein:

$R_2$ is $NR_{14}R_{15}$, wherein $R_{14}$ is arylalkyl or heteroarylalkyl and $R_{15}$ is H, $C_{1-6}$ alkyl, $C_{2-6}$ alkenyl, $C_{2-6}$ alkynyl, or $C_{1-6}$ haloalkyl; and each group is optionally substituted by halo, hydroxyl, carboxyl, amino, nitro, cyano, $C_{1-3}$ alkyl, $C_{2-3}$ alkenyl, $C_{2-3}$ alkynyl, $C_{1-3}$ alkoxy, $C_{1-3}$ alkylthio, $C_{1-3}$ haloalkyl, $C_{1-3}$ acyl, $C_{1-3}$ acylamino, or $C_{1-6}$ acyloxy;

wherein any heteroaryl moiety is a 5 or 6-membered ring comprising from one to four heteroatoms independently selected from O, N, and S.

6. The compound of claim 4, wherein:

$R_9$ is H; OH; Cl; $N_3$; $C_{1-3}$ alkyl; $C_{1-3}$ haloalkyl; —$OR_{9a}$, wherein $R_{9a}$ is $C_{1-4}$ alkyl or $C_{1-3}$ haloalkyl; —NH($R^a$) or —N($R^a$)($R^b$) where $R^a$ and $R^b$ are independently $C_{1-3}$ alkyl, $C_{1-3}$ acyl, $C_{1-3}$ acyloxy, —(C=O)N($R^e$)($R^f$) wherein $R^e$ and $R^f$ are independently H, or $C_{1-3}$ alkyl; or —COOR$_{9b}$, wherein R$_{9b}$ is C$_{1-3}$ alkyl; and optionally R$_9$ and one of R$_8$ and R$_{10}$ together form a 3, 4, 5, or 6-membered heterocycle;

wherein any heterocycle moiety comprises from one to four heteroatoms independently selected from O, N, and S.

7. The compound of claim 5, wherein:
R$_9$ is selected from the group:
—OR$_{19}$, wherein R$_{19}$ is methyl, ethyl, fluoromethyl, or fluoroethyl;
—NHCH$_3$;
—N(CH$_3$)$_2$;
—N$_3$;
—COOR$_{20}$; and
—NC(O)N(R$_{21}$)(R$_{22}$) or —NC(O)R$_{20}$ wherein R$_{20}$ is methyl or ethyl; and R$_{21}$ and
R$_{22}$ are independently H, methyl or ethyl.

8. The compound of claim 7, wherein:
R$_3$ is H; halo; C$_{1-3}$ alkyl; or C$_{1-3}$ alkoxy;
R$_4$ and R$_6$ are independently H; halo; NO$_2$, N$_3$; C$_{1-6}$ alkyl; C$_{1-3}$ alkoxy; or —N(R$_{2b}$)(R$_{2c}$) wherein R$_{2b}$ and R$_{2c}$ are independently H, OH, C$_{1-6}$ alkyl, C$_{1-6}$ hydroxyalkyl, C$_{1-6}$ acyl, C$_{1-6}$ acyloxy, C$_{1-6}$ acylamido, or C$_{1-6}$ alkyl that is optionally substituted with —N(R$_{2d}$)(R$_{2e}$) wherein R$_{2d}$ and R$_{2e}$ are independently H, OH, C$_{1-3}$ alkyl or C$_{2-3}$ hydroxyalkyl, wherein
R$_{2b}$ and R$_{2c}$ together may form a 3, 4, 5 or 6-membered heterocycle, and wherein R$_{2b}$ and
R$_{2c}$ are not both OH, R$_{2d}$ and R$_{2e}$ are not both OH;
R$_5$ is H or F;
R$_7$ and R$_{11}$ are independently H; halo; CH$_3$; or OCH$_3$; and
R$_8$ and R$_{10}$ are independently H; halo; OH; N$_3$; C$_{1-3}$ alkyl; C$_{1-3}$ alkoxy; C$_{1-3}$ haloalkyl; —OR$_{9a}$, —SR$_{9a}$, where R$_{9a}$ is C$_{1-4}$ alkyl or C$_{1-3}$ haloalkyl; —NH(R$^a$) or —N(R$^a$)(R$^b$) where R$^a$ and R$^b$ are independently C$_{1-3}$ alkyl; or —COOR$_{9b}$, wherein R$_{9b}$ is C$_{1-3}$ alkyl;
wherein any heterocycle moiety comprises from one to four heteroatoms independently selected from O, N, and S.

9. A compound according to claim 1, wherein the compound is selected from:
(2-Benzylamino-quinazolin-4-yl)-(4-methoxyphenyl)-methylamine;
[2-(4-Methoxy-benzylamino)-quinazolin-4-yl)]-(4-methoxyphenyl)-methylamine;
or a pharmaceutically acceptable salt thereof.

10. A compound according to Formula I:

(I)

[Structure of Formula I]

11. A compound according to Formula II:

or a pharmaceutically acceptable salt thereof, wherein:
R$_1$ is C$_{1-2}$ alkyl;
R$_2$ is —N(R$^{50}$)C(=O)R$_{40}$, —N(R$^{50}$)C(=O)N(R$^{50}$)(R$^{51}$), C(=O)N(R$^{50}$)(R$^{51}$), or —OC(=O)N(R$^{50}$)(R$^{51}$);
wherein
R$_{40}$ is selected from: H, —OH, C$_{1-4}$ alkyl, C$_{2-4}$ alkenyl, C$_{2-4}$ alkynyl, C$_{1-4}$ alkoxy, C$_{2-4}$ alkenyloxy, C$_{2-4}$ alkynyloxy and C$_{1-4}$ alkylthiol, wherein R$_{40}$ is optionally substituted with from one to three substituents independently selected from halo, N$_3$, nitro, hydroxy, thiol, CN, and C$_{1-4}$ alkyl; and
R$^{50}$ and R$^{51}$ are independently H, OH(R$^{50}$ and R$^{51}$ are not both OH), C$_{1-4}$ alkyl, C$_{2-4}$ alkenyl, C$_{2-4}$ alkynyl, C$_{1-4}$ alkoxy, C$_{1-4}$ alkylthiol, C$_{2-4}$ alkenyloxy, C$_{2-4}$ alkynyloxy, C$_{1-4}$ haloalkyl, C$_{2-4}$ hydroxyalkyl, C$_{1-4}$ alkyl-O—C$_{1-4}$ alkyl-, or R$^{50}$ and R$^{51}$ together with the nitrogen atom to which they are both linked form a 3, 4, 5 or 6-membered heterocycle;
R$_3$, R$_4$, R$_6$-R$_8$, R$_{10}$-R$_{13}$ are independently R$_{16}$, OR$_{16}$, SR$_{16}$, NR$_{16}$R$_{17}$, or NO$_2$, wherein R$_{16}$ and R$_{17}$ are independently H, halo, hydroxyl, carboxyl, C$_{1-6}$ alkyl, C$_{2-6}$ alkenyl, C$_{2-6}$ alkynyl, or C$_{1-6}$ haloalkyl; wherein any of the groups are optionally substituted with one or more halo, C$_{1-6}$ haloalkyl, C$_1$-C$_6$ alkyl, C$_2$-C$_6$ alkenyl, C$_2$-C$_6$ alkynyl, C$_1$-C$_6$ hydroxyalkyl, nitro, amino, ureido, cyano, C$_{1-6}$ acylamino, hydroxy, thiol, C$_{1-6}$ acyloxy, azido, C$_1$-C$_6$ alkoxy, carboxy or C$_{1-2}$ alkylenedioxy;
R$_5$ is H, F, or C$_{1-3}$ alkyl;
R$_9$ is H; OH; halo; N$_3$; C$_{1-6}$ alkyl; C$_{1-6}$ haloalkyl —OR$_{9a}$, wherein R$_{9a}$ is C$_{1-6}$ alkyl or C$_{1-6}$ haloalkyl; —NH(R$^g$) or —N(R$^g$)(R$^h$) where R$^g$ and R$^h$ are independently C$_{1-6}$ alkyl, C$_{1-6}$ acyl, C$_{1-6}$ acyloxy, amino, —(C=O)N(R$^j$)(R$^k$) wherein R$^j$ and R$^k$ are independently H or C$_{1-6}$ alkyl; or —COOR$_{9b}$, wherein R$_{9b}$ is C$_{1-6}$ alkyl; optionally R$_9$ and one of R$_8$ and R$_{10}$ together form a 3, 4, 5, or 6-membered heterocycle; and any of the groups are optionally substituted with one or more halo, C$_{1-6}$ haloalkyl, C$_1$-C$_6$ alkyl, C$_2$-C$_6$ alkenyl, C$_2$-C$_6$ alkynyl, C$_1$-C$_6$ hydroxyalkyl, nitro, amino, ureido, cyano, C$_{1-6}$ acylamino, hydroxy, thiol, C$_{1-6}$ acyloxy, azido, C$_1$-C$_6$ alkoxy, carboxy or C$_{1-2}$ alkylenedioxy; and
B and D are N and R$_{12}$ and R$_{13}$ are not present, Q, T, U, and V are C, and W, X, Y and Z are independently C or N, provided that when W, X, Y or Z is N then there is no substituent at the N;
wherein any heterocycle moiety comprises from one to four heteroatoms independently selected from O, N, and S.

11. A compound according to Formula II:

(II)

[Structure of Formula II]

or a pharmaceutically acceptable salt thereof, wherein:

$R_1$ is $C_{1-2}$ alkyl;

$R_2$ is H; halo; $NHNH_2$, $N_3$; $C_{1-6}$ alkyl optionally substituted with OH or halo; $—OR_{2a}$ or $—SR_{2a}$ wherein $R_{ea}$ is $C_{1-6}$ alkyl optionally substituted with OH or halo; $—CO_2C_{1-3}$ alkyl;

or $—N(R^a)(R^b)$ wherein $R^a$ and $R^b$ are independently H, OH ($R^a$ and $R^b$ are not both OH), $C_{1-3}$ alkyl, $C_{1-6}$ hydroxyalkyl, $C_{1-3}$ acyl, $C_{1-3}$ acyloxy, $(C=O)N(R^e)(R^f)$ or $C_{1-6}$ alkyl that is optionally substituted with $—N(R^e)(R^f)$ wherein $R^e$ and $R^f$ are independently H, OH ($R^e$ and $R^f$ are not both OH), $C_{1-3}$ alkyl, or $C_{2-3}$ hydroxyalkyl, and wherein optionally $R^a$ and $R^b$ together with the nitrogen they both are linked to may form a 3, 4, 5 or 6-membered heterocycle;

$R_3$, $R_4$, $R_6$-$R_8$, $R_{10}$ and $R_{11}$ are independently $R_{16}$, $OR_{16}$, $SR_{16}$, $NR_{16}R_{17}$, or $NO_2$, wherein $R_{16}$ and $R_{17}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy;

$R_5$ is H, F, or $C_{1-3}$ alkyl; and $R_9$ is $—N(R^{50})C(=O)R_{40}$, $—N(R^{50})C(=O)N(R^{50})(R^{51})$, $C(=O)N(R^{50})(R^{51})$, or $—OC(=O)N(R^{50})(R^{51})$; wherein $R_{40}$ is selected from: H, —OH, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy and $C_{1-4}$ alkylthiol, wherein $R_{40}$ is optionally substituted with from one to three substituents independently selected from halo, $N_3$, nitro, hydroxy, thiol, CN, and $C_{1-4}$ alkyl; and $R^{50}$ and $R^{51}$ are independently H, OH ($R^{50}$ and $R^{51}$ are not both OH), $C_{1-4}$ alkyl, $C_{2-4}$ alkenyl, $C_{2-4}$ alkynyl, $C_{1-4}$ alkoxy, $C_{1-4}$ alkylthio, $C_{2-4}$ alkenyloxy, $C_{2-4}$ alkynyloxy, $C_{1-4}$ haloalkyl, $C_{2-4}$ hydroxyalkyl, $C_{1-4}$ alkyl-O—$C_{1-4}$ alkyl-, or $R^{50}$ and $R^{51}$ together with the nitrogen atom to which they are both linked form a 3, 4, 5 or 6-membered heterocycle;

wherein any heterocycle moiety comprises from one to four heteroatoms independently selected from O, N, and S.

12. The compound of claim 11, wherein $R_3$ is H; halo; $C_{1-3}$ alkyl; or $C_{1-3}$ alkoxy;

$R_4$ and $R_6$ are independently H; halo; $NO_2$, $N_3$; $C_{1-6}$ alkyl; $C_{1-3}$ alkoxy; or $—N(R_{2b})(R_{2c})$ wherein $R_{2b}$ and $R_{2c}$ are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with $—N(R_{2d})(R_{2e})$ wherein $R_{2d}$ and $R_{2e}$ are independently H, OH, $C_{1-3}$ alkyl or $C_{2-3}$ hydroxyalkyl, wherein $R_{2b}$ and $R_{2e}$ together may form a 3, 4, 5 or 6-membered heterocycle, and wherein $R_{2b}$ and $R_{2c}$ are not both OH, $R_{2d}$ and $R_{2e}$ are not both OH;

$R_5$ is H or F;

$R_7$ and $R_{11}$ are independently H; halo; $CH_3$; or $OCH_3$; and $R_8$ and $R_{10}$ are independently H; halo; OH; $N_3$; $C_{1-3}$ alkyl; $C_{1-3}$ alkoxy; $C_{1-3}$ haloalkyl; $—OR_{9a}$, $—SR_{9a}$, where $R_{9a}$ is $C_{1-4}$ alkyl or $C_{1-3}$ haloalkyl; $—NH(R^a)$ or $—N(R^a)(R^b)$ where $R^a$ and $R^b$ are independently $C_{1-3}$ alkyl; or $—COOR_{9b}$, wherein $R_{9b}$ is $C_{1-3}$ alkyl;

wherein any heterocycle moiety comprises from one to four heteroatoms independently selected from O, N, and S.

13. A compound according to claim 10 wherein the compound is selected from:

(2-Methylamino-quinazolin-4-yl)-(4-dimethylaminophenyl)-methylamine;

[2-(N-Methyl-acetamido)-quinazolin-4-yl]-(4-dimethylaminophenyl)-methylamine;

(4-Methoxy-phenyl)-(2-N-methylacetamido-quinazolin-4-yl)-methylamine;

(4-Methoxy-phenyl)-(2-N-methyl-methoxycarbonylamino-quinazolin-4-yl)-methylamine;

(2-Hydrazinyl-quinazolin-4-yl)-(4-methoxy-phenyl)-methylamine;

(2-Acetamido-quinazolin-4-yl)-(4-methoxy-phenyl)-methylamine; or a pharmaceutically acceptable salt thereof.

14. A compound according to claim 10 wherein the compound is selected from:

(2-Methyl-6-nitroquinazolin-4-yl)-(4-dimethylaminophenyl)-methylamine;

(2-Chloro-6-nitroquinazolin-4-yl)-(4-methoxyphenyl)-methylamine;

(6-Amino-2-methyl-quinazolin-4-yl)-(4-dimethylaminophenyl)-methylamine;

(2-Dimethylamino-6-nitroquinazolin-4-yl)-(4-methoxyphenyl)-methylamine;

(2-Methylamino-6-nitroquinazolin-4-yl)-(4-methoxyphenyl)-methylamine;

(6-Amino-2-dimethylamino-quinazolin-4-yl)-(4-methoxyphenyl)-methylamine;

(6-Amino-2-methylamino-quinazolin-4-yl)-(4-methoxyphenyl)-methylamine;

(6-Dimethylamino-2-methyl-quinazolin-4-yl)-(4-methoxy-phenyl)-methylamine;

(6-Acetamido-2-methyl-quinazolin-4-yl)-(4-methoxyphenyl)-methylamine;

(6-methoxycarbonylamino-2-methyl-quinazolin-4-yl)-(4-methoxy-phenyl)-methylamine;

(3,4-Dimethoxy-phenyl)-(2-methyl-6-nitro-quinazolin-4-yl)-methylamine;

(6-N-methyl-acetamido-2-methyl-quinazolin-4-yl)-(4-methoxy-phenyl) methylamine; or a pharmaceutically acceptable salt thereof.

15. A compound according to claim 10 wherein the compound is selected from:

(4-Acetamido-phenyl)-(2-methyl-quinazolin-4-yl)-methylamine;

(2-Methyl-quinazolin-4-yl)-(4-methoxycarbonylaminophenyl)-methylamine;

(2-Methyl-quinazolin-4-yl)-(4-ureido-phenyl)-methylamine;

(2-Methyl-quinazolin-4-yl)-(N-methyl-4-acetamido-phenyl)-methylamine;

(2-Methyl-quinazolin-4-yl)-(4-methylamino-phenyl)-methylamine;

(2-Methyl-quinazolin-4-yl)-[4-(N-methyl-methoxycarbonylamino)-phenyl]-methylamine;

(2-Chloro-quinazolin-4-yl)-(4-dimethylaminophenyl)-methylamine;

(4-Methylthio-phenyl)-(2-methyl-quinazolin-4-yl)-methylamine;

(3,4-Dimethoxy-phenyl)-(2-methyl-quinazolin-4-yl)-methylamine;

(2-Dimethylamino-pyridine-5-yl)-(2-methyl-quinazolin-4-yl)-methylamine;

N-{4-[Methyl(2-methylquinazolin-4-yl)amino]phenyl}formamide; or a pharmaceutically acceptable salt thereof.

16. A compound according to Formula I:

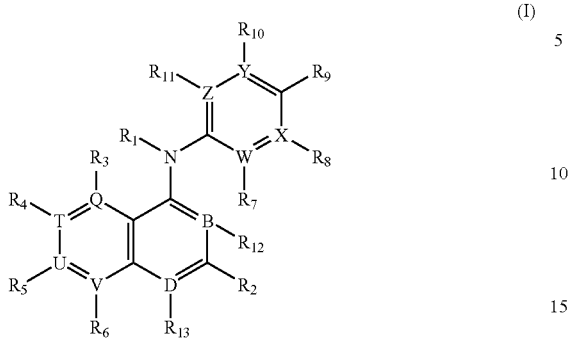

or a pharmaceutically acceptable salt thereof, wherein:
$R_1$ is methyl, ethyl, propyl, isopropyl, butyl, sec-butyl, tert-butyl, 3-pentyl, or hexyl;
$R_2$-$R_{13}$, are independently selected from:
  (a) H, halo, $N_3$, nitro, hydroxy, thiol, and CN,
  (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$,
  (c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$), —C(=O)N($R^{52}$)($R^{53}$), —OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C(=$G^1$)$G^2R_{43}$, or -$G^4$C(=$G^1$)$G^2R_{43}$,
  (d) —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$,
$G^1$ is S or N; $G^2$ and $G^3$ are independently S or N($R^{50}$); $G^4$ is N($R^{52}$);
$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;
$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;
$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;
$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;
$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;
$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;
B and D are N and $R_{12}$ and $R_{13}$ are not present, Q, T, U, and V are C, and W, X, Y and Z are independently C or N, provided that W, X, Y or Z is N then there is no substituent at the N;
wherein any heterocycle or heteroaryl moiety, unless indicated otherwise, is a 5 or 6-membered ring comprising from one to four heteroatoms independently selected from O, N, and S; and
wherein at least one of $R_2$-$R_{13}$ is $R_{40}$C(=$G^1$)-, $R_{40}$C(=$G^1$)$G^2$-, $R_{40}$C(=$G^1$)$G^2$($R_{50}$)—, —C(=$G^1$)$G^2R_{41}$ or -$G^3$C(=$G^1$)$G^2R_{41}$.

17. The compound of claim 16 wherein the compound has a structure according to Formula II:

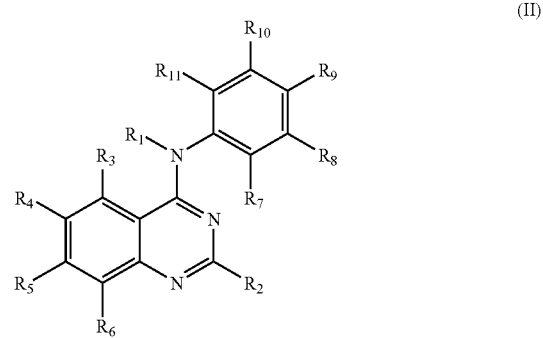

or a pharmaceutically acceptable salt thereof, wherein:

$R_1$ is methyl, ethyl, propyl, isopropyl, butyl, sec-butyl, tert-butyl, 3-pentyl, or hexyl;

$R_2$-$R_{11}$, are independently selected from:
- (a) H, halo, $N_3$, nitro, hydroxy, thiol, and CN,
- (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$,
- (c) carbocycle, heterocycle, aryl, and heteroaryl, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$), —C(=O)N($R^{52}$)($R^{53}$), —OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C(=$G^1$)$G^2R_{43}$, or -$G^4$C(=$G^1$)$G^2R_{43}$,
- (d) —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$, $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

wherein any heterocycle or heteroaryl moiety, unless indicated otherwise, is a 5 or 6-membered ring comprising from one to four heteroatoms independently selected from O, N, and S; and wherein at least one of $R_2$-$R_{11}$ is $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$.

18. The compound of claim 17 wherein:

$R_2$ is $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$; wherein $R_{40}$, $R_{41}$, $R^{50}$, $G^1$, $G^2$, and $G^3$ are as defined in claim 17.

19. The compound of claim 17 wherein:

$R_9$ is $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$; wherein $R_{40}$, $R_{41}$, $R^{50}$, $G^1$, $G^2$, and $G^3$ are as defined in claim 17.

20. The compound of claim 18 wherein:

$R_9$ is selected from the group:
—O$R_{19}$, wherein $R_{19}$ is selected from the group of methyl, ethyl, fluoromethyl, and fluoroethyl;
—NHCH$_3$;
—N(CH$_3$)$_2$;
—N$_3$;
—COO$R_{20}$; and
—NC(O)N($R_{21}$)($R_{22}$) or —NC(O)$R_{20}$ wherein $R_{20}$ is methyl or ethyl; and $R_{21}$ and $R_{22}$ are independently H, methyl or ethyl.

21. The compound of claim 20 wherein:

$R_3$ is H; halo; $C_{1-3}$ alkyl; or $C_{1-3}$ alkoxy;

$R_4$ and $R_6$ are independently H; halo; NO$_2$, N$_3$; $C_{1-6}$ alkyl; $C_{1-3}$ alkoxy; or —N($R_{2b}$)($R_{2c}$) wherein $R_{2b}$ and $R_{2c}$ are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with —N($R_{2d}$)($R_{2e}$) wherein $R_{2d}$ and $R_{2e}$ are independently H, OH, $C_{1-3}$ alkyl or $C_{2-3}$ hydroxyalkyl, wherein $R_{2b}$ and $R_{2c}$ together may form a 3, 4, 5 or 6-membered heterocycle, and wherein $R_{2b}$ and $R_{2c}$ are not both OH, $R_{2d}$ and $R_{2e}$ are not both OH;

$R_5$ is H or F;

$R_7$ and $R_{11}$ are independently H; halo; CH$_3$; or OCH$_3$; and $R_8$ and $R_{10}$ are independently H; halo; OH; N$_3$; $C_{1-3}$ alkyl; $C_{1-3}$ alkoxy; $C_{1-3}$ haloalkyl;
—O$R_{9a}$, —S$R_{9a}$, where $R_{9a}$ is $C_{1-4}$ alkyl or $C_{1-3}$ haloalkyl; —NH($R^a$) or —N($R^a$)($R^b$) where $R^a$ and $R^b$ are independently $C_{1-3}$ alkyl; or —COO$R_{9b}$, wherein $R_{9b}$ is $C_{1-3}$ alkyl;

wherein any heterocycle moiety comprises from one to four heteroatoms independently selected from O, N, and S.

22. A pharmaceutical composition comprising an effective amount of a compound according to claim 1, and a pharmaceutically acceptable carrier.

23. A pharmaceutical composition comprising an effective amount of a compound according to claim 10, and a pharmaceutically acceptable carrier.

24. A pharmaceutical composition comprising an effective amount of a compound according to claim 16, and a pharmaceutically acceptable carrier.

25. A pharmaceutical composition comprising an effective amount of a compound according to claim 11, and a pharmaceutically acceptable carrier.

26. The compound of claim 10, wherein $R_3$ is H; halo; $C_{1-3}$ alkyl; or $C_{1-3}$ alkoxy;

$R_4$ and $R_6$ are independently H; halo; $NO_2$, $N_3$; $C_{1-6}$ alkyl; $C_{1-3}$ alkoxy; or —$N(R_{2b})(R_{2c})$ wherein $R_{2b}$ and $R_{2c}$ are independently H, OH, $C_{1-6}$ alkyl, $C_{1-6}$ hydroxyalkyl, $C_{1-6}$ acyl, $C_{1-6}$ acyloxy, $C_{1-6}$ acylamido, or $C_{1-6}$ alkyl that is optionally substituted with —$N(R_{2d})(R_{2e})$ wherein $R_{2d}$ and $R_{2e}$ are independently H, OH, $C_{1-3}$ alkyl or $C_{2-3}$ hydroxyalkyl, wherein $R_{2b}$ and $R_{2c}$ together may form a 3, 4, 5 or 6-membered heterocycle, and wherein $R_{2b}$ and $R_{2c}$ are not both OH, $R_{2d}$ and $R_{2e}$ are not both OH;

$R_5$ is H or F;

$R_7$ and $R_{11}$ are independently H; halo; $CH_3$; or $OCH_3$; and $R_8$ and $R_{10}$ are independently H; halo; OH; $N_3$; $C_{1-3}$ alkyl; $C_{1-3}$ alkoxy; $C_{1-3}$ haloalkyl;

—$OR_{9a}$, —$SR_{9a}$, where $R_{9a}$ is $C_{1-4}$ alkyl or $C_{1-3}$ haloalkyl; —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl;

wherein any heterocycle moiety comprises from one to four heteroatoms independently selected from O, N, and S.

* * * * *